(12) United States Patent
Morton et al.

(10) Patent No.: US 7,030,235 B1
(45) Date of Patent: Apr. 18, 2006

(54) COMPOSITIONS TO DETECT LESIONS ASSOCIATED WITH HEARING LOSS IN THE COCHLEAR GENE, COCH5B2

(75) Inventors: Cynthia C. Morton, Newton Centre, MA (US); Nahid Robertson, Wellesley, MA (US)

(73) Assignee: The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/394,264

(22) Filed: Sep. 10, 1999

Related U.S. Application Data

(60) Provisional application No. 60/102,343, filed on Sep. 29, 1998.

(51) Int. Cl.
*C07H 21/04* (2006.01)
(52) U.S. Cl. .................. 536/24.3; 435/320.1; 530/350; 536/23.1; 536/24.31; 536/24.33
(58) Field of Classification Search ............. 435/320.1; 530/300, 350; 536/23.1, 24.3, 24.31, 24.33; 935/4, 23
See application file for complete search history.

(56) References Cited

FOREIGN PATENT DOCUMENTS

WO        WO 99/14328        *   3/1999

OTHER PUBLICATIONS

Robertson et al. Mapping and characterization of a novel cochlear gene in human and in mouse: a positional canidate gene for deafness disorder, DFNA9. Genomics. vol. 46 (Dec. 1997) pp. 345-354.*
GenBank/EMBL Database, accession # AF006740, # AF006741 (Jun. 4, 1997).*
Heller et al. Molecular markers for cell types of the inner ear and candidate genes for hearing disorders. Proceedings of the National Academey of Sciences. vol. 95 (1998) pp. 11400-11405.*
GenBank/EMBL Database, accession # AF012252 (Jul. 2, 1997).*
VanCoillie et al. The human MCP-2 gene (SCYA8): cloning, sequence analysis, tissue expression, and assignment to the CC chemokine gene contig on chromosome 17q11.2 Genomics. vol. 40 (Mar. 1997) pp. 323-331.*
GenBank/EMBL Database, accession # Z78142 (Aug. 6, 1996).*
GenBank/EMBL Database, accession # U09203 (Apr. 25, 1994).*
Scott et al. The pendered syndrome gene encodes a chloride-iodide transport protein. Nature Genetics (1999) vol. 21, pp. 440-443.*
Riffkin et al. A single amino-acid change between the antigenically different extracellular serine proteases V2 and B2 from *Dichelobacter nodosus*. Gene (1995) vol. 167, pp. 279-283.*
Harris et al. Polycystic kidney disease. 1: Identification and analysis of the primary defect. Journal of the American Society of Nephrology (1995) vol. 6, pp. 1125-1133.*
Ahn et al. The structural and functional diversity of distophin. Nature Genetics (1993) vol. 3, pp. 283-291.*
Cawthon et al. cDNA sequnece and Genomic structure of EVI2B, a gene lying within an intron of the neurofibromatosis type 1 gene. Genomics (1991) vol. 9, pp. 446-460.*
Duyk et al. (1992) *Nature Genet.*, 2:5-8.
Petit et al. (1996) *Nature Genet.*, 14:385-391.
van Camp et al. (1997) *Am. J. Human Genet.*, 60:758-764.
deKok et al. (1995) *Science*, 267:685-688.
Liu et al. (1997) *Nature Genet.*, 16:188-190.
Weil et al. (1997) *Nature Genet.*, 16:191-193.
Kelsell et al. (1997) *Nature*, 387:80-83.
Robertson et al. (1994) *Genomics*, 23:42-50.
Colombatti et al. (1993) *Matrix*, 77:2305-2315.
Colombatti et al. (1993) *Matrix*, 13:297-306.
Bonaldo et al. (1990) *Biochemistry*, 29:1245-1254.
Gerecke et al. (1997) *Genomics*, 41:236-242.
Jenkins et al. (1990) *J. Biol. Chem.*, 265:19624-19631.
Mancuso et al. (1991) *Biochemistry*, 30:253-269.
Bonaldo et al. (1989) *J. Biol. Chem.*, 264:5575-5580.
Koller et al. (1989) *EMBO J.*, 8:1073-1077.
Parente et al. (1991) *PNAS USA*, 88:6931-6935.
Christiano et al. (1994) *J. Biol. Chem.*, 269:20256-20262.
Wälchi et al. (1993) *Eur. J. Biochem.*, 212:483-490.
Agraves et al. (1987) *PNAS USA*, 84:464-468.
Haudenschild et al. (1995) *J. Biol.*, 270:23150-23154.
Roth et al. (1986) *Biochemistry*, 25:8357-8361.
Kalafatis et al. (1987) *Blood*, 70:1577-1583.
Pareti et al. (1987) *J. Biol. Chem.*, 262:13835-13847.
Manolis et al. (1996) *Hum. Mol. Genet.*, 5:1047-1050.
Khetarpal et al. (1991) *Arch. Otolaryngol. Head & Neck Surg.*, 117:1032-1042.
Khetarpal et al. (1993) *Arch. Otolaryngol. Head & Neck Surg.*, 119:106-108.
Fishman et al. (1983) *Arch. Ophthalmal.*, 101:1367-1374.

(Continued)

*Primary Examiner*—Ulrike Winkler
(74) *Attorney, Agent, or Firm*—Fish & Richardson P.C.

(57) ABSTRACT

The invention provides isolated nucleic acids molecules, designated COCH5B2 nucleic acid molecules, which encode polypeptides involved in inner ear biology. The invention also provides antisense nucleic acid molecules, expression vectors containing COCH5b2 nucleic acid molecules, host cells into which the expression vectors have been introduced, and non-human transgenic animals in which a COCH5b2 gene has been introduced or disrupted. The invention still further provides isolated COCH5B2 polypeptides, fusion polypeptides, antigenic peptides, and anti-COCH5B2 antibodies. Diagnostic, screening, and therapeutic methods utilizing compositions of the invention are also provided.

33 Claims, 9 Drawing Sheets

OTHER PUBLICATIONS

Figure 5:

Collins & Fuller (1968) *Science*, 162:1137-1139.
Halpin et al. (1996) *Am. J. Audiol.*, 5:105-111.
Muta et al. (1991) *J. Biol. Chem.*, 266:6554.
Iwanaga et al. (1992) *Thrombosis Res.*, 68:1.
Nakamura et al. (1998) *Eur. J. Biochem.*, 176:89.
Steel et al. (1994) *Trends in Genet.*, 10:428-434.

* cited by examiner

FIGURE 1

Human Coch-5B2 cDNA Sequence

1 GCACTCGGGC GCAGCCGGGT GGATCTCGAG CAGGTGTGAG
CAGCCTATCA GTCACCATGT CCGCAGCCTG GATCCCGGCT CTCGGCCTCG
GTGTGTGTCT GCTGCTGCTG CCGGGGCCCG CGGGCAGCGA GGGAGCCGCT
CCCATTGCTA TCACATGTTT TACCAGAGGC TTGGACATCA GGAAAGAGAA
AGCAGATGTC CTCTGCCCAG GGGGCTGCCC TCTTGAGGAA TTCTCTGTGT
ATGGGAACAT AGTATATGCT TCTGTATCGA GCATATGTGG GGCTGCTGTC
CACAGGGGAG TAATCAGCAA CTCAGGGGGA CCTGTACGAG TCTATAGCCT
ACCTGGTCGA GAAAACTATT CCTCAGTAGA TGCCAATGGC ATCCAGTCTC
AAATGCTTTC TAGATGGTCT GCTTCTTTCA CAGTAACTAA AGGCAAAAGT
AGTACACAGG AGGCCACAGG ACAAGCAGTG TCCACAGCAC ATCCACCAAC
AGGTAAACGA CTAAAGAAAA CACCCGAGAA GAAAACTGGC AATAAAGATT
GTAAAGCAGA CATTGCATTT CTGATTGATG GAAGCTTTAA TATTGGGCAG
CGCCGATTTA ATTTACAGAA GAATTTTGTT GGAAAAGTGG CTCTAATGTT
GGGAATTGGA ACAGAAGGAC CACATGTGGG CCTTGTTCAA GCCAGTGAAC
ATCCCAAAAT AGAATTTTAC TTGAAAAACT TTACATCAGC CAAAGATGTT
TTGTTTGCCA TAAAGGAAGT AGGTTTCAGA GGGGGTAATT CCAATACAGG
AAAAGCCTTG AAGCATACTG CTCAGAAATT CTTCACGGTA GATGCTGGAG
TAAGAAAAGG GATCCCCAAA GTGGTGGTGG TATTTATTGA TGGTTGGCCT
TCTGATGACA TCGAGGAAGC AGGCATTGTG GCCAGAGAGT TTGGTGTCAA
TGTATTTATA GTTTCTGTGG CCAAGCCTAT CCCTGAAGAA CTGGGGATGG
TTCAGGATGT CACATTTGTT GACAAGGCTG TCTGTCGGAA TAATGGCTTC
TTCTCTTACC ACATGCCCAA CTGGTTTGGC ACCACAAAAT ACGTAAAGCC
TCTGGTACAG AAGCTGTGCA CTCATGAACA AATGATGTGC AGCAAGACCT
GTTATAACTC AGTGAACATT GCCTTTCTAA TTGATGGCTC CAGCAGTGTT
GGAGATAGCA ATTTCCGCCT CATGCTTGAA TTTGTTTCCA ACATAGCCAA
GACTTTTGAA ATCTCGGACA TTGGTGCCAA GATAGCTGCT GTACAGTTTA
CTTATGATCA GCGCACGGAG TTCAGTTTCA CTGACTATAG CACCAAAGAG
AATGTCCTAG CTGTCATCAG AAACATCCGC TATATGAGTG GTGGAACAGC
TACTGGTGAT GCCATTTCCT TCACTGTTAG AAATGTGTTT GGCCCTATAA
GGGAGAGCCC CAACAAGAAC TTCCTAGTAA TTGTCACAGA TGGGCAGTCC
TATGATGATG TCCAAGGCCC TGCAGCTGCT GCACATGATG CAGGAATCAC
TATCTTCTCT GTTGGTGTGG CTTGGGCACC TCTGGATGAC CTGAAAGATA
TGGCTTCTAA ACCGAAGGAG TCTCATGCTT TCTTCACAAG AGAGTTCACA
GGATTAGAAC CAATTGTTTC TGATGTCATC AGAGGCATTT GTAGAGATTT
CTTAGAATCC CAGCAATAAT GGTAACATTT TGACAACTGA AAGAAAAAGT
ACAAGGGGAT CCAGTGTGTA AATTGTATTC TCATAATACT GAAATGCTTT
AGCATACTAG AATCAGATAC AAAACTATTA AGTATGTCAA CAGCCATTTA
GGCAAATAAG CACTCCTTTA AAGCCGCTGC CTTCTGGTTA CAATTTACAG
TGTACTTTGT TAAAAACACT GCTGAGGCTT CATAATCATG GCTCTTAGAA
ACTCAGGAAA GAGGAGATAA TGTGGATTAA AACCTTAAGA GTTCTAACCA
TGCCTACTAA ATGTACAGAT ATGCAAATTC CATAGCTCAA TAAAAGAATC

FIGURE 1 (CONTINUED)

```
TGATACTTAG ACCAAAAGCA ACATTCGTTC TCTAACCATT CTGTATTGAT
TATATAAGCA AAATGAAAAG AGAAACTTAA ATGAACACAG CTCTTTAACA
TGGTTCAGGT ACACATATTT TGACCCAAGT GGATATTTTC TTAAAACCAA
TCAATAATAG CTAGCTATTA CTGCAGACTA TAAAATCTGG ATATAGAAAG
GAGACCTGTA TCAAACTGCT TTTGTAGTGT GTTTTCATAA CAACTTATGA
CTAAAAATAT CACACTGAAT AAGAGAGCAG GATTGCCAGG TATTTTTCTA
TTTCTCTCCT TAATTTTATA TGTATATAGA TATATTTGGC TTATATTCTA
AGTCACCTAA GTACTTAAAA GTTAAGTTGG TAAAGTATTT ACTGACTGCT
TATAAACATT TAAAGACAAA GACATTTCAA ATAACTGCAG AAAAAATATT
GTAGTTTGAA TATTTAAGCA ATAAAACTGC TAGTGAGTTA TTGT
```

Human Coch-5B2 Amino Acid Sequence

```
1   MSAAWTPALG LGVCLLLLPG PAGSEGAAPI AITCFTRGLD IRKEKADVLC

PGGCPLEEFS VYGNIVYASV SSICGAAVHR GVISNSGGPV RVYSLPGREN

YSSVDANGIQ SQMLSRWSAS FTVTKGKSST QEATGQAVST AHPPTGKRLK

KTPEKKTGNK DCKADIAFLI DGSFNIGQRR FNLQKNFVGK VALMLGIGTE

GPHVGLVQAS EHPKIEFYLK NFTSAKDVLF AIKEVGFRGG NSNTGKALKH

TAQKFFTVDA GVRKGIPKVV VVFIDGWPSD DIEEAGIVAR EFGVNVFIVS

VAKPIPEELG MVQDVTFVDK AVCRNNGFFS YHMPNWFGTT KYVKPLVQKL

CTHEQMMCSK TCYNSVNIAF LIDGSSSVGD SNFRLMLEFV SNIAKTFEIS

DIGAKIAAVQ FTYDQRTEFS FTDYSTKENV LAVIRNIRYM SGGTATGDAI

SFTVRNVFGP IRESPNKNFL VIVTDGQSYD DVQGPAAAAH DAGITIFSVG

VAWAPLDDLK DMASKPKESH AFFTREFTGL EPIVSDVIRG ICRDFLESQQ
551 •
```

FIGURE 2

Mouse Coch-5B2 cDNA Sequence

1 CGGAGCCGCG CTTGCCGCAC TCGGGTGTAG CCGGGCGGAT
CCCACGCAGG TCCACGGAGA TCCTCGCCAT GCCCTCGTCC AGGATCCCTG
CTCTCTGCCT CGGTGCGTGG CTGCTGCTGC TGCTGCTGCC CCGGTTCGCG
CGCGCCGAGG GAGCGGTTCC CATTCCTGTC ACCTGCTTTA CCAGAGGCCT
GGATATCCGA AAAGAGAAAG CAGATGTTCT CTGCCCAGGA GGCTGCTCTC
TTGAGGAATT CTCTGTGTTT GGGAACATAG TGTATGCGTC AGTGTCCAGC
ATCTGCGGCG CTGCTGTCCA TAGGGGAGTG ATTGGCACCT CAGGGGGACC
TGTGCGTGTC TACAGCCTTC CTGGTCGAGA GAACTACTCC TCGGTAGATG
CCAACGGCAT CCAGTCTCAG ATGCTTTCCC GATGGTCCGC GTCCTTCGCT
GTGACCAAAG GCAAAAGCAG TACCCAGGAA GCCACAGGAC GGGCAGTGTC
CACAGCCCAC CCACCTTCAG GTAAAAGACT AAAGAAGACA CCAGAGAAGA
AGACTGGCAA CAAAGACTGT AAGGCAGACA TTGCATTTCT CATTGATGGA
AGCTTCAATA TTGGGCAGCG CCGATTTAAT TTGCAGAAGA ATTTTGTTGG
GAAAGTGGCA CTAATGTTGG GAATTGGAAC AGAAGGACCA CACGTGGGTC
TCGTTCAAGC CAGTGAACAC CCCAAAATAG AATTTTACTT GAAAAACTTT
ACTTCAGCCA AAGATGTCTT GTTTGCCATA AAGAAGTAG GTTTCCGAGG
GGGTAACTCC AACACAGGAA AAGCCTTGAA GCACACTGCT CAGAAATTCT
TTACAGCAGA CACTGGTGTG AGAAAAGGAA TACCAAAAGT GGTGGTAGTG
TTTATTGATG GTTGGCCCTC TGATGACATT GAGGAAGCAG GCATTGTGGC
CAGAGAGTTT GGTGTCAATG TATTTATAGT TTCTGTGGCC AAGCCCATTC
CTGAAGAACT GGGGATGGTT CAAGATGTTG CATTTGTTGA CAAGGCTGTG
TGTCGGAATA ATGGCTTCTT CTCTTATCAC ATGCCCAACT GGTTTGGCAC
TACAAAATAT GTGAAGCCTC TGGTGCAGAA GCTCTGTACG CACGAACAGA
TGATGTGCAG CAAAACCTGC TACAACTCAG TGAACATTGC CTTTCTGATT
GACGGCTCCA GCAGTGTTGG AGATAGCAAT TTCCGCCTCA TGCTAGAATT
TGTTTCTAAC ATAGCGAAGA CATTTGAAAT CTCAGACATT GGAGCCAAGA
TAGCTGCTGT ACAGTTCACT TATGACCAGC GCACCGAGTT CAGTTTCACT
GACTATAATA CCAAAGAGAA CGTCCTAGCT GTCCTAGCGA ACATCCGCTA
CATGAGTGGT GGCACAGCTA CTGGTGATGC CATCGCCTTT ACTGTTAGAA
ATGTATTTGG TCCCATAAGG GACAGCCCCA ACAAAAACTT CCTGGTTATT
GTCACAGATG GGCAGTCCTA TGATGATGTC CGAGGCCCTG CTGCAGCTGC
CCATGATGCA GGTATCACCA TCTTCTCTGT TGGTGTGGCT TGGGCACCGC
TGGATGACCT GAGAGATATG GCCTCTAAAC CCAAAGAGTC ACACGCTTTC
TTTACCAGAG AGTTCACAGG GTTAGAACCA ATTGTCTCTG ACGTCATCAG
AGGCATTTGT AGAGACTTCT TAGAATCCCA GCAATAACCG ATACTCTGAC
AACTCAAGGA ATACGTGCAA GGGGATCTAA TGTGCAAATT ATATTCTCAA
TGCCTATGTA ACTTTATAGC TTACCAGTGT CAAAAAATGC GTCCACAGCT
GTTTAAAGCA AATGAATATT CATGTGATGC TCACAATTTA GATTGGCCGA
GACTTGATAA TCAGGCCCTT AGAAACTCAG GAAAGAAGAG TTGTCATGGA
TTAACATTGG GAGTTCAAAT ATGCATTCAA GTGGATAGGT AAGCTACACA
GCTCAATAAA AGAACCTGGC GCTTACACAC AAAGCACTGT TCCCTCTTTA
ATCACTCTGC ATTGACCATG CAAGGAAAAC AGAACAGCTT TTAAACACAG

FIGURE 2 (CONTINUED)

```
ATCAAGTATA CATATTTTGA CCCATGTGGA TGTTTTCTTA AAACCAGCCA
AGAACAGACA GCTGTTATTA TGTGCACTAG CCATAACTAC ACATTATATG
GAATCATATA TCAAGCTTCT TTTGTAGTGT GTTTTCATAA CTTGATGGCT
GAAATACCAC ACTGAGTAAA GGTAGGATTG CCTGGTATTT TTCTATTTAT
ATCCTTAATT TTATGTGTAT AGACAGGCAT GTACTCCGAG GACTAAGAAA
ATGTTTAAGC AGATAACTTT TTTTTTTTGA AAAAAAAGAT GTGTCAAGTA
TTGTAACCGA AAAAATACAC AGCTTAATAG CTTGGCTGTC AGCAATAAAA
CTGCTAGTGA CTAAG
```

Mouse Coch-5B2 Amino Acid Sequence

1 MPSSRIPALC LGAWLLLLLL PRFARAEGAV PIPVTCFTRG LDIRKEKADV

LCPGGCSLEE FSVFGNIVYA SVSSICGAAV HRGVIGTSGG PVRVYSLPGR

ENYSSVDANG IQSQMLSRWS ASFAVTKGKS STQEATGRAV STAHPPSGKR

LKKTPEKKTG NKDCKADIAF LIDGSFNIGQ RRFNLQKNFV GKVALMLGIG

TEGPHVGLVQ ASEHPKIEFY LKNFTSAKDV LFAIKEVGFR GGNSNTGKAL

KHTAQKFFTA DTGVRKGIPK VVVVFIDGWP SDDIEEAGIV AREFGVNVFI

VSVAKPIPEE LGMVQDVAFV DKAVCRNNGF FSYHMPNWFG TTKYVKPLVQ

KLCTHEQMMC SKTCYNSVNI AFLIDGSSSV GDSNFRLMLE FVSNIAKTFE

ISDIGAKIAA VQFTYDQRTE FSFTDYNTKE NVLAVLANIR YMSGGTATGD

AIAFTVRNVF GPIRDSPNKN FLVIVTDGQS YDDVRGPAAA AHDAGITIFS

VGVAWAPLDD LRDMASKPKE SHAFFTREFT GLEPIVSDVI RGICRDFLES

QQ*

FIGURE 3

```
  1 MSAAWIPALGLG VCLLLLPGPAGSEGAAPIAITCFTRGLDIRKEKADV  48
    ...:    .    :       ..   . . ::
  1 .PSSR....C..AWLL.....RF.RA...V..PV..............  50

49 LCPGGCPLEEFSVYGNIVYASVSSICGAAVHRGVISNSGGPVRVYSLPGR  98
           .            :.                     :.
 51 ......S......F....................GT............ 100

99 ENYSSVDANGIQSQMLSRWSASFTVTKGKSSTQEATGQAVSTAHPPTGKR 148
                      .              .           .
101 ....................A..............R........S... 150

149 LKKTPEKKTGNKDCKADIAFLIDGSFNIGQRRFNLQKNFVGKVALMLGIG 198

151 ................................................ 200

199 TEGPHVGLVQASEHPKIEFYLKNFTSAKDVLFAIKEVGFRGGNSNTGKAL 248

201 ................................................ 250

249 KHTAQKFFTVDAGVRKGIPKVVVVFIDGWPSDDIEEAGIVAREFGVNVFI 298
             . .
251 .........A.T.................................... 300

299 VSVAKPIPEELGMVQDVTFVDKAVCRNNGFFSYHMPNWFGTTKYVKPLVQ 348
                   .
301 ................A............................... 350

349 KLCTHEQMMCSKTCYNSVNIAFLIDGSSSVGDSNFRLMLEFVSNIAKTFE 398

351 ................................................ 400

399 ISDIGAKIAAVQFTYDQRTEFSFTDYSTKENVLAVIRNIRYHSGGTATGD 448
                              .        :
401 ............................N........LA......... 450

449 AISFTVRNVFGPIRESPNKNFLVIVTDGQSYDDVQGPAAAAHDAGITIFS 498
      .           :                  .
451 ..A.........D..................R................ 500

499 VGVAWAPLDDLKDMASKPKESHAFFTREFTGLEPIVSDVIRGICRDFLES 548
               :
501 ...........R.................................... 550

549 QQ* 550

551 ... 552
```

FIGURE 4

SEQUENCE LISTING

```
<160> NUMBER OF SEQ ID NOS: 19

<210> SEQ ID NO 1
<211> LENGTH: 2534
<212> TYPE: DNA
<213> ORGANISM: Homo sapiens
<220> FEATURE:
<221> NAME/KEY: CDS
<222> LOCATION: (57)...(1706)

<400> SEQUENCE: 1
gcactcgggc gcagccgggt ggatctcgag caggtgtgag cagcctatca gtcacc atg      59
                                                                 Met
                                                                   1 tcc gca gcc tgg atc ccg gct ctc ggc ctc ggt gtg tgt ctg ctg ctg       107
Ser Ala Ala Trp Ile Pro Ala Leu Gly Leu Gly Val Cys Leu Leu Leu
          5                  10                  15 ctg ccg ggg ccc gcg ggc agc gag gga gcc gct ccc att gct atc aca       155
Leu Pro Gly Pro Ala Gly Ser Glu Gly Ala Ala Pro Ile Ala Ile Thr
     20                  25                  30
```

-continued

```
tgt ttt acc aga ggc ttg gac atc agg aaa gag aaa gca gat gtc ctc       203
Cys Phe Thr Arg Gly Leu Asp Ile Arg Lys Glu Lys Ala Asp Val Leu
 35                  40                  45 tgc cca ggg ggc tgc cct ctt gag gaa ttc tct gtg tat ggg aac ata       251
Cys Pro Gly Gly Cys Pro Leu Glu Glu Phe Ser Val Tyr Gly Asn Ile
 50                  55                  60                  65 gta tat gct tct gta tcg agc ata tgt ggg gct gct gtc cac agg gga       299
Val Tyr Ala Ser Val Ser Ser Ile Cys Gly Ala Ala Val His Arg Gly
                 70                  75                  80 gta atc agc aac tca ggg gga cct gta cga gtc tat agc cta cct ggt       347
Val Ile Ser Asn Ser Gly Gly Pro Val Arg Val Tyr Ser Leu Pro Gly
             85                  90                  95 cga gaa aac tat tcc tca gta gat gcc aat ggc atc cag tct caa atg       395
Arg Glu Asn Tyr Ser Ser Val Asp Ala Asn Gly Ile Gln Ser Gln Met
        100                 105                 110 ctt tct aga tgg tct gct tct ttc aca gta act aaa ggc aaa agt agt       443
Leu Ser Arg Trp Ser Ala Ser Phe Thr Val Thr Lys Gly Lys Ser Ser
115                 120                 125 aca cag gag gcc aca gga caa gca gtg tcc aca gca cat cca cca aca       491
Thr Gln Glu Ala Thr Gly Gln Ala Val Ser Thr Ala His Pro Pro Thr
130                 135                 140                 145 ggt aaa cga cta aag aaa aca ccc gag aag aaa act ggc aat aaa gat       539
Gly Lys Arg Leu Lys Lys Thr Pro Glu Lys Lys Thr Gly Asn Lys Asp
                150                 155                 160 tgt aaa gca gac att gca ttt ctg att gat gga agc ttt aat att ggg       587
Cys Lys Ala Asp Ile Ala Phe Leu Ile Asp Gly Ser Phe Asn Ile Gly
            165                 170                 175 cag cgc cga ttt aat tta cag aag aat ttt gtt gga aaa gtg gct cta       635
Gln Arg Arg Phe Asn Leu Gln Lys Asn Phe Val Gly Lys Val Ala Leu
        180                 185                 190 atg ttg gga att gga aca gaa gga cca cat gtg ggc ctt gtt caa gcc       683
Met Leu Gly Ile Gly Thr Glu Gly Pro His Val Gly Leu Val Gln Ala
195                 200                 205 agt gaa cat ccc aaa ata gaa ttt tac ttg aaa aac ttt aca tca gcc       731
Ser Glu His Pro Lys Ile Glu Phe Tyr Leu Lys Asn Phe Thr Ser Ala
210                 215                 220                 225 aaa gat gtt ttg ttt gcc ata aag gaa gta ggt ttc aga ggg ggt aat       779
Lys Asp Val Leu Phe Ala Ile Lys Glu Val Gly Phe Arg Gly Gly Asn
                230                 235                 240 tcc aat aca gga aaa gcc ttg aag cat act gct cag aaa ttc ttc acg       827
Ser Asn Thr Gly Lys Ala Leu Lys His Thr Ala Gln Lys Phe Phe Thr
            245                 250                 255 gta gat gct gga gta aga aaa ggg atc ccc aaa gtg gtg gtg gta ttt       875
Val Asp Ala Gly Val Arg Lys Gly Ile Pro Lys Val Val Val Val Phe
        260                 265                 270 att gat ggt tgg cct tct gat gac atc gag gaa gca ggc att gtg gcc       923
Ile Asp Gly Trp Pro Ser Asp Asp Ile Glu Glu Ala Gly Ile Val Ala
275                 280                 285 aga gag ttt ggt gtc aat gta ttt ata gtt tct gtg gcc aag cct atc       971
Arg Glu Phe Gly Val Asn Val Phe Ile Val Ser Val Ala Lys Pro Ile
290                 295                 300                 305 cct gaa gaa ctg ggg atg gtt cag gat gtc aca ttt gtt gac aag gct      1019
Pro Glu Glu Leu Gly Met Val Gln Asp Val Thr Phe Val Asp Lys Ala
                310                 315                 320 gtc tgt cgg aat aat ggc ttc ttc tct tac cac atg ccc aac tgg ttt      1067
Val Cys Arg Asn Asn Gly Phe Phe Ser Tyr His Met Pro Asn Trp Phe
            325                 330                 335 ggc acc aca aaa tac gta aag cct ctg gta cag aag ctg tgc act cat      1115
Gly Thr Thr Lys Tyr Val Lys Pro Leu Val Gln Lys Leu Cys Thr His
        340                 345                 350
```

-continued

| | |
|---|---|
| gaa caa atg atg tgc agc aag acc tgt tat aac tca gtg aac att gcc<br>Glu Gln Met Met Cys Ser Lys Thr Cys Tyr Asn Ser Val Asn Ile Ala<br>355                           360                     365 | 1163 |
| ttt cta att gat ggc tcc agc agt gtt gga gat agc aat ttc cgc ctc<br>Phe Leu Ile Asp Gly Ser Ser Ser Val Gly Asp Ser Asn Phe Arg Leu<br>370                         375                       380                   385 | 1211 |
| atg ctt gaa ttt gtt tcc aac ata gcc aag act ttt gaa atc tcg gac<br>Met Leu Glu Phe Val Ser Asn Ile Ala Lys Thr Phe Glu Ile Ser Asp<br>                     390                       395                     400 | 1259 |
| att ggt gcc aag ata gct gct gta cag ttt act tat gat cag cgc acg<br>Ile Gly Ala Lys Ile Ala Ala Val Gln Phe Thr Tyr Asp Gln Arg Thr<br>                405                       410                     415 | 1307 |
| gag ttc agt ttc act gac tat agc acc aaa gag aat gtc cta gct gtc<br>Glu Phe Ser Phe Thr Asp Tyr Ser Thr Lys Glu Asn Val Leu Ala Val<br>                     420                       425                     430 | 1355 |
| atc aga aac atc cgc tat atg agt ggt gga aca gct act ggt gat gcc<br>Ile Arg Asn Ile Arg Tyr Met Ser Gly Gly Thr Ala Thr Gly Asp Ala<br>435                           440                     445 | 1403 |
| att tcc ttc act gtt aga aat gtg ttt ggc cct ata agg gag agc ccc<br>Ile Ser Phe Thr Val Arg Asn Val Phe Gly Pro Ile Arg Glu Ser Pro<br>450                           455                     460                   465 | 1451 |
| aac aag aac ttc cta gta att gtc aca gat ggg cag tcc tat gat gat<br>Asn Lys Asn Phe Leu Val Ile Val Thr Asp Gly Gln Ser Tyr Asp Asp<br>                     470                       475                     480 | 1499 |
| gtc caa ggc cct gca gct gct gca cat gat gca gga atc act atc ttc<br>Val Gln Gly Pro Ala Ala Ala Ala His Asp Ala Gly Ile Thr Ile Phe<br>                485                       490                     495 | 1547 |
| tct gtt ggt gtg gct tgg gca cct ctg gat gac ctg aaa gat atg gct<br>Ser Val Gly Val Ala Trp Ala Pro Leu Asp Asp Leu Lys Asp Met Ala<br>                     500                       505                     510 | 1595 |
| tct aaa ccg aag gag tct cat gct ttc ttc aca aga gag ttc aca gga<br>Ser Lys Pro Lys Glu Ser His Ala Phe Phe Thr Arg Glu Phe Thr Gly<br>515                           520                     525 | 1643 |
| tta gaa cca att gtt tct gat gtc atc aga ggc att tgt aga gat ttc<br>Leu Glu Pro Ile Val Ser Asp Val Ile Arg Gly Ile Cys Arg Asp Phe<br>530                           535                     540                   545 | 1691 |
| tta gaa tcc cag caa taatggtaac attttgacaa ctgaaagaaa aagtacaagg<br>Leu Glu Ser Gln Gln<br>                   550 | 1746 |
| ggatccagtg tgtaaattgt attctcataa tactgaaatg ctttagcata ctagaatcag | 1806 |
| atacaaaact attaagtatg tcaacagcca tttaggcaaa taagcactcc tttaaagccg | 1866 |
| ctgccttctg gttacaattt acagtgtact ttgttaaaaa cactgctgag gcttcataat | 1926 |
| catggctctt agaaactcag gaaagaggag ataatgtgga ttaaaacctt aagagttcta | 1986 |
| accatgccta ctaaatgtac agatatgcaa attccatagc tcaataaaag aatctgatac | 2046 |
| ttagaccaaa agcaacattc gttctctaac cattctgtat tgattatata agcaaaatga | 2106 |
| aaagagaaac ttaaatgaac acagctcttt aacatggttc aggtacacat attttgaccc | 2166 |
| aagtggatat tttcttaaaa ccaatcaata atagctagct attactgcag actataaaat | 2226 |
| ctggatatag aaaggagacc tgtatcaaac tgcttttgta gtgtgttttc ataacaactt | 2286 |
| atgactaaaa atatcacact gaataagaga gcaggattgc caggtatttt tctatttctc | 2346 |
| tccttaattt tatatgtata tagatatatt tggcttatat tctaagtcac ctaagtactt | 2406 |
| aaaagttaag ttggtaaagt atttactgac tgcttataaa catttaaaga caaagacatt | 2466 |
| tcaaataact gcagaaaaaa tattgtagtt tgaatattta agcaataaaa ctgctagtga | 2526 |
| gttattgt | 2534 |

-continued

<210> SEQ ID NO 2
<211> LENGTH: 550
<212> TYPE: PRT
<213> ORGANISM: Homo sapiens

<400> SEQUENCE: 2

```
Met Ser Ala Ala Trp Ile Pro Ala Leu Gly Leu Gly Val Cys Leu Leu
 1               5                  10                  15

Leu Leu Pro Gly Pro Ala Gly Ser Glu Gly Ala Ala Pro Ile Ala Ile
            20                  25                  30

Thr Cys Phe Thr Arg Gly Leu Asp Ile Arg Lys Glu Lys Ala Asp Val
        35                  40                  45

Leu Cys Pro Gly Gly Cys Pro Leu Glu Glu Phe Ser Val Tyr Gly Asn
    50                  55                  60

Ile Val Tyr Ala Ser Val Ser Ser Ile Cys Gly Ala Ala Val His Arg
65                  70                  75                  80

Gly Val Ile Ser Asn Ser Gly Pro Val Arg Val Tyr Ser Leu Pro
                85                  90                  95

Gly Arg Glu Asn Tyr Ser Ser Val Asp Ala Asn Gly Ile Gln Ser Gln
            100                 105                 110

Met Leu Ser Arg Trp Ser Ala Ser Phe Thr Val Thr Lys Gly Lys Ser
        115                 120                 125

Ser Thr Gln Glu Ala Thr Gly Gln Ala Val Ser Thr Ala His Pro Pro
    130                 135                 140

Thr Gly Lys Arg Leu Lys Lys Thr Pro Glu Lys Lys Thr Gly Asn Lys
145                 150                 155                 160

Asp Cys Lys Ala Asp Ile Ala Phe Leu Ile Asp Gly Ser Phe Asn Ile
                165                 170                 175

Gly Gln Arg Arg Phe Asn Leu Gln Lys Asn Phe Val Gly Lys Val Ala
            180                 185                 190

Leu Met Leu Gly Ile Gly Thr Glu Gly Pro His Val Gly Leu Val Gln
        195                 200                 205

Ala Ser Glu His Pro Lys Ile Glu Phe Tyr Leu Lys Asn Phe Thr Ser
    210                 215                 220

Ala Lys Asp Val Leu Phe Ala Ile Lys Glu Val Gly Phe Arg Gly Gly
225                 230                 235                 240

Asn Ser Asn Thr Gly Lys Ala Leu Lys His Thr Ala Gln Lys Phe Phe
                245                 250                 255

Thr Val Asp Ala Gly Val Arg Lys Gly Ile Pro Lys Val Val Val Val
            260                 265                 270

Phe Ile Asp Gly Trp Pro Ser Asp Asp Ile Glu Glu Ala Gly Ile Val
        275                 280                 285

Ala Arg Glu Phe Gly Val Asn Val Phe Ile Val Ser Val Ala Lys Pro
    290                 295                 300

Ile Pro Glu Glu Leu Gly Met Val Gln Asp Val Thr Phe Val Asp Lys
305                 310                 315                 320

Ala Val Cys Arg Asn Asn Gly Phe Phe Ser Tyr His Met Pro Asn Trp
                325                 330                 335

Phe Gly Thr Thr Lys Tyr Val Lys Pro Leu Val Gln Lys Leu Cys Thr
            340                 345                 350

His Glu Gln Met Met Cys Ser Lys Thr Cys Tyr Asn Ser Val Asn Ile
        355                 360                 365

Ala Phe Leu Ile Asp Gly Ser Ser Ser Val Gly Asp Ser Asn Phe Arg
    370                 375                 380
```

-continued

```
Leu Met Leu Glu Phe Val Ser Asn Ile Ala Lys Thr Phe Glu Ile Ser
385                 390                 395                 400
Asp Ile Gly Ala Lys Ile Ala Ala Val Gln Phe Thr Tyr Asp Gln Arg
                405                 410                 415
Thr Glu Phe Ser Phe Thr Asp Tyr Ser Thr Lys Glu Asn Val Leu Ala
            420                 425                 430
Val Ile Arg Asn Ile Arg Tyr Met Ser Gly Gly Thr Ala Thr Gly Asp
        435                 440                 445
Ala Ile Ser Phe Thr Val Arg Asn Val Phe Gly Pro Ile Arg Glu Ser
    450                 455                 460
Pro Asn Lys Asn Phe Leu Val Ile Val Thr Asp Gly Gln Ser Tyr Asp
465                 470                 475                 480
Asp Val Gln Gly Pro Ala Ala Ala His Asp Ala Gly Ile Thr Ile
                485                 490                 495
Phe Ser Val Gly Val Ala Trp Ala Pro Leu Asp Asp Leu Lys Asp Met
            500                 505                 510
Ala Ser Lys Pro Lys Glu Ser His Ala Phe Phe Thr Arg Glu Phe Thr
        515                 520                 525
Gly Leu Glu Pro Ile Val Ser Asp Val Ile Arg Gly Ile Cys Arg Asp
    530                 535                 540
Phe Leu Glu Ser Gln Gln
545                 550

<210> SEQ ID NO 3
<211> LENGTH: 1650
<212> TYPE: DNA
<213> ORGANISM: Homo sapiens

<400> SEQUENCE: 3
atgtccgcag cctggatccc ggctctcggc ctcggtgtgt gtctgctgct gctgccgggg       60
cccgcgggca gcgagggagc cgctcccatt gctatcacat gttttaccag aggcttggac      120
atcaggaaag agaaagcaga tgtcctctgc ccagggggct gccctcttga ggaattctct      180
gtgtatggga acatagtata tgcttctgta tcgagcatat gtggggctgc tgtccacagg      240
ggagtaatca gcaactcagg ggacctgta cgagtctata gcctacctgg tcgagaaaac       300
tattcctcag tagatgccaa tggcatccag tctcaaatgc tttctagatg gtctgcttct      360
ttcacagtaa ctaaaggcaa agtagtaca caggaggcca caggacaagc agtgtccaca      420
gcacatccac caacaggtaa acgactaaag aaaacacccg agaagaaaac tggcaataaa      480
gattgtaaag cagacattgc atttctgatt gatggaagct taatattgg gcagcgccga      540
tttaatttac agaagaattt tgttggaaaa gtggctctaa tgttgggaat ggaacagaa       600
ggaccacatg tgggccttgt tcaagccagt gaacatccca aaatagaatt ttacttgaaa      660
aactttacat cagccaaaga tgttttgttt gccataaagg aagtaggttt cagagggggt      720
aattccaata caggaaaagc cttgaagcat actgctcaga aattcttcac ggtagatgct      780
ggagtaagaa aagggatccc caaagtggtg gtgtatttta ttgatggttg gccttctgat      840
gacatcgagg aagcaggcat tgtggccaga gagtttggtg tcaatgtatt tatagtttct      900
gtggccaagc ctatccctga gaactgggga tggttcagg atgtcacatt tgttgacaag      960
gctgtctgtc ggaataatgg cttcttctct taccacatgc ccaactggtt tggcaccaca     1020
aaatacgtaa agcctctggt acagaagctg tgcactcatg aacaaatgat gtgcagcaag     1080
acctgttata actcagtgaa cattgccttt ctaattgatg gctccagcag tgttggagat     1140
```

```
agcaatttcc gcctcatgct tgaatttgtt tccaacatag ccaagacttt tgaaatctcg    1200
gacattggtg ccaagatagc tgctgtacag tttacttatg atcagcgcac ggagttcagt    1260
ttcactgact atagcaccaa agagaatgtc ctagctgtca tcagaaacat ccgctatatg    1320
agtggtggaa cagctactgg tgatgccatt tccttcactg ttagaaatgt gtttggccct    1380 ataaggaga gccccaacaa gaacttccta gtaattgtca cagatgggca gtcctatgat    1440
gatgtccaag ccctgcagc tgctgcacat gatgcaggaa tcactatctt ctctgttggt    1500
gtggcttggg cacctctgga tgacctgaaa gatatggctt ctaaaccgaa ggagtctcat    1560
gctttcttca agagagtt cacaggatta gaaccaattg tttctgatgt catcagaggc    1620
atttgtagag atttcttaga atcccagcaa                                    1650
```

<210> SEQ ID NO 4
<211> LENGTH: 145
<212> TYPE: PRT
<213> ORGANISM: Homo sapiens

<400> SEQUENCE: 4

```
Asp Ile Ala Phe Leu Ile Asp Gly Ser Phe Asn Ile Gly Gln Arg Arg
  1               5                  10                  15

Phe Asn Leu Gln Lys Asn Phe Val Gly Lys Val Ala Leu Met Leu Gly
                 20                  25                  30

Ile Gly Thr Glu Gly Pro His Val Gly Leu Val Gln Ala Ser Glu His
             35                  40                  45

Pro Lys Ile Glu Phe Tyr Leu Lys Asn Phe Thr Ser Ala Lys Asp Val
         50                  55                  60

Leu Phe Ala Ile Lys Glu Val Gly Phe Arg Gly Gly Asn Ser Asn Thr
 65                  70                  75                  80

Gly Lys Ala Leu Lys His Thr Ala Gln Lys Phe Phe Thr Val Asp Ala
                 85                  90                  95

Gly Val Arg Lys Gly Ile Pro Lys Val Val Val Phe Ile Asp Gly
            100                 105                 110

Trp Pro Ser Asp Asp Ile Glu Glu Ala Gly Ile Val Ala Arg Glu Phe
            115                 120                 125

Gly Val Asn Val Phe Ile Val Ser Val Ala Lys Pro Ile Pro Glu Glu
            130                 135                 140

Leu
145
```

<210> SEQ ID NO 5
<211> LENGTH: 149
<212> TYPE: PRT
<213> ORGANISM: Homo sapiens

<400> SEQUENCE: 5

```
Val Asn Ile Ala Phe Leu Ile Asp Gly Ser Ser Ser Val Gly Asp Ser
  1               5                  10                  15

Asn Phe Arg Leu Met Leu Glu Phe Val Ser Asn Ile Ala Lys Thr Phe
                 20                  25                  30

Glu Ile Ser Asp Ile Gly Ala Lys Ile Ala Ala Val Gln Phe Thr Tyr
             35                  40                  45

Asp Gln Arg Thr Glu Phe Ser Phe Thr Asp Tyr Ser Thr Lys Glu Asn
         50                  55                  60

Val Leu Ala Val Ile Arg Asn Ile Arg Tyr Met Ser Gly Gly Thr Ala
 65                  70                  75                  80
```

-continued

```
        Thr Gly Asp Ala Ile Ser Phe Thr Val Arg Asn Val Phe Gly Pro Ile
                     85                  90                  95

Arg Glu Ser Pro Asn Lys Asn Phe Leu Val Ile Val Thr Asp Gly Gln
                    100                 105                 110

Ser Tyr Asp Asp Val Gln Gly Pro Ala Ala Ala His Asp Ala Gly
                115                 120                 125

Ile Thr Ile Phe Ser Val Gly Val Ala Trp Ala Pro Leu Asp Asp Leu
        130                 135                 140

Lys Asp Met Ala Ser
        145

<210> SEQ ID NO 6
<211> LENGTH: 2455
<212> TYPE: DNA
<213> ORGANISM: Mus musculus
<220> FEATURE:
<221> NAME/KEY: CDS
<222> LOCATION: (69)...(1725)

<400> SEQUENCE: 6
cggagccgcg cttgccgcac tcgggtgtag ccgggcggat cccacgcagg tccacggaga       60 tcctcgcc atg ccc tcg tcc agg atc cct gct ctc tgc ctc ggt gcg tgg      110
         Met Pro Ser Ser Arg Ile Pro Ala Leu Cys Leu Gly Ala Trp
          1               5                  10 ctg ctg ctg ctg ctg ctg ccc cgg ttc gcg cgc gcc gag gga gcg gtt      158
Leu Leu Leu Leu Leu Leu Pro Arg Phe Ala Arg Ala Glu Gly Ala Val
 15                  20                  25                  30 ccc att cct gtc acc tgc ttt acc aga ggc ctg gat atc cga aaa gag      206
Pro Ile Pro Val Thr Cys Phe Thr Arg Gly Leu Asp Ile Arg Lys Glu
                 35                  40                  45 aaa gca gat gtt ctc tgc cca gga ggc tgc tct ctt gag gaa ttc tct      254
Lys Ala Asp Val Leu Cys Pro Gly Gly Cys Ser Leu Glu Glu Phe Ser
             50                  55                  60 gtg ttt ggg aac ata gtg tat gcg tca gtg tcc agc atc tgc ggc gct      302
Val Phe Gly Asn Ile Val Tyr Ala Ser Val Ser Ser Ile Cys Gly Ala
 65                  70                  75 gct gtc cat agg gga gtg att ggc acc tca ggg gga cct gtg cgt gtc      350
Ala Val His Arg Gly Val Ile Gly Thr Ser Gly Gly Pro Val Arg Val
                 80                  85                  90 tac agc ctt cct ggt cga gag aac tac tcc tcg gta gat gcc aac ggc      398
Tyr Ser Leu Pro Gly Arg Glu Asn Tyr Ser Ser Val Asp Ala Asn Gly
 95                 100                 105                 110 atc cag tct cag atg ctt tcc cga tgg tcc gcg tcc ttc gct gtg acc      446
Ile Gln Ser Gln Met Leu Ser Arg Trp Ser Ala Ser Phe Ala Val Thr
                115                 120                 125 aaa ggc aaa agc agt acc cag gaa gcc aca gga cgg gca gtg tcc aca      494
Lys Gly Lys Ser Ser Thr Gln Glu Ala Thr Gly Arg Ala Val Ser Thr
            130                 135                 140 gcc cac cca cct tca ggt aaa aga cta aag aag aca cca gag aag aag      542
Ala His Pro Pro Ser Gly Lys Arg Leu Lys Lys Thr Pro Glu Lys Lys
            145                 150                 155 act ggc aac aaa gac tgt aag gca gac att gca ttt ctc att gat gga      590
Thr Gly Asn Lys Asp Cys Lys Ala Asp Ile Ala Phe Leu Ile Asp Gly
160                 165                 170 agc ttc aat att ggg cag cgc cga ttt aat ttg cag aag aat ttt gtt      638
Ser Phe Asn Ile Gly Gln Arg Arg Phe Asn Leu Gln Lys Asn Phe Val
175                 180                 185                 190 ggg aaa gtg gca cta atg ttg gga att gga aca gaa gga cca cac gtg      686
Gly Lys Val Ala Leu Met Leu Gly Ile Gly Thr Glu Gly Pro His Val
                195                 200                 205
```

```
                                                          -continued ggt ctc gtt caa gcc agt gaa cac ccc aaa ata gaa ttt tac ttg aaa      734
Gly Leu Val Gln Ala Ser Glu His Pro Lys Ile Glu Phe Tyr Leu Lys
            210                 215                 220 aac ttt act tca gcc aaa gat gtc ttg ttt gcc ata aaa gaa gta ggt      782
Asn Phe Thr Ser Ala Lys Asp Val Leu Phe Ala Ile Lys Glu Val Gly
225                 230                 235 ttc cga ggg ggt aac tcc aac aca gga aaa gcc ttg aag cac act gct      830
Phe Arg Gly Gly Asn Ser Asn Thr Gly Lys Ala Leu Lys His Thr Ala
    240                 245                 250 cag aaa ttc ttt aca gca gac act ggt gtg aga aaa gga ata cca aaa      878
Gln Lys Phe Phe Thr Ala Asp Thr Gly Val Arg Lys Gly Ile Pro Lys
255                 260                 265                 270 gtg gtg gta gtg ttt att gat ggt tgg ccc tct gat gac att gag gaa      926
Val Val Val Val Phe Ile Asp Gly Trp Pro Ser Asp Asp Ile Glu Glu
                275                 280                 285 gca ggc att gtg gcc aga gag ttt ggt gtc aat gta ttt ata gtt tct      974
Ala Gly Ile Val Ala Arg Glu Phe Gly Val Asn Val Phe Ile Val Ser
            290                 295                 300 gtg gcc aag ccc att cct gaa gaa ctg ggg atg gtt caa gat gtt gca     1022
Val Ala Lys Pro Ile Pro Glu Glu Leu Gly Met Val Gln Asp Val Ala
305                 310                 315 ttt gtt gac aag gct gtg tgt cgg aat aat ggc ttc ttc tct tat cac     1070
Phe Val Asp Lys Ala Val Cys Arg Asn Asn Gly Phe Phe Ser Tyr His
    320                 325                 330 atg ccc aac tgg ttt ggc act aca aaa tat gtg aag cct ctg gtg cag     1118
Met Pro Asn Trp Phe Gly Thr Thr Lys Tyr Val Lys Pro Leu Val Gln
335                 340                 345                 350 aag ctc tgt acg cac gaa cag atg atg tgc agc aaa acc tgc tac aac     1166
Lys Leu Cys Thr His Glu Gln Met Met Cys Ser Lys Thr Cys Tyr Asn
                355                 360                 365 tca gtg aac att gcc ttt ctg att gac ggc tcc agc agt gtt gga gat     1214
Ser Val Asn Ile Ala Phe Leu Ile Asp Gly Ser Ser Ser Val Gly Asp
            370                 375                 380 agc aat ttc cgc ctc atg cta gaa ttt gtt tct aac ata gcg aag aca     1262
Ser Asn Phe Arg Leu Met Leu Glu Phe Val Ser Asn Ile Ala Lys Thr
385                 390                 395 ttt gaa atc tca gac att gga gcc aag ata gct gct gta cag ttc act     1310
Phe Glu Ile Ser Asp Ile Gly Ala Lys Ile Ala Ala Val Gln Phe Thr
    400                 405                 410 tat gac cag cgc acc gag ttc agt ttc act gac tat aat acc aaa gag     1358
Tyr Asp Gln Arg Thr Glu Phe Ser Phe Thr Asp Tyr Asn Thr Lys Glu
415                 420                 425                 430 aac gtc cta gct gtc cta gcg aac atc cgc tac atg agt ggt ggc aca     1406
Asn Val Leu Ala Val Leu Ala Asn Ile Arg Tyr Met Ser Gly Gly Thr
                435                 440                 445 gct act ggt gat gcc atc gcc ttt act gtt aga aat gta ttt ggt ccc     1454
Ala Thr Gly Asp Ala Ile Ala Phe Thr Val Arg Asn Val Phe Gly Pro
            450                 455                 460 ata agg gac agc ccc aac aaa aac ttc ctg gtt att gtc aca gat ggg     1502
Ile Arg Asp Ser Pro Asn Lys Asn Phe Leu Val Ile Val Thr Asp Gly
465                 470                 475 cag tcc tat gat gat gtc cga ggc cct gct gca gct gcc cat gat gca     1550
Gln Ser Tyr Asp Asp Val Arg Gly Pro Ala Ala Ala Ala His Asp Ala
    480                 485                 490 ggt atc acc atc ttc tct gtt ggt gtg gct tgg gca ccg ctg gat gac     1598
Gly Ile Thr Ile Phe Ser Val Gly Val Ala Trp Ala Pro Leu Asp Asp
495                 500                 505                 510 ctg aga gat atg gcc tct aaa ccc aaa gag tca cac gct ttc ttt acc     1646
Leu Arg Asp Met Ala Ser Lys Pro Lys Glu Ser His Ala Phe Phe Thr
                515                 520                 525
```

```
aga gag ttc aca ggg tta gaa cca att gtc tct gac gtc atc aga ggc     1694
Arg Glu Phe Thr Gly Leu Glu Pro Ile Val Ser Asp Val Ile Arg Gly
            530                 535                 540 att tgt aga gac ttc tta gaa tcc cag caa t aaccgatact ctgacaactc     1745
Ile Cys Arg Asp Phe Leu Glu Ser Gln Gln
            545                 550 aaggaatacg tgcaagggga tctaatgtgc aaattatatt ctcaatgcct atgtaacttt   1805
atagcttacc agtgtcaaaa aatgcgtcca cagctgttta aagcaaatga atattcatgt   1865
gatgctcaca atttagattg gccgagactt gataatcagg cccttagaaa ctcaggaaag   1925
aagagttgtc atggattaac attgggagtt caaatatgca ttcaagtgga taggtaagct   1985
acacagctca ataaaagaac ctggcgctta cacacaaagc actgttccct ctttaatcac   2045
tctgcattga ccatgcaagg aaaacagaac agcttttaaa cacagatcaa gtatacatat   2105
tttgacccat gtggatgttt tcttaaaacc agccaagaac agacagctgt tattatgtgc   2165
actagccata actacacatt atatggaatc atatatcaag cttcttttgt agtgtgtttt   2225
cataacttga tggctgaaat accacactga gtaaaggtag gattgcctgg tattttttcta  2285
tttatatcct taattttatg tgtatagaca ggcatgtact ccgaggacta agaaaatgtt   2345
taagcagata actttttttt tttgaaaaaa aagatgtgtc aagtattgta accgaaaaaa   2405
tacacagctt aatagcttgg ctgtcagcaa taaaactgct agtgactaag              2455

<210> SEQ ID NO 7
<211> LENGTH: 552
<212> TYPE: PRT
<213> ORGANISM: Mus musculus

<400> SEQUENCE: 7

Met Pro Ser Ser Arg Ile Pro Ala Leu Cys Leu Gly Ala Trp Leu Leu
 1               5                  10                  15

Leu Leu Leu Leu Pro Arg Phe Ala Arg Ala Glu Gly Ala Val Pro Ile
            20                  25                  30

Pro Val Thr Cys Phe Thr Arg Gly Leu Asp Ile Arg Lys Glu Lys Ala
        35                  40                  45

Asp Val Leu Cys Pro Gly Gly Cys Ser Leu Glu Glu Phe Ser Val Phe
    50                  55                  60

Gly Asn Ile Val Tyr Ala Ser Val Ser Ser Ile Cys Gly Ala Ala Val
 65                  70                  75                  80

His Arg Gly Val Ile Gly Thr Ser Gly Gly Pro Val Arg Val Tyr Ser
                85                  90                  95

Leu Pro Gly Arg Glu Asn Tyr Ser Ser Val Asp Ala Asn Gly Ile Gln
            100                 105                 110

Ser Gln Met Leu Ser Arg Trp Ser Ala Ser Phe Ala Val Thr Lys Gly
        115                 120                 125

Lys Ser Ser Thr Gln Glu Ala Thr Gly Arg Ala Val Ser Thr Ala His
    130                 135                 140

Pro Pro Ser Gly Lys Arg Leu Lys Lys Thr Pro Glu Lys Lys Thr Gly
145                 150                 155                 160

Asn Lys Asp Cys Lys Ala Asp Ile Ala Phe Leu Ile Asp Gly Ser Phe
                165                 170                 175

Asn Ile Gly Gln Arg Arg Phe Asn Leu Gln Lys Asn Phe Val Gly Lys
            180                 185                 190

Val Ala Leu Met Leu Gly Ile Gly Thr Glu Gly Pro His Val Gly Leu
        195                 200                 205
```

```
Val Gln Ala Ser Glu His Pro Lys Ile Glu Phe Tyr Leu Lys Asn Phe
    210                 215                 220

Thr Ser Ala Lys Asp Val Leu Phe Ala Ile Lys Glu Val Gly Phe Arg
225                 230                 235                 240

Gly Gly Asn Ser Asn Thr Gly Lys Ala Leu Lys His Thr Ala Gln Lys
                245                 250                 255

Phe Phe Thr Ala Asp Thr Gly Val Arg Lys Gly Ile Pro Lys Val Val
                260                 265                 270

Val Val Phe Ile Asp Gly Trp Pro Ser Asp Ile Glu Glu Ala Gly
            275                 280                 285

Ile Val Ala Arg Glu Phe Gly Val Asn Val Phe Ile Val Ser Val Ala
    290                 295                 300

Lys Pro Ile Pro Glu Glu Leu Gly Met Val Gln Asp Val Ala Phe Val
305                 310                 315                 320

Asp Lys Ala Val Cys Arg Asn Asn Gly Phe Phe Ser Tyr His Met Pro
                325                 330                 335

Asn Trp Phe Gly Thr Thr Lys Tyr Val Lys Pro Leu Val Gln Lys Leu
                340                 345                 350

Cys Thr His Glu Gln Met Met Cys Ser Lys Thr Cys Tyr Asn Ser Val
            355                 360                 365

Asn Ile Ala Phe Leu Ile Asp Gly Ser Ser Val Gly Asp Ser Asn
370                 375                 380

Phe Arg Leu Met Leu Glu Phe Val Ser Asn Ile Ala Lys Thr Phe Glu
385                 390                 395                 400

Ile Ser Asp Ile Gly Ala Lys Ile Ala Ala Val Gln Phe Thr Tyr Asp
                405                 410                 415

Gln Arg Thr Glu Phe Ser Phe Thr Asp Tyr Asn Thr Lys Glu Asn Val
                420                 425                 430

Leu Ala Val Leu Ala Asn Ile Arg Tyr Met Ser Gly Gly Thr Ala Thr
            435                 440                 445

Gly Asp Ala Ile Ala Phe Thr Val Arg Asn Val Phe Gly Pro Ile Arg
    450                 455                 460

Asp Ser Pro Asn Lys Asn Phe Leu Val Ile Val Thr Asp Gly Gln Ser
465                 470                 475                 480

Tyr Asp Asp Val Arg Gly Pro Ala Ala Ala His Asp Ala Gly Ile
                485                 490                 495

Thr Ile Phe Ser Val Gly Val Ala Trp Ala Pro Leu Asp Asp Leu Arg
            500                 505                 510

Asp Met Ala Ser Lys Pro Lys Glu Ser His Ala Phe Phe Thr Arg Glu
    515                 520                 525

Phe Thr Gly Leu Glu Pro Ile Val Ser Asp Val Ile Arg Gly Ile Cys
    530                 535                 540

Arg Asp Phe Leu Glu Ser Gln Gln
545                 550

<210> SEQ ID NO 8
<211> LENGTH: 149
<212> TYPE: PRT
<213> ORGANISM: Homo sapiens

<400> SEQUENCE: 8

Asp Leu Val Phe Leu Val Asp Gly Ser Trp Ser Val Gly Arg Asn Asn
 1               5                  10                  15

Phe Lys Tyr Ile Leu Asp Phe Ile Ala Ala Leu Val Ser Ala Phe Asp
            20                  25                  30
```

```
Ile Gly Glu Glu Lys Thr Arg Val Gly Val Val Gln Tyr Ser Ser Asp
        35                  40                  45

Thr Arg Thr Glu Phe Asn Leu Asn Gln Tyr Tyr Gln Arg Asp Glu Leu
 50                  55                  60

Leu Ala Ala Ile Lys Lys Ile Pro Tyr Lys Gly Gly Asn Thr Met Thr
 65                  70                  75                  80

Asp Ala Ile Asp Tyr Leu Val Lys Asn Thr Phe Thr Glu Ser Ala Gly
                 85                  90                  95

Ala Arg Val Gly Phe Pro Lys Val Ala Ile Ile Thr Asp Gly Lys
                100                 105                 110

Ser Gln Asp Glu Val Glu Ile Pro Ala Arg Glu Leu Arg Asn Val Gly
            115                 120                 125

Val Glu Val Phe Ser Leu Gly Ile Lys Ala Ala Asp Ala Lys Glu Leu
        130                 135                 140

Lys Gln Ile Ala Ser
145

<210> SEQ ID NO 9
<211> LENGTH: 145
<212> TYPE: PRT
<213> ORGANISM: Homo sapiens

<400> SEQUENCE: 9

Asp Leu Val Phe Leu Ile Asp Gly Ser Lys Ser Val Arg Pro Glu Asn
 1               5                  10                  15

Phe Glu Leu Val Lys Lys Phe Glu Ser Gln Ile Val Asp Thr Leu Asp
             20                  25                  30

Val Ser Asp Lys Leu Ala Gln Val Gly Leu Val Gln Tyr Ser Ser Ser
         35                  40                  45

Val Arg Gln Glu Phe Pro Leu Gly Arg Phe His Thr Lys Lys Asp Ile
     50                  55                  60

Lys Ala Ala Val Arg Asn Met Ser Tyr Met Glu Lys Gly Thr Met Thr
 65                  70                  75                  80

Gly Ala Ala Leu Lys Tyr Leu Ile Asp Asn Ser Phe Thr Val Ser Ser
                 85                  90                  95

Gly Ala Arg Pro Gly Ala Gln Lys Val Gly Ile Val Phe Thr Asp Gly
                100                 105                 110

Arg Ser Gln Asp Tyr Ile Asn Asp Ala Ala Lys Lys Ala Lys Asp Leu
            115                 120                 125

Gly Phe Lys Met Phe Ala Val Gly Val Gly Asn Ala Val Glu Asp Glu
        130                 135                 140

Leu
145

<210> SEQ ID NO 10
<211> LENGTH: 137
<212> TYPE: PRT
<213> ORGANISM: Homo sapiens

<400> SEQUENCE: 10

Asp Val Ile Leu Leu Leu Asp Gly Ser Ser Ser Phe Pro Ala Ser Tyr
 1               5                  10                  15

Phe Asp Glu Met Lys Ser Phe Ala Lys Ala Phe Ile Ser Lys Ala Asn
             20                  25                  30
```

-continued

```
Ile Gly Pro Arg Leu Thr Gln Val Ser Val Leu Gln Tyr Gly Ser Ile
         35                  40                  45

Thr Thr Ile Asp Val Pro Trp Asn Val Val Pro Glu Lys Ala His Leu
     50                  55                  60

Leu Ser Leu Val Asp Val Asn Gln Arg Glu Gly Gly Pro Ser Gln Ile
 65                  70                  75                  80

Gly Asp Ala Leu Gly Phe Ala Val Arg Tyr Leu Thr Ser Glu Met His
                 85                  90                  95

Gly Ala Arg Pro Gly Ala Ser Lys Ala Val Val Ile Leu Val Thr Asp
            100                 105                 110

Val Ser Val Asp Ser Val Asp Ala Ala Asp Ala Ala Arg Ser Asn
        115                 120                 125

Arg Val Thr Val Phe Pro Ile Gly Ile
    130                 135
```

<210> SEQ ID NO 11
<211> LENGTH: 105
<212> TYPE: PRT
<213> ORGANISM: Homo sapiens

<400> SEQUENCE: 11

```
Ile Thr Cys Phe Thr Arg Gly Leu Asp Ile Arg Lys Glu Lys Ala Asp
  1               5                  10                  15

Val Leu Cys Pro Gly Gly Cys Pro Leu Glu Glu Phe Ser Val Tyr Gly
                 20                  25                  30

Asn Ile Val Tyr Ala Ser Val Ser Ile Cys Gly Ala Ala Val His
             35                  40                  45

Arg Gly Val Ile Ser Asn Ser Gly Pro Val Arg Val Tyr Ser Leu
     50                  55                  60

Pro Gly Arg Glu Asn Tyr Ser Ser Val Asp Ala Asn Gly Ile Gln Ser
 65                  70                  75                  80

Gln Met Leu Ser Arg Trp Ser Ala Ser Phe Thr Val Thr Lys Gly Lys
                 85                  90                  95

Ser Ser Thr Gln Glu Ala Thr Gly Gln
            100                 105
```

<210> SEQ ID NO 12
<211> LENGTH: 20
<212> TYPE: DNA
<213> ORGANISM: Unknown
<220> FEATURE:
<223> OTHER INFORMATION: probe

<400> SEQUENCE: 12
gattgtaaag cagacattgc                                                20

<210> SEQ ID NO 13
<211> LENGTH: 17
<212> TYPE: DNA
<213> ORGANISM: Unknown
<220> FEATURE:
<223> OTHER INFORMATION: probe

<400> SEQUENCE: 13
acctacttcc ttatggc                                                   17

```
<210> SEQ ID NO 14
<211> LENGTH: 20
<212> TYPE: DNA
<213> ORGANISM: Unknown
<220> FEATURE:
<223> OTHER INFORMATION: probe

<400> SEQUENCE: 14
gggcagtcct atgatgatgt                                                    20

<210> SEQ ID NO 15
<211> LENGTH: 20
<212> TYPE: DNA
<213> ORGANISM: Unknown
<220> FEATURE:
<223> OTHER INFORMATION: probe

<400> SEQUENCE: 15
gctatggaat ttgcatatct                                                    20

<210> SEQ ID NO 16
<211> LENGTH: 20
<212> TYPE: DNA
<213> ORGANISM: Unknown
<220> FEATURE:
<223> OTHER INFORMATION: primer

<400> SEQUENCE: 16
catcagaggc agcatttgta                                                    20

<210> SEQ ID NO 17
<211> LENGTH: 18
<212> TYPE: DNA
<213> ORGANISM: Unknown
<220> FEATURE:
<223> OTHER INFORMATION: primer

<400> SEQUENCE: 17
ttgtaaccag aaggcagc                                                      18

<210> SEQ ID NO 18
<211> LENGTH: 14
<212> TYPE: DNA
<213> ORGANISM: Unknown
<220> FEATURE:
<223> OTHER INFORMATION: probe

<400> SEQUENCE: 18
aacatagtat atgc                                                          14

<210> SEQ ID NO 19
<211> LENGTH: 14
<212> TYPE: DNA
<213> ORGANISM: Unknown
<220> FEATURE:
<223> OTHER INFORMATION: probe

<400> SEQUENCE: 19
ttctagacgg tctg                                                          14
```

COMPOSITIONS TO DETECT LESIONS ASSOCIATED WITH HEARING LOSS IN THE COCHLEAR GENE, COCH5B2

This application claims the benefit of a previously filed Provisional Application No. 60/102,343, filed Sep. 29, 1998, the contents of which is incorporated in its entirety.

BACKGROUND OF THE INVENTION

Hearing loss is a heterogeneous disorder that affects over 14 million people in the United States, with approximately 1 of every 1000 infants being affected by congenital deafness. An estimated one-half of congenital hearing loss cases are due to genetic causes (Bieber and Nance (1979) *Clinical Genetics-A Sourcebook for Physicians*, Jackson and Schimke, eds., Wiley, NY, vol. 60, pp. 443–461). More than 175 different forms of hereditary deafness have been characterized, including autosomal dominant, autosomal recessive, X-linked, and mitochondrial forms (McKusick (1994) *Mendelian Inheritance in Man*, John Hopkins Univ. Press, Baltimore, Md.).

Genetic heterogeneity in hearing disorders both associated with other clinical anomalies (syndromic) and occurring as an isolated finding (nonsyndromic) indicates the involvement of a large number of genes in the complex development and function of the hearing process. Of the several hundred syndromic hearing loss disorders described (Gorlin et al. (1995) *Hereditary Hearing Loss and Its Syndromes*, Oxford Univ. Press, New York, N.Y.), only about 60 have been mapped to human chromosomes, with approximately half of these with characterized gene defects (Duyk et al., *Nature Genet.* 2:5–8, 1992; Petit, *Nature Genet.* 14:385–391, 1996). The majority of congenital hearing disorders are nonsyndromic (Cohen and Gorlin (1995) *Hereditary Hearing Loss and its Syndromes*, Gorlin, Toriello and Cohen, eds., Oxford Univ. Press, New York, N.Y., vol. 60, pp. 9–21), but even fewer nonsyndromic disorders have been identified. This number is increasing through the study of consanguineous geographically isolated families. Over 40 human chromosomal loci associated with nonsyndromic hearing impairment have been identified, some with corresponding mouse mutants in the homologous region (Petit (1996), supra; Van Camp et al., *Am. J. Hum. Genet.* 60:758–764, 1997). However, to date, only a small number of nuclear genes responsible for nonsyndromic hearing impairment have been discovered: POU3F4 in DFN3 (de Kok et al. *Science* 267:685–688, 1995); MYO7A in DFNB2 (Liu et al., *Nature Genet.* 16:188–190, 1997; Weil et al. *Nature Genet.* 16:191–193, 1997) and DFN11 (Liu et al., *Nature Genet.* 17:268, 1997); POU4F3 in DFNA15 (Vahava et al., *Science* 279:1950, 1998); PDS in DFNB4 (Li et al., *Nature Genet.* 18:215, 1998); TECTA in both DFNA8 and DFNA11 (Verhoeven et al., *Nature Genet.* 19:60, 1998); and GJB2 in DFNB1 and DFNA3 (Kelsell et al., *Nature* 387: 80–83, 1997).

Thus a need still exists to identify novel human genes responsible for hearing defects.

SUMMARY OF THE INVENTION

The invention is based, in part, on the discovery of a nucleic acid and corresponding protein molecule, referred to herein as COCH5B2 ("COCH5B2") molecules. The COCH5B2 molecules of the present invention are useful in diagnosing and treating hearing disorders, e.g., human nonsyndromic sensorineural deafness with vestibular involvement (DFNA9).

Accordingly, in one aspect, the invention features an isolated nucleic acid molecule (e.g., cDNAs) comprising a nucleotide sequence encoding a COCH5B2 protein or a biologically active portion thereof, as well as nucleic acid fragments suitable as primers or hybridization probes for the detection of COCH5B2-encoding nucleic acid (e.g., mRNA). In particularly preferred embodiments, the isolated nucleic acid molecule includes the nucleotide sequence of SEQ ID NO:1, SEQ ID NO:6, or the coding region or a complement of these nucleotide sequences. In other particularly preferred embodiments, the isolated nucleic acid molecule of the invention includes a nucleotide sequence which hybridizes to or has at least about 60–65%, preferably at least about 70–75%, more preferably at least about 80–85%, and even more preferably at least about 90–95%, 96%, 97%, 98% or 99% sequence identity to the nucleotide sequence shown in SEQ ID NO: 1, SEQ ID NO:6, or a portion thereof. In other preferred embodiments, the isolated nucleic acid molecule encodes the amino acid sequence of SEQ ID NO:2 or SEQ ID NO:7. The preferred COCH5B2 nucleic acid encodes a protein which also preferably possesses at least one of the COCH5B2 activities described herein.

In another embodiment, the isolated nucleic acid molecule encodes a protein or portion thereof wherein the protein or portion thereof includes an amino acid sequence which is sufficiently homologous to an amino acid sequence of SEQ ID NO:2 or SEQ ID NO:7, e.g., sufficiently homologous to an amino acid sequence of SEQ ID NO:2 or SEQ ID NO:7 such that the protein or portion thereof maintains a COCH5B2 activity. Preferably, the protein or portion thereof encoded by the nucleic acid molecule maintains the ability to play a role in inner ear biology. In one embodiment, the protein encoded by the nucleic acid molecule has at least about 60–70%, preferably at least about 80–85%, and more preferably at least about 86, 88, 90%, and most preferably at least about 90–95%, 96%, 97%, 98% or 99% sequence identity to the amino acid sequence of SEQ ID NO:2 (e.g., the entire amino acid sequence of SEQ ID NO:2) or SEQ ID NO:7. In another preferred embodiment, the protein is a full length human protein which is substantially homologous to the entire amino acid sequence of SEQ ID NO:2 (encoded by the open reading frame shown in SEQ ID NO:3).

In yet another embodiment, the isolated nucleic acid molecule is derived from a human and encodes a portion of a protein which includes at least one or two von Willebrand factor (vWF) type A-like domains. Preferably, the vWF type A-like domain encoded by the human nucleic acid molecule has at least about 75%, preferably at least about 80–85%, and most preferably at least about 80–90% or more sequence identity to the vWF type A-like domain (i.e., about amino acid residues 165 to 309 and about amino acid residues 366 to 514) of SEQ ID NO:2 which are shown as separate sequences designated SEQ ID NO:4 and SEQ ID NO: 5, respectively. In stPill another embodiment, the nucleic acid molecule is a nonmammalian molecule which encodes at least one or two vWF type A-like domains. Preferably, the vWF type A-like domain encoded by the nonmammalian nucleic acid has at least about 55%, more preferably at least about 60–65%, even more preferably at least about 70%–75% and most preferably at least about 80–950% or more sequence identity to SEQ ID NO:4 or SEQ ID NO:5.

In yet another embodiment, the isolated nucleic acid molecule is derived from a human and encodes a portion of a protein which includes at least one factor C homologous domain. Preferably, the factor C homologous domain encoded by the human nucleic acid molecule has at least about 75%, preferably at least about 80–85%, and most preferably at least about 80–90% or more sequence identity to the factor C homologous domain (i.e., about amino acid residues 32–136) of SEQ ID NO:2 which is shown as a separate sequence designated SEQ ID NO: 1. In still another embodiment, the nucleic acid molecule is a nonmammalian molecule which encodes at least one factor C homologous domain. Preferably, the factor C homologous domain encoded by the nonmammalian nucleic acid has at least about 55%, more preferably at least about 60–65%, even more preferably at least about 70%–75% and most preferably at least about 80–950% or more sequence identity to SEQ ID NO: 11.

In another preferred embodiment, the isolated nucleic acid molecule is derived from a human and encodes a protein (e.g., a COCH5B2 fusion protein) which includes a vWF type A-like domain which has at least about 55% or more sequence identity to SEQ ID NO:4 and/or SEQ ID NO:5 and has one or more of the following activities involved with inner ear biology:

1) it can interact, e.g., bind, with components of extracellular matrix (e.g., fibrillar collagen, e.g., COL1A2, COL3A1); 2) it can modulate cell/extracellular matrix interactions; 3) it can modulate cell—cell adhesions; 4) it can interact, e.g., bind, with glycoproteins and/or proteoglycans for clearing them; 5) it can provide scaffolding by interacting with other extracellular matrix components (e.g., fibrillar collagen, e.g., COL1A2, COL3A1); and 6) it can modulate an inner ear secretory pathway (e.g., it can modulate production of acidophillic deposits).

In another embodiment, the isolated nucleic acid molecule is at least 15 nucleotides in length and hybridizes under stringent conditions to a nucleic acid molecule comprising the nucleotide sequence of SEQ ID NO: 1 or SEQ ID NO:6. Preferably, the isolated nucleic acid molecule corresponds to a naturally-occurring nucleic acid molecule. More preferably, the isolated nucleic acid encodes naturally-occurring human COCH5B2 or a biologically active portion thereof. Preferably, the biologically active portion is preferably encoded by a nucleotide sequence greater than 200 base pairs in length and/or excludes nucleotides 1457–1654. In yet another preferred embodiment, the biologically active portion is preferably encoded by a nucleotide sequence greater than 400, 500 or 600 base pairs in length, e.g., it is at least 700 or 1000 base pairs in length. Moreover, given the disclosure herein of COCH5B2-encoding cDNA sequences (e.g., SEQ ID NO: 1 and SEQ ID NO:6), antisense nucleic acid molecules (i.e., molecules which are complementary to the coding strand of the COCH5B2 cDNA sequence) are also provided by the invention.

In a preferred embodiment, the encoded COCH5B2 protein differs in amino acid sequence at 1, 2, 3, 5, 10 or more residues, from a sequence in SEQ ID NO:2 or SEQ ID NO:7. The differences, however, are such that: the COCH5B2 encoded protein exhibits a COCH5B2 biological activity, e.g., the encoded COCH5B2 protein retains a biological activity of a naturally occurring COCH5B2, e.g., the COCH5B2 protein of SEQ ID NO:2 or SEQ ID NO:7.

In preferred embodiments, the encoded polypeptide includes all or a fragment of an amino acid sequence from SEQ ID NO:2 or SEQ ID NO:7, fused, in reading frame, to additional amino acid residues, preferably to residues encoded by genomic DNA 5' to the genomic DNA which encodes a sequence from SEQ ID NO:2 or SEQ ID NO:7.

In preferred embodiments the encoded COCH5B2 protein includes a COCH5B2 sequence described herein as well as other N-terminal and/or C-terminal amino acid sequence.

In another aspect, the invention features vectors, e.g., recombinant expression vectors, containing the nucleic acid molecules of the invention and host cells into which such vectors have been introduced. In one embodiment, such a host cell is used to produce COCH5B2 protein by culturing the host cell in a suitable medium. The COCH5B2 protein can be then isolated from the medium or the host cell.

In yet another aspect, the invention features transgenic nonhuman animals in which a COCH5B2 gene has been introduced or altered. In one embodiment, the genome of the nonhuman animal has been altered by introduction of a nucleic acid molecule of the invention encoding COCH5B2 as a transgene. In another embodiment, an endogenous COCH5B2 gene within the genome of the nonhuman animal has been altered, e.g., functionally disrupted, by homologous recombination.

In still another aspect, the invention features an isolated COCH5B2 protein or a portion, e.g., a biologically active portion, thereof. In a preferred embodiment, the isolated COCH5B2 protein or portion thereof plays a role in inner ear biology. In another preferred embodiment, the isolated COCH5B2 protein or portion thereof is sufficiently homologous to an amino acid sequence of SEQ ID NO:2 or SEQ ID NO:7 such that the protein or portion thereof maintains one or more COCH5B2 activities.

In one embodiment, the biologically active portion of the COCH5B2 protein includes a domain or motif, preferably a domain or motif which has a COCH5B2 activity. The domain can be, e.g., a vWF type A-like domain. If the active portion of the protein which includes one or two vWF type A-like domains is isolated or derived from a human, it is preferred that the vWF type A-like domain have at least about 75%, preferably at least about 80–85%, and most preferably about 90–95%, 96%, 97%, 98% or 99% sequence identity to SEQ ID NO:4 and/or SEQ ID NO:5. If the active portion of the protein which includes the vWF type A-like domain is isolated or derived from an animal which is not a mammal, it is preferred that the vWF type A-like domain have at least about 55%, preferably at least about 60–65%, even more preferably at least about 70%–75% and most preferably at least about 80–90% 90–95% 96%, 97%, 98% or 99% sequence identity to SEQ ID NO:4 and/or SEQ ID NO:5. The domain can also be, e.g., a factor C homologous domain. If the active portion of the protein which includes one factor C homologous domain is isolated or derived from a human, it is preferred that the factor C homologous domain have at least about 75%, preferably at least about 80–85%, and most preferably about 90–95%, 96%, 97%, 98% or 99% sequence identity to SEQ ID NO: 11. If the active portion of the protein which includes the factor C homologous domain is isolated or derived from an animal which is not a mammal, it is preferred that the factor C homologous domain have at least about 55%, preferably at least about 60–65%, even more preferably at least about 70%–75% and most preferably at least about 80–90% 90–95% 96%, 97%, 98% or 99% sequence identity to SEQ ID NO:11. Preferably, the biologically active portion of the COCH5B21 protein which includes one or two domains also has one of the following activities: 1) it can interact, e.g., bind, with components of extracellular matrix (e.g., fibrillar collagen, e.g., COL1A2, COL3A1); 2) it can modulate cell/extracellular matrix interactions; 3) it can modulate cell—cell adhesions; 4) it can interact, e.g., bind, with glycoproteins and/or proteoglycans for clearing them; 5) it can provide scaffolding by interacting with other extracellular matrix components (e.g., fibrillar collagen, e.g., COL1A2, COL3A1); and 6) it can modulate an inner ear secretory pathway (e.g., it can modulate production of acidophillic deposits).

The invention also provides an isolated preparation of a COCH5B2 protein. In preferred embodiments, the COCH5B2 protein includes the amino acid sequence of SEQ ID NO:2 or SEQ ID NO:7. In another preferred embodiment, the invention pertains to an isolated full length protein which is substantially homologous to the entire amino acid sequence of SEQ ID NO:2 (encoded by the open reading frame shown in SEQ ID NO:3) or SEQ ID NO:7. In yet another embodiment, the protein has at least about 60–70%, preferably at least about 80–85%, and more preferably at least about 86, 88, 90%, and most preferably at least about 90–95%96%, 97%, 98% or 99% sequence identity to the entire amino acid sequence of SEQ ID NO:2 or SEQ ID NO:7. In other embodiments, the isolated COCH5B2 protein includes an amino acid sequence which has at least about 60–70% or more sequence identity to the amino acid sequence of SEQ ID NO:2 or SEQ ID NO:7 and has an one or more of the following activities: 1) it can interact, e.g., bind, with components of extracellular matrix (e.g., fibrillar collagen, e.g., COL1A2, COL3A1); 2) it can modulate cell/extracellular matrix interactions; 3) it can modulate cell—cell adhesions; 4) it can interact, e.g., bind, with glycoproteins and/or proteoglycans for clearing them; 5) it can provide scaffolding by interacting with other extracellular matrix components (e.g., fibrillar collagen, e.g., COL1A2, COL3A1); and 6) it can modulate an inner ear secretory pathway (e.g., it can modulate production of acidophillic deposits).

Alternatively, the isolated COCH5B2 protein can include an amino acid sequence which is encoded by a nucleotide sequence which hybridizes, e.g., hybridizes under stringent conditions, or has at least about 60–65%, preferably at least about 70–75%, more preferably at least about 80–85%, and even more preferably at least about 90–95%96%, 97%, 98% or 99% sequence identity to the nucleotide sequence of SEQ ID NO: 1 or SEQ ID NO:6. It is also preferred that the preferred forms of COCH5B2 also have one or more of the COCH5B2 activities described herein.

In a preferred embodiment, the COCH5B2 protein differs in amino acid sequence at up to 1, 2, 3, 5, or 10 residues, from a sequence in SEQ ID NO: 2 or SEQ ID NO:7. In other preferred embodiments, the COCH5B2 protein differs in amino acid sequence at up to 1, 2, 3, 5, or 10% of the residues from a sequence in SEQ ID NO: 2 or SEQ ID NO:7. Preferably, the differences are such that: the COCH5B2 protein exhibits a COCH5B2 biological activity, e.g., the COCH5B2 protein retains a biological activity of a naturally occurring COCH5B2.

In preferred embodiments, the COCH5B2 polypeptide includes a COCH5B2 sequence described herein as well as other N-terminal, and/or a C-terminal amino acid sequence.

The COCH5B2 protein (or polypeptide) or a biologically active portion thereof can be operatively linked to a non-COCH5B2 polypeptide to form a fusion protein. The COCH5B2 protein or a biologically active portion thereof can be incorporated into a pharmaceutical composition comprising the protein and a pharmaceutically acceptable carrier.

The COCH5B2 protein of the invention, or portions or fragments thereof, can be used to prepare anti-COCH5B2 antibodies. Accordingly, the invention also provides an antigenic peptide of COCH5B2 which includes at least 8 amino acid residues of the amino acid sequence shown in SEQ ID NO:2 or SEQ ID NO:7 and encompasses an epitope of COCH5B2 such that an antibody raised against the peptide forms a specific immune complex with COCH5B2. Preferably, the antigenic peptide includes at least 10 amino acid residues, more preferably at least 15 amino acid residues, even more preferably at least 20 amino acid residues, and most preferably at least 30, 50, 70, 80 amino acid residues. The invention further provides an antibody that specifically binds COCH5B2. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier.

Another aspect of the invention features methods for modulating a cell associated activity, e.g., cell—cell adhesion, e.g., in vitro or in vivo. Such methods include contacting the cell with an agent which modulates COCH5B2 protein activity or nucleic acid expression such that a cell associated activity is altered relative to a cell associated activity (e.g., the same cell associated activity) of the cell in the absence of the agent. The agent which modulates COCH5B2 activity can be an agent which stimulates COCH5B2 protein activity or COCH5B2 nucleic acid expression. Examples of agents which stimulate COCH5B2 protein activity or COCH5B2 nucleic acid expression include small molecules, active COCH5B2 proteins, and nucleic acids encoding COCH5B2 that have been introduced into the cell. Examples of agents which inhibit COCH5B2 activity or expression include small molecules, antisense COCH5B2 nucleic acid molecules, and antibodies that specifically bind to COCH5B2. In a preferred embodiment, the cell is present within a subject and the agent is administered to the subject.

The present invention also features methods for treating subjects having a hearing disorder. For example, the invention pertains to methods for treating a subject having a disorder characterized by aberrant COCH5B2 protein activity or nucleic acid expression such as a hearing disorder, e.g., a nonsyndromic sensorineural deafness with vestibular involvement (DFNA9). These methods include administering to the subject a COCH5B2 modulator (e.g., a small molecule) such that treatment of the subject occurs.

In other embodiments, the invention pertains to methods for treating a subject having a hearing disorder, e.g., a nonsyndromic sensorineural deafness with vestibular involvement (DFNA9), comprising administering to the subject a COCH5B2 protein or portion thereof such that treatment occurs. Hearing disorders can also be treated according to the invention by administering to the subject having the disorder a nucleic acid encoding a COCH5B2 protein or portion thereof such that treatment occurs.

The invention also features methods for detecting genetic lesions in a COCH5B2 gene, thereby determining if a subject with the lesioned gene is at risk for (or is predisposed to have) a disorder characterized by aberrant or abnormal COCH5B2 nucleic acid expression or COCH5B2 protein activity, e.g., a hearing disorder, e.g., DFNA9. In preferred embodiments, the methods include detecting, in a sample of cells from the subject, the presence or absence of a genetic lesion characterized by an alteration affecting the integrity of the gene encoding a COCH5B2 protein, or the misexpression of the COCH5B2 gene. Genetic lesions can be detected, e.g., by contacting the sample with a nucleic acid probe capable of hybridizing to COCH5B2 mRNA, e.g., a labeled probe, or an antibody capable of binding to COCH5B2 protein, e.g., a labeled antibody. In a preferred embodiment, the method can also be used in fetal or neonatal diagnosis.

Another aspect of the invention features methods for detecting the presence of COCH5B2 nucleic acid or protein in a biological sample. In a preferred embodiment, the methods involve contacting a biological sample (e.g., a cell sample) with a compound or an agent capable of detecting COCH5B2 protein or COCH5B2 nucleic acid, e.g., mRNA, such that the presence of COCH5B2 nucleic acid or protein is detected in the biological sample. The compound or agent can be, for example, a labeled or labelable nucleic acid probe capable of hybridizing to COCH5B2 mRNA or a labeled or labelable antibody capable of binding to COCH5B2 protein. The invention further provides methods for diagnosis of a subject with, for example, a hearing disorder, e.g., DFNA9, based on detection of COCH5B2 protein or mRNA. In one embodiment, the method involves contacting a cell or tissue sample (e.g., a biopsy sample) from the subject with an agent capable of detecting COCH5B2 protein or mRNA, determining the amount of COCH5B2 protein or mRNA expressed in the cell or tissue sample, comparing the amount of COCH5B2 protein or mRNA expressed in the cell or tissue sample to a control sample and forming a diagnosis based on the amount of COCH5B2 protein or mRNA expressed in the cell or tissue sample as compared to the control sample. Specific diagnostic tests are described in greater detail below. Kits for detecting COCH5B2 nucleic acid or protein in a biological sample are also within the scope of the invention and are described in greater detail below.

Still another aspect of the invention features methods, e.g., screening assays, for identifying a compound for treating a disorder characterized by aberrant COCH5B2 nucleic acid expression or protein activity, e.g., a hearing disorder, e.g., DNA9. These methods typically include assaying the ability of the compound or agent to modulate the expression of the COCH5B2 gene or the activity of the COCH5B2 protein thereby identifying a compound for treating a disorder characterized by aberrant COCH5B2 nucleic acid expression or protein activity. In a preferred embodiment, the method involves contacting a biological sample, e.g., a cell or tissue sample, obtained from a subject having the disorder with the compound or agent, determining the amount of COCH5B2 protein expressed and/or measuring the activity of the COCH5B2 protein in the biological sample, comparing the amount of COCH5B2 protein expressed in the biological sample and/or the measurable COCH5B2 biological activity in the cell to that of a control sample. An alteration in the amount of COCH5B2 protein expression or COCH5B2 activity in the cell exposed to the compound or agent in comparison to the control is indicative of a modulation of COCH5B2 expression and/or COCH5B2 activity.

The invention also pertains to methods for identifying a compound or agent which interacts with (e.g., binds to) a COCH5B2 protein. These methods can include the steps of contacting the COCH5B2 protein with the compound or agent under conditions which allow binding of the compound to the COCH5B2 protein to form a complex and detecting the formation of a complex of the COCH5B2 protein and the compound in which the ability of the compound to bind to the COCH5B2 protein is indicated by the presence of the compound in the complex.

The invention further pertains to methods for identifying a compound or agent which modulates, e.g., stimulates or inhibits, the interaction of the COCH5B2 protein with a target molecule, e.g., a component of the extracellular matrix, e.g., fibrillar collagens, or a protein involved in a secretory pathway, e.g., a protein involved in the secretion of acidophillic deposits. In these methods, the COCH5B2 protein is contacted, in the presence of the compound or agent, with the target molecule under conditions which allow binding of the target molecule to the COCH5B2 protein to form a complex. An alteration, e.g., an increase or decrease, in complex formation between the COCH5B2 protein and the target molecule as compared to the amount of complex formed in the absence of the compound or agent is indicative of the ability of the compound or agent to modulate the interaction of the COCH5B2 protein with a target molecule.

Other features and advantages of the invention will be apparent from the following detailed description and claims.

DETAILED DESCRIPTION OF THE DRAWINGS

FIG. 1 depicts the cDNA sequence and predicted amino acid sequence of human COCH5B2. The nucleotide sequence corresponds to nucleic acids 1 to 2534 of SEQ ID NO: 1. The amino acid sequence corresponds to amino acids 1 to 550 of SEQ ID NO:2.

FIG. 2 depicts the cDNA sequence and predicted amino acid sequence of murine COCH5B2. The nucleotide sequence corresponds to nucleic acids 1 to 2455 of SEQ ID NO:6. The amino acid sequence corresponds to amino acids 1 to 552 of SEQ ID NO:7.

FIG. 3 depicts an alignment of the amino acid sequences of human COCH5B2 (top row)(corresponding to amino acids 1 to 550 of SEQ ID NO:2) and murine COCH5B2 (bottom row)(corresponding to amino acids 1 to 552 of SEQ ID NO:7). The percent identity between human and murine COCH5B2 (i.e., 94% identity) is indicated by a dot on the bottom row and the percent amino acid similarity of human and murine COCH5B2 (i.e., 96%) is indicated by double and single dots between the two rows. Amino acids that differ in the murine sequence from the human are indicated on the bottom row.

Figure 4:
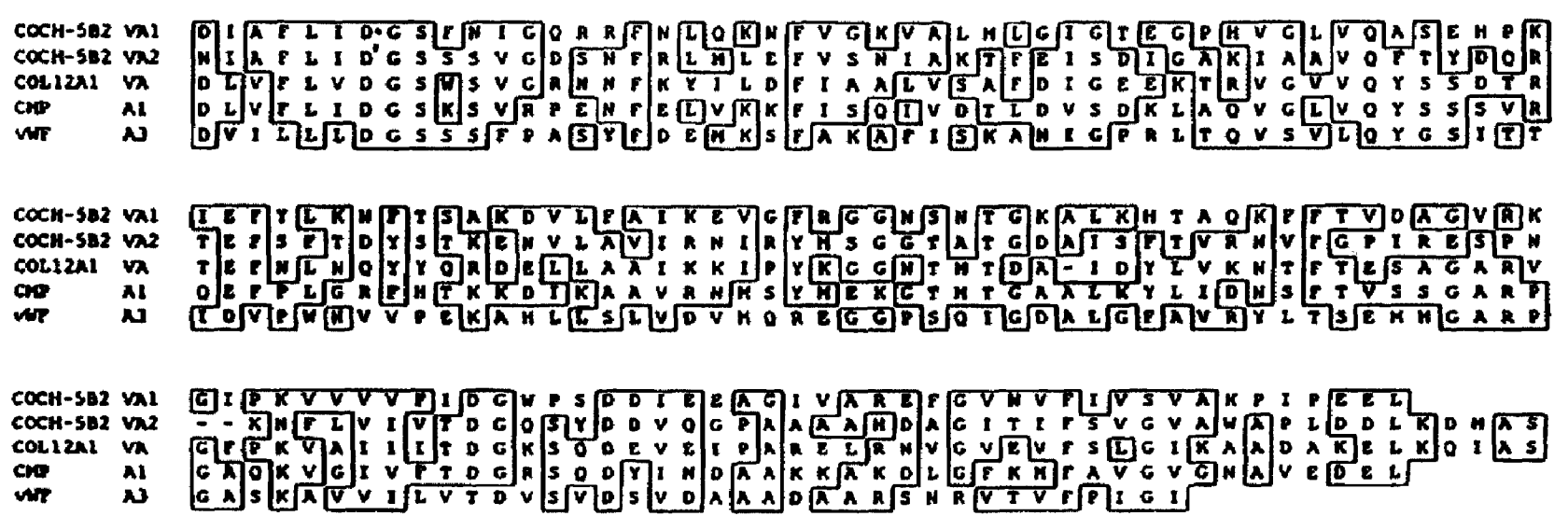

FIG. 4 depicts an alignment of the predicted amino acid sequences of the two vWF type A-like domains of human COCH5B2 (labeled VA1 and VA2) with each other and with one of the type A-like domains of the following proteins: human collagen 12 α1 (COL12A1) VA module (SEQ ID NO:8); human cartilage matrix protein (CMP) A1 module (SEQ ID NO:9); and human von Willebrand factor (vWF) A3 module (SEQ ID NO:10).

FIG. 5 depicts a schematic representation of the deduced amino acid sequence of human COCH5B2, showing the positions of the cysteine residues with respect to the vWF A-like domains.

Figure 6:
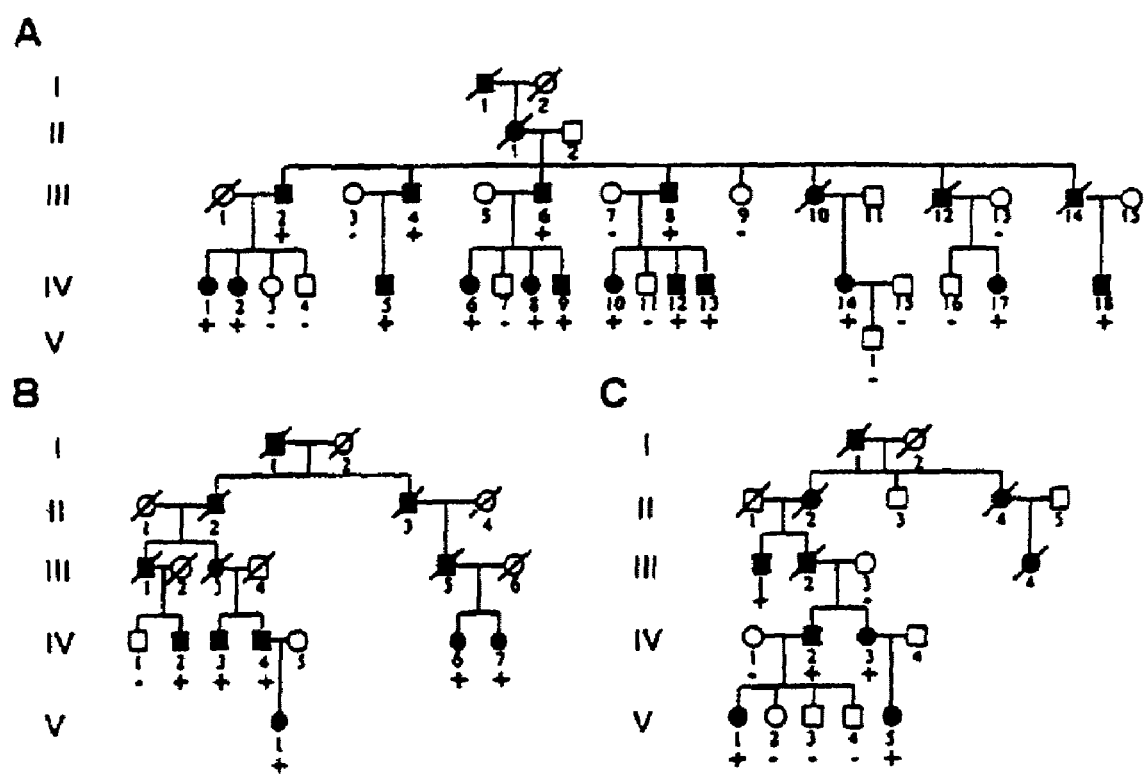

FIG. 6 depicts pedigrees of three DFNA9 kindreds (circles, females; squares, males; slash, deceased; darkened, hearing-impaired; clear, hearing) showing segregation of each mutation only with hearing-impaired family members. All individuals with hearing loss tested in (A) kindred 1W show a TrG 253 transversion in exon 4 of COCH5B2, (B) kindred 1Su show a GrA 319 transition in exon 5, and (C) kindred 1 St show a TrC 405 transition in exon 5 (indicated by +). All hearing individuals tested show absence of the respective mutations (indicated by −).

Figure 7:
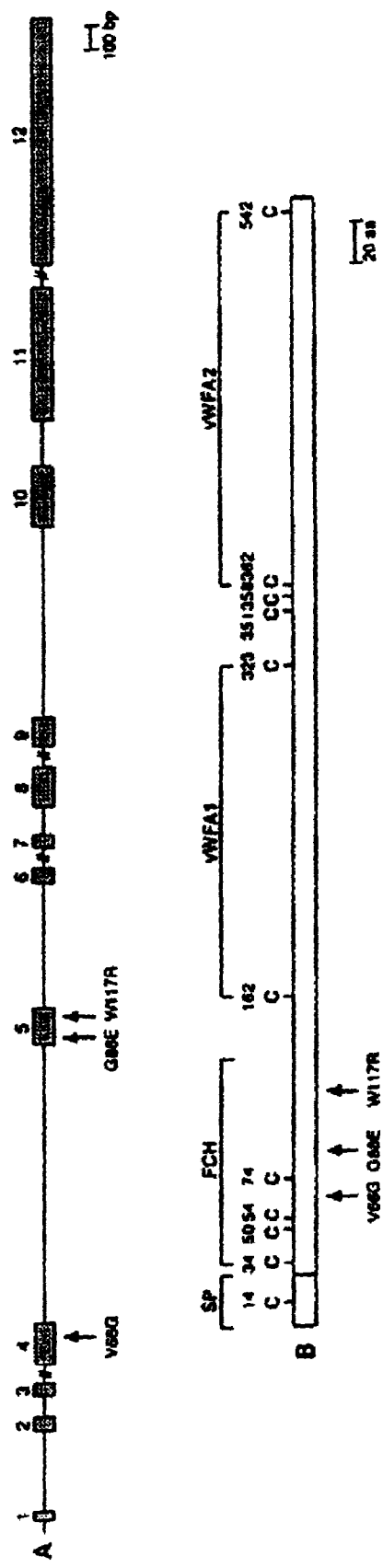

FIG. 7 is a schematic representation of genomic structure and the deduced amino acid sequence of COCH5B2. (A) Schematic drawing of human COCH5B2 genomic structure showing intron-exon organization of the gene. Exons are indicated by shaded boxes. Positions of missense mutations V66G, G88E, W117R, found in the DFNA9 kindreds one, two, and three, respectively, are shown with arrows. Introns of undetermined size are indicated ( ). The region of *Limulus* factor C homology (FCH) spans exons 4–6. The von Willebrand factor type A-like domain, vWFA1, is contained within exons 8–10; vWFA2 is in exons 11 and 12. (B) Schematic representation of the deduced amino acid sequence of human COCH5B2. The three missense mutations (arrows) are in the amino terminus of the protein, downstream of the predicted signal peptide (SP), and upstream of vWFA1 and vWFA2. This amino terminus region containing the mutations (FCH) is homologous to a domain in *Limulus* factor C with four conserved cysteine residues. (C) Alignment of the complete deduced amino acid sequence of human (GenBank No. AF006740), mouse (GenBank No. AF006741), and chicken (GenBank No. K01702) COCH5B2 and one domain of *Limulus* factor C (26). A high degree of cross-species homology, including conservation of all cysteine residues (dashed boxes) is seen. Dots indicate amino acid residues which are identical to those in human COCH5B2. A predicted signal peptide in the beginning of the sequence is indicated by a line. Three missense mutations (boxes), V66G, G88E, and W117R are seen in DFNA9 kindreds 1W, 1Su and 1St, respectively. Amino acid residues mutated in DFNA9 show cross-species conservation and all reside in a region with homology to a domain in *Limulus* factor C (underlined) containing four conserved cysteines.

DETAILED DESCRIPTION OF THE INVENTION

The present invention is based on the discovery of novel molecules, referred to herein as COCH5B2 nucleic acid and protein molecules, which play a role in inner ear biology. In one embodiment, the COCH5B2 molecules modulate an inner ear secretory pathway. In a preferred embodiment, the COCH5B2 molecules of the invention are capable of modulating proteins involved in the secretion of acidophillic mucosaccharide-containing ground substance. Histological examination temporal bone sections from individuals affected with DFNA9 show an accumulation of acidophillic deposits obstructing the cochlear and vestibular nerve channels, causing severe degeneration of dendrites and atrophy of cochlear and vestibular sense organs (Khetarpl et al., *Arch. Otolaryngol. Head Neck Surg.* 117:1032–1042, 1991; Khetarpal et al., *Arch. Otolaryngol. Head Neck Surg.* 119: 106–108, 1993). The expression patterns of these acidophillic deposits in the temporal bones of DFNA9 patients were found to parallel the expression pattern of COCH5B2. Thus, correlation of COCH5B2 expression in inner ear to the histological findings of DFNA9 patients, and the high level of COCH5B2 expression in the cochlea and vestibule, indicate that COCH5B2 plays a major role in DFNA9. Moreover, mutational analysis of COCH5B2 in families having individuals with DFNA9 demonstrated missense mutations in COCH5B2 gene in individuals affected with DFNA9. Thus, the COCH5B2 molecules of the present invention are useful in diagnosing and treating a human nonsyndromic sensorineural deafness with vestibular involvement (DFNA9).

In another embodiment, the COCH5B2 molecules are capable of modulating interactions of components of extracellular matrix (EMC). As used herein, "components of extracellular matrix" refer to proteins involved extracellular matrix production such as fibrillar collagens, e.g., COL1A2 and COL3A1. Using Northern analysis, COL1A2 and COL3A1 have been found to be expressed in the cochlea and levels comparable to COCH5B2 expression. (Robertson et al., *Genomics* 23:42–50, 1994). It is predicted that COCH5B2 interacts with the abundant fibrillar collagen for ECM assembly in the cochlea and thus, plays an important role in the assembly of this highly structured organ. Thus, COCH5B2 molecules (or modulators thereof) of the present invention can be used to treat various hearing disorders which involve dysfunction of the inner ear, e.g., the cochlea.

COCH5B2 nucleic acid molecules were identified from human fetal cochlear tissue by subtractive hybridization and differential screening of a cDNA library. The nucleotide sequence of the isolated human COCH5B2 cDNA and the predicted amino acid sequence of the human COCH5B2 protein are shown in FIG. 1 and in SEQ ID NOs: 1 and 2, respectively.

Murine COCH5B2 was identified in murine fetal brain tissue using human COCH5B2 cDNA to screen the fetal brain cDNA library. Comparison of human and murine COCH5B2 revealed a 89% sequence identity in the nucleotide sequences in the region of the open reading frame. In addition, the amino acid sequences of human and murine COCH5B2 share 94% sequence identity and 96% sequence similarity when conserved amino acid substitutions are taken into consideration.

The human COCH5B2 gene, which is approximately 2534 nucleotides in length, encodes a full length protein which is approximately 550 amino acid residues in length. The COCH5B2 protein is expressed in high levels in human fetal cochlea and vestibule and at low levels in human fetal brain and eye and human adult muscle. The human COCH5B2 protein contains at least one or two von Willabrand Factor (vWF) type A-like domains, at least one factor C homologous domain, a signal sequence, and conserved flanking cysteine residues, as defined herein. As used herein, the term "von Willebrand Factor (vWF) type A-like domain" refers to a structural amino acid domain which is about 100 to 200 amino acid residues in length, preferably at least about 125 to 175 amino acid residues in length, and more preferably at least about 150 amino acid residues in length, and often occurs in multiple numbers within a COCH5B2 protein sequence. The vWF type A-like domains of COCH5B2 includes about amino acids 165–309 of SEQ ID NO:2 (shown as SEQ ID NO:4) and about amino acids 366 to 514 of SEQ ID NO:2 (shown as SEQ ID NO:5). As used herein, the term "facor C homologous domain" refers to a structural amino acid domain which is about 100 amino acid residues in length, preferably at least about 104 amino acid residues in length, and more preferably at least about 110 amino acid residues in length. The facor C homologous domain of COCH5B2 includes about amino acids 32–136 of SEQ ID NO:2 (shown as SEQ ID NO:11).

Human COCH5B2 also has conserved cystein residues which are adjacent to the amino and carboxy termini of each of the vWF type-a like domains. Conserved cysteine residues as used herein refer to cysteine residues which are conserved between COCH5B2 molecules. Preferably, the vWF type A-like domains of human COCH5B2 have cysteine residues flanking either end of the domain which are located in the same or similar positions as cysteine residues in other COCH5B2 proteins. For example, when a human COCH5B2 protein of the invention is aligned with a COCH5B2 family member for purposes of comparison (see e.g., FIG. 2) preferred cysteine residues of the invention are those in which cysteine residues in the amino acid sequence of human COCH5B2 are located in the same or similar position as the cysteine residues in other COCH5B2 family members. As an illustrative embodiment, FIG. 2 shows cysteine residues located in the same or similar positions of the human COCH5B2 protein (corresponding to SEQ ID NO:2) and murine COCH5B2 (corresponding to SEQ ID NO:7) in the following locations: amino acid number 34 of human COCH5B2 and amino acid number 36 of the murine COCH5B2; amino acid number 50 of human COCH5B2 and amino acid number 52 of murine COCH5B2; amino acid number 54 of human COCH5B2 and amino acid number 56 of murine COCH5B2; amino acid number 74 of human COCH5B2 and amino acid number 76 of murine COCH5B2; amino acid number 162 of human COCH5B2 and amino acid number 164 of murine COCH5B2; amino acid number 323 of human COCH5B2 and amino acid number 325 of murine COCH5B2; amino acid number 351 of human COCH5B2 and amino acid number 353 of murine COCH5B2; amino acid number 358 of human COCH5B2 and amino acid number 360 of murine COCH5B2; amino acid number 361 of human COCH5B2 and amino acid number 363 of murine COCH5B2; and amino acid number 542 of human COCH5B2 and amino acid number 544 of murine COCH5B2.

In another embodiment of the invention, a COCH5B2 protein has at least one vWF type A-like domain and/or a signal sequence. As used herein, a "signal sequence" refers to a peptide of about 20–30 amino acid residues in length which occurs at the N-terminus of secretory and integral membrane proteins and which contains a majority of hydrophobic amino acid residues. For example, a signal sequence contains at least about 15–45 amino acid residues, preferably about 20–40 amino acid residues, more preferably about 20–30 amino acid residues, and more preferably about 24–28 amino acid residues, and has at least about 40–70%, preferably about 50–65%, and more preferably about 55–60% hydrophobic amino acid residues (e.g., Alanine, Valine, Leucine, Isoleucine, Phenylalanine, Tyrosine, Tryptophan, or Proline). Such a "signal sequence", also referred to in the art as a "signal peptide", serves to direct a protein containing such a sequence to a lipid bilayer. For example, in one embodiment, a COCH5B2 protein contains a signal sequence of about amino acids 1–26 of SEQ ID NO:2. The prediction of such a signal peptide can be made, for example, using the von Heijne's rules for signal peptides and their potential cleavage sites (von Heijne *Nucleic Acid Res.* 14:4683–4690, 1986).

The COCH5B2 protein or a biologically active portion or fragment of the invention can have one or more of the following activities: 1) it can interact, e.g., bind, with components of extracellular matrix (e.g., fibrillar collagen, e.g., COL1A2, COL3A1); 2) it can modulate cell/extracellular matrix interactions; 3) it can modulate cell—cell adhesions; 4) it can interact, e.g., bind, with glycoproteins and/or proteoglycans for clearing them; 5) it can provide scaffolding by interacting with other extracellular matrix components (e.g., fibrillar collagen, e.g., COL1A2, COL3A1); and 6) it can modulate an inner ear secretory pathway (e.g., it can modulate production of acidophillic deposits).

Various aspects of the invention are described in further detail in the following subsections:

I. Isolated Nucleic Acid Molecules

One aspect of the invention features isolated nucleic acid molecules that encode COCH5B2 or biologically active portions thereof, as well as nucleic acid fragments sufficient for use as hybridization probes to identify COCH5B2-encoding nucleic acid (e.g., COCH5B2 mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is a nucleic acid fragment which is separated from other nucleic acid molecules which are present in the natural source of the nucleic acid. Preferably, an "isolated" nucleic acid is free of sequences which naturally flank the nucleic acid (i.e., sequences located at the 5' or 3' ends of the nucleic acid) in the genomic DNA of the organism from which the nucleic acid is derived. For example, in various embodiments, the isolated COCH5B2 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., an endothelial cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO: 1 or SEQ ID NO:6, or a portion thereof, can be isolated using standard molecular biology techniques and the sequence information provided herein. For example, a human COCH5B2 cDNA can be isolated from a human fetal cochlear library using all or portion of SEQ ID NO: 1 or SEQ ID NO:6 as a hybridization probe and standard hybridization techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989). Moreover, a nucleic acid molecule encompassing all or a portion of SEQ ID NO: 1 or SEQ ID NO:6 can be isolated by the polymerase chain reaction using oligonucleotide primers designed based upon the sequence of SEQ ID NO: OR SEQ ID NO:6. For example, mRNA can be isolated from normal endothelial cells (e.g., by the guanidinium-thiocyanate extraction procedure of Chirgwin et al., *Biochemistry* 18: 5294–5299, 1979) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1 or SEQ ID NO:6. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a COCH5B2 nucleotide sequence can be prepared by standard synthetic techniques, e.g., using an automated DNA synthesizer.

In a preferred embodiment, an isolated nucleic acid molecule of the invention includes the nucleotide sequence shown in SEQ ID NO: 1. The sequence of SEQ ID NO: 1 corresponds to the human COCH5B2 cDNA. This cDNA includes sequences encoding the COCH5B2 protein (i.e., "the coding region", from nucleotides 57–1709), as well as 5' untranslated sequences (nucleotides 1 to 56) and 3' untranslated sequences (nucleotides 1710–2534). Alternatively, the nucleic acid molecule can include only the coding region of SEQ ID NO: 1 (e.g., nucleotides 57–1709).

In another preferred embodiment, an isolated nucleic acid molecule of the invention includes a nucleic acid molecule which is a complement of the nucleotide sequence shown in SEQ ID NO: 1, SEQ ID NO:6, or a portion of either of these nucleotide sequences. A nucleic acid molecule which is complementary to the nucleotide sequence shown in SEQ ID NO: 1 or SEQ ID NO:6 is one which is sufficiently complementary to the nucleotide sequence shown in SEQ ID NO: 1 or SEQ ID NO:6 such that it can hybridize to the nucleotide sequence shown in SEQ ID NO:1 or SEQ ID NO:6, thereby forming a stable duplex.

In still another preferred embodiment, an isolated nucleic acid molecule of the invention includes a nucleotide sequence which has at least about 60–65%, preferably at least about 70–75%, more preferably at least about 80–85%, and even more preferably at least about 90–95%96%, 97%, 98% or 99% sequence identity to the nucleotide sequence shown in SEQ ID NO: 1, SEQ ID NO:6, or a portion of either of these nucleotide sequences. In an additional preferred embodiment, an isolated nucleic acid molecule of the invention includes a nucleotide sequence which hybridizes, e.g., hybridizes under stringent conditions, to the nucleotide sequence shown in SEQ ID NO: 1, SEQ ID NO:6, or a portion of either of these nucleotide sequences.

Moreover, the nucleic acid molecule of the invention can include only a portion of the coding region of SEQ ID NO: 1 or SEQ ID NO:6, for example a fragment which can be used as a probe or primer or a fragment encoding a biologically active portion of COCH5B2. The nucleotide sequence determined from the cloning of the COCH5B2 gene from a mammal allows for the generation of probes and primers designed for use in identifying and/or cloning COCH5B2 homologues in other cell types, e.g. from other tissues, as well as COCH5B2 homologues from other mammals. The probe/primer typically includes substantially purified oligonucleotide. The oligonucleotide typically includes a region of nucleotide sequence that hybridizes under stringent conditions to at least about 12, preferably about 25, more preferably about 40, 50 or 75 consecutive nucleotides of SEQ ID NO: 1 or SEQ ID NO:6 sense, an anti-sense sequence of SEQ ID NO: 1 or SEQ ID NO:6, or naturally occurring mutants thereof. Primers based on the nucleotide sequence in SEQ ID NO: 1 or SEQ ID NO:6 can be used in PCR reactions to clone COCH5B2 homologues. Probes based on the COCH5B2 nucleotide sequences can be used to detect transcripts or genomic sequences encoding the same or homologous proteins. In preferred embodiments, the probe further includes a label group attached thereto, e.g. the label group can be a radioisotope, a fluorescent compound, an enzyme, or an enzyme co-factor. Such probes can be used as a part of a diagnostic test kit for identifying cells or tissue which misexpress a COCH5B2 protein, such as by measuring a level of a COCH5B2-encoding nucleic acid in a sample of cells from a subject e.g., detecting COCH5B2 mRNA levels or determining whether a genomic COCH5B2 gene has been mutated or deleted. For example, probes can also be used in diagnostic screening to identify individuals suffering from a hearing disorder, e.g., DFNA9.

In one embodiment, the nucleic acid molecule of the invention encodes a protein or portion thereof which includes an amino acid sequence which is sufficiently homologous to an amino acid sequence of SEQ ID NO:2 or SEQ ID NO:7 such that the protein or portion thereof maintains one or more COCH5B2 activities. As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO:2) amino acid residues to an amino acid sequence of SEQ ID NO:2 or SEQ ID NO:7, such that the protein or portion thereof is able to maintain one or more COCH5B2 activities. In another embodiment, the protein has at least about 60–70%, preferably at least about 80–85%, and more preferably at least about 86, 88, 90%, and most preferably at least about 90–95%96%, 97%, 98% or 99% sequence identity to the entire amino acid sequence of SEQ ID NO:2 or SEQ ID NO:7.

Portions of proteins encoded by the COCH5B2 nucleic acid molecule of the invention are preferably biologically active portions of the COCH5B2 protein. As used herein, the term "biologically active portion of COCH5B2" is intended to include a portion, e.g., a domain/motif, of COCH5B2 that has one or more of the following activities: 1) it can interact, e.g., bind, with components of extracellular matrix (e.g., fibrillar collagen, e.g., COL1A2, COL3A1); 2) it can modulate cell/extracellular matrix interactions; 3) it can modulate cell—cell adhesions; 4) it can interact, e.g., bind, with glycoproteins and/or proteoglycans for clearing them; 5) it can provide scaffolding by interacting with other extracellular matrix components (e.g., fibrillar collagen, e.g., COL1A2, COL3A1); and 6) it can modulate an inner ear secretory pathway (e.g., it can modulate production of acidophillic deposits).

In one embodiment, the biologically active portion of COCH5B2 includes one or two vWF type A-like domains. Preferably, the vWF type A-like domain is encoded by a nucleic acid molecule derived from a human and has at least about 75%, preferably at least about 80–85%, and most preferably at least about 90–95% or more sequence identity to SEQ ID NO:4 or SEQ ID NO:5. If the vWF type A-like domain is encoded by a nonmammalian nucleic acid, it has preferably at least about 55%, preferably at least about 60–65%, even more preferably at least about 70–75% most preferably at least about 80–90% or more sequence identity to SEQ ID NO:4 or SEQ ID NO:5. In a preferred embodiment, the biologically active portion of the protein which includes the vWF type A-like domain can modulate the activity of a component of the extracellular matrix or a protein involved in the secretion of acidophillic deposits. In a preferred embodiment, the biologically active portion includes the vWF type A-like domain of COCH5B2 as represented by amino acid residues 165 to 309 of SEQ ID NO:2 (as shown in SEQ ID NO:4) or amino acid residues 366 to 514 of SEQ ID NO:2 (as shown in SEQ ID NO:5). Additional nucleic acid fragments encoding biologically active portions of COCH5B2 can be prepared by isolating a portion of SEQ ID NO: 1, expressing the encoded portion of COCH5B2 protein or peptide (e.g., by recombinant expression in vitro) and assessing the activity of the encoded portion of COCH5B2 protein or peptide.

In another embodiment, the biologically active portion of COCH5B2 includes at least one factor C homologous domain. Preferably, the factor C homologous domain is encoded by a nucleic acid molecule derived from a human and has at least about 75%, preferably at least about 80–85%, and most preferably at least about 90–95% or more sequence identity to SEQ ID NO: 11. If the factor C homologous domain is encoded by a nonmammalian nucleic acid, it has preferably at least about 55%, preferably at least about 60–65%, even more preferably at least about 70–75% most preferably at least about 80–90% or more sequence identity to SEQ ID NO:11. In a preferred embodiment, the biologically active portion of the protein which includes the factor C homologous domain can modulate the activity of a component of the extracellular matrix or a protein involved in the secretion of acidophillic deposits. In a preferred embodiment, the biologically active portion includes the factor C homologous domain of COCH5B2 as represented by amino acid residues 32–136 of SEQ ID NO:2 (as shown in SEQ ID NO:11). Additional nucleic acid fragments encoding biologically active portions of COCH5B2 can be prepared by isolating a portion of SEQ ID NO: 1, expressing the encoded portion of COCH5B2 protein or peptide (e.g., by recombinant expression in vitro) and assessing the activity of the encoded portion of COCH5B2 protein or peptide.

The invention further encompasses nucleic acid molecules that differ from the nucleotide sequence shown in SEQ ID NO: 1 or SEQ ID NO:6 (and portions thereof) due to degeneracy of the genetic code and thus encode the same COCH5B2 protein as that encoded by the nucleotide sequence shown in SEQ ID NO: 1 or SEQ ID NO:6. In another embodiment, an isolated nucleic acid molecule of the invention has a nucleotide sequence encoding a protein having an amino acid sequence shown in SEQ ID NO:2 or SEQ ID NO:7. In a still further embodiment, the nucleic acid molecule of the invention encodes a full length human protein which is substantially homologous to the amino acid sequence of SEQ ID NO:2 (encoded by the open reading frame shown in SEQ ID NO:3), or SEQ ID NO:7.

In addition to the human COCH5B2 nucleotide sequence shown in SEQ ID NO: 1, it will be appreciated by those skilled in the art that DNA sequence polymorphisms that lead to changes in the amino acid sequences of COCH5B2 may exist within a population (e.g., the human population). Such genetic polymorphism in the COCH5B2 gene may exist among individuals within a population due to natural allelic variation. As used herein, the terms "gene" and "recombinant gene" refer to nucleic acid molecules comprising an open reading frame encoding a COCH5B2 protein, preferably a mammalian COCH5B2 protein. Such natural allelic variations can typically result in 1–5% variance in the nucleotide sequence of the COCH5B2 gene. Any and all such nucleotide variations and resulting amino acid polymorphisms in COCH5B2 that are the result of natural allelic variation and that do not alter the functional activity of COCH5B2 are intended to be within the scope of the invention. Moreover, nucleic acid molecules encoding COCH5B2 proteins from other species, and thus which have a nucleotide sequence which differs from the human sequence of SEQ ID NO: 1, are intended to be within the scope of the invention. Nucleic acid molecules corresponding to natural allelic variants and nonhuman homologues of the human COCH5B2 cDNA of the invention can be isolated based on their homology to the human COCH5B2 nucleic acid disclosed herein using the human cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising the nucleotide sequence of SEQ ID NO: 1, or SEQ ID NO:7. In other embodiments, the nucleic acid is at least 30, 50, 100, 205, 210, 220, 230, 250, 300, 400, 500, or 600 nucleotides in length. Preferably, the nucleic acid is more than 200 bp in length and/or it excludes nucleotides 1457–1654. More preferably, the nucleic acid is more than 600 base pairs in length, e.g., and it is at least 700–1000 base pairs in length. As used herein, the term "hybridizes under stringent conditions" refers to conditions for hybridization and washing under which nucleotide sequences typically remain hybridized to each other. Preferably, the conditions are such that sequences which have at least about 60%, at least about 65%, more preferably at least about 70%, and even more preferably at least about 75% or more sequence identity to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred example of stringent hybridization conditions are hybridization in 6× sodium chloride/sodium citrate (SSC) at about 45□ C., followed by one or more washes in 0.2×SSC, 0.1% SDS at 50–65□ C. Preferably, an isolated nucleic acid molecule of the invention that hybridizes under stringent conditions to the sequence of SEQ ID NO: 1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human COCH5B2.

In addition to naturally-occurring allelic variants of the COCH5B2 sequence that may exist in the population, the skilled artisan will further appreciate that changes can be introduced by mutation into the nucleotide sequence of SEQ ID NO: 1 or SEQ ID NO:6, thereby leading to changes in the amino acid sequence of the encoded COCH5B2 protein, without altering the functional ability of the COCH5B2 protein. For example, nucleotide substitutions leading to amino acid substitutions at "non-essential" amino acid residues can be made in the sequence of SEQ ID NO: 1 or SEQ ID NO:6. A "non-essential" amino acid residue is a residue that can be altered from the wild-type sequence of COCH5B2 (e.g., the sequence of SEQ ID NO:2 or SEQ ID NO:7) without altering the activity of COCH5B2, whereas an "essential" amino acid residue is required for COCH5B2 activity. For example, conserved amino acid residues, e.g., cysteine residues, flanking the vWF type A-like domains of COCH5B2 are most likely important for the structure of COCH5B2 and are thus essential residues of COCH5B2. Other amino acid residues, however, (e.g., those that are not conserved or only semi-conserved in the vWF type A-like domain) may not be essential for activity and thus are likely to be amenable to alteration without altering COCH5B2 activity.

Accordingly, another aspect of the invention features nucleic acid molecules encoding COCH5B2 proteins that contain changes in amino acid residues that are not essential for COCH5B2 activity. Such COCH5B2 proteins differ in amino acid sequence from SEQ ID NO:2 or SEQ ID NO:7 yet retain at least one of the COCH5B2 activities described herein. In one embodiment, the isolated nucleic acid molecule includes a nucleotide sequence encoding a protein, wherein the protein includes an amino acid sequence having at least about 60% sequence identity to the amino acid sequence of SEQ ID NO:2 or SEQ ID NO:7 and maintains one or more COCH5B2 activities. Preferably, the protein encoded by the nucleic acid molecule has at least about 70% sequence identity to SEQ ID NO:2 or SEQ ID NO:7, more preferably it has at least about 80–85% sequence identity to SEQ ID NO:2 or SEQ ID NO:7, even more preferably it has at least about 90% sequence identity to SEQ ID NO:2 or SEQ ID NO:7, and most preferably it has at least about 95–99% sequence identity to SEQ ID NO:2 or SEQ ID NO:7.

To determine the percent homology of two amino acid sequences (e.g., SEQ ID NO:2 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., SEQ ID NO:2) is occupied by the same amino acid residue or nucleotide as the corresponding position in the other sequence (e.g., a mutant form of COCH5B2), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100). For example, if 6 of 10, of the positions in two sequences are matched or homologous then the two sequences are 60% homologous or have 60% sequence identity. By way of example, the DNA sequences ATTGCC and TATGGC share 50% homology or sequence identity. Generally, a comparison is made when two sequences are aligned to give maximum homology or sequence identity.

The comparison of sequences and determination of percent homology between two sequences can be accomplished using a mathematical algorithim. A preferred, non-limiting example of a mathematical algorithim utilized for the comparison of sequences is the algorithm of Karlin and Altschul *Proc. Natl. Acad. Sci. USA* 87:2264–68, 1990, modified as in Karlin and Altschul *Proc. Natl. Acad. Sci. USA* 90:5873–77, 1993. Such an algorithm is incorporated into the NBLAST and XBLAST programs (version 2.0) of Altschul, et al. *J. Mol. Biol.* 215:403–10, 1990. BLAST nucleotide searches can be performed with the NBLAST program, score=100, wordlength-12 to obtain nucleotide sequences homologous to Coch 5B2 nucleic acid molecules of the invention. BLAST protein searches can be performed with the XBLAST program, score=50, wordlength=3 to obtain amino acid sequences homologous to Coch 5B2 protein molecules of the invention. To obtain gapped alignments for comparison purposes. Gapped BLAST can be utilized as described in Altschul et al., *Nucleic Acids Res.* 25(17):3389–3402, 1997. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithim utilized for the comparison of sequences is the algorithm of Myers and Miller, CABIOS (1989). Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

An isolated nucleic acid molecule encoding a COCH5B2 protein homologous to the protein of SEQ ID NO:2 or SEQ ID NO:7 can be created by introducing one or more nucleotide substitutions, additions or deletions into the nucleotide sequence of SEQ ID NO: 1 or SEQ ID NO:6 such that one or more amino acid substitutions, additions or deletions are introduced into the encoded protein. Mutations can be introduced into SEQ ID NO: 1 or SEQ ID NO:6 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in COCH5B2 is preferably replaced with another amino acid residue from the same side chain family. Alternatively, in another embodiment, mutations can be introduced randomly along all or part of a COCH5B2 coding sequence, such as by saturation mutagenesis, and the resultant mutants can be screened for a COCH5B2 activity described herein to identify mutants that retain COCH5B2 activity. Following mutagenesis of SEQ ID NO: 1 or SEQ ID NO:6, the encoded protein can be expressed recombinantly and the activity of the protein can be determined using, for example, assays described herein.

In addition to the nucleic acid molecules encoding COCH5B2 proteins described above, another aspect of the invention features isolated nucleic acid molecules which are antisense thereto. An "antisense" nucleic acid includes a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire COCH5B2 coding strand, or to only a portion thereof. In one embodiment, an antisense nucleic acid molecule is antisense to a "coding region" of the coding strand of a nucleotide sequence encoding COCH5B2. The term "coding region" refers to the region of the nucleotide sequence comprising codons which are translated into amino acid residues (e.g., the entire coding region of SEQ ID NO:1 includes nucleotides 57–1709). In another embodiment, the antisense nucleic acid molecule is antisense to a "noncoding region" of the coding strand of a nucleotide sequence encoding COCH5B2. The term "noncoding region" refers to 5' and 3' sequences which flank the coding region that are not translated into amino acids (i.e., also referred to as 5' and 3' untranslated regions).

Given the coding strand sequences encoding COCH5B2 disclosed herein (e.g., SEQ ID NO: 1 or SEQ ID NO:6), antisense nucleic acids of the invention can be designed according to the rules of Watson and Crick base pairing. The antisense nucleic acid molecule can be complementary to the entire coding region of COCH5B2 mRNA, but more preferably is an oligonucleotide which is antisense to only a portion of the coding or noncoding region of COCH5B2 mRNA. For example, the antisense oligonucleotide can be complementary to the region surrounding the translation start site of COCH5B2 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a COCH5B2 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., *Nucleic Acids. Res.* 15:6625–6641, 1987). The antisense nucleic acid molecule can also include a 2'-o-methylribonucleotide (Inoue et al., *Nucleic Acids Res.* 15:6131–6148, 1987) or a chimeric RNA-DNA analogue (Inoue et al., *FEBS Lett.* 215:327–330, 1987).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach *Nature* 334:585–591, 1988)) can be used to catalytically cleave COCH5B2 mRNA transcripts to thereby inhibit translation of COCH5B2 mRNA. A ribozyme having specificity for a COCH5B2-encoding nucleic acid can be designed based upon the nucleotide sequence of a COCH5B2 cDNA disclosed herein (i.e., SEQ ID NO: 1). For example, a derivative of a Tetrahymena L-19 IVS RNA can be constructed in which the nucleotide sequence of the active site is complementary to the nucleotide sequence to be cleaved in a COCH5B2-encoding mRNA. See, e.g., Cech et al. U.S. Pat. No. 4,987,071 and Cech et al. U.S. Pat. No. 5,116,742. Alternatively, COCH5B2 mRNA can be used to select a catalytic RNA having a specific ribonuclease activity from a pool of RNA molecules. See, e.g., Bartel, D. and Szostak, J. W. *Science* 261:1411–1418, 1993.

Alternatively, COCH5B2 gene expression can be inhibited by targeting nucleotide sequences complementary to the regulatory region of the COCH5B2 (e.g., the COCH5B2 promoter and/or enhancers) to form triple helical structures that prevent transcription of the COCH5B2 gene in target cells. See generally, Helene, C. *Anticancer Drug Des.* 6(6): 569–84, 1991; Helene, C. et al. *Ann. N.Y. Acad. Sci.* 660: 27–36, 1992; and Maher, L. J. *Bioassays* 1412):807–15, 1992.

II. Recombinant Expression Vectors and Host Cells

Another aspect of the invention features vectors, preferably expression vectors, containing a nucleic acid encoding COCH5B2 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention include a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., COCH5B2 proteins, mutant forms of COCH5B2, fusion proteins, etc.).

The recombinant expression vectors of the invention can be designed for expression of COCH5B2 in prokaryotic or eukaryotic cells. For example, COCH5B2 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. *Gene* 67:31–40, 1988), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the COCH5B2 is cloned into a pGEX expression vector to create a vector encoding a fusion protein comprising, from the N-terminus to the C-terminus, GST-thrombin cleavage site-COCH5B2. The fusion protein can be purified by affinity chromatography using glutathione-agarose resin. Recombinant COCH5B2 unfused to GST can be recovered by cleavage of the fusion protein with thrombin.

Examples of suitable inducible non-fusion *E. coli* expression vectors include pTrc (Amann et al., *Gene* 69:301–315, 1988) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gnl). This viral polymerase is supplied by host strains BL21(DE3) or HMS174(DE3) from a resident λ prophage harboring a T7 gnl gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. *Nucleic Acids Res.* 20:2111–2118, 1992). Such alteration of nucleic acid sequences of the invention can be carried out by standard DNA synthesis techniques.

In another embodiment, the COCH5B2 expression vector is a yeast expression vector. Examples of vectors for expression in yeast *S. cerivisae* include pYepSec1 (Baldari, et al., *Embo J.* 6:229–234, 1987), pMFa (Kujan and Herskowitz, *Cell* 30:933–943, 1982), pJRY88 (Schultz et al., *Gene* 54:113–123, 1987), and pYES2 (Invitrogen Corporation, San Diego, Calif.).

Alternatively, COCH5B2 can be expressed in insect cells using baculovirus expression vectors. Baculovirus vectors available for expression of proteins in cultured insect cells (e.g., Sf 9 cells) include the pAc series (Smith et al., *Mol. Cell Biol.* 3:2156–2165, 1983) and the pVL series (Lucklow and Summers, *Virology* 170:31–39, 1989).

In yet another embodiment, a nucleic acid of the invention is expressed in mammalian cells using a mammalian expression vector. Examples of mammalian expression vectors include pCDM8 (Seed, B., *Nature* 329:840, 1987) and pMT2PC (Kautman et al., *EMBO J.* 6:187–195, 1987). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., *Genes Dev.* 1:268–277, 1987), lymphoid-specific promoters (Calame and Eaton (*Adv. Immunol.* 43:235–275, 1988), in particular promoters of T cell receptors (Winoto and Baltimore *EMBO J.* 8:729–733, 1989) and immunoglobulins (Banerji et al. *Cell* 33:729–740, 1983; Queen and Baltimore Cell 33:741–748, 1983), neuron-specific promoters (e.g., the neurofilament promoter; Byrne and Ruddle, *PNAS* 86:5473–5477, 1989), pancreas-specific promoters (Edlund et al. *Science* 230:912–916, 1985), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss *Science* 249:374–379, 1990) and the a-fetoprotein promoter (Campes and Tilghman *Genes Dev.* 3:537–546, 1989).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to COCH5B2 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention features host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, COCH5B2 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding COCH5B2 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) COCH5B2 protein. Accordingly, the invention further provides methods for producing COCH5B2 protein using the host cells of the invention. In one embodiment, the method includes culturing the host cell of invention (into which a recombinant expression vector encoding COCH5B2 has been introduced) in a suitable medium until COCH5B2 is produced. In another embodiment, the method further includes isolating COCH5B2 from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as hearing disorders. For example, in one embodiment, a host cell of the invention is a fertilized oocyte or an embryonic stem cell into which COCH5B2-coding sequences have been introduced. Such host cells can then be used to create non-human transgenic animals in which exogenous COCH5B2 sequences have been introduced into their genome or homologous recombinant animals in which endogenous COCH5B2 sequences have been altered. Such animals are useful for studying the function and/or activity of COCH5B2 and for identifying and/or evaluating modulators of COCH5B2 activity. As used herein, a "transgenic animal" is a nonhuman animal, preferably a mammal, more preferably a rodent such as a rat or mouse, in which one or more of the cells of the animal includes a transgene. The term "transgenic animal" is also intended to include a homologous recombinant animal described herein. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous COCH5B2 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing COCH5B2-encoding nucleic acid into the male pronuclei of a fertilized oocyte, e.g., by microinjection, retroviral infection, and allowing the oocyte to develop in a pseudopregnant female foster animal. The human COCH5B2 cDNA sequence of SEQ ID NO: 1 or SEQ ID NO:6 can be introduced as a transgene into the genome of a nonhuman animal. Intronic sequences and polyadenylation signals can also be included in the transgene to increase the efficiency of expression of the transgene. A tissue-specific regulatory sequence(s) can be operably linked to the COCH5B2 transgene to direct expression of COCH5B2 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No.

4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the COCH5B2 transgene in its genome and/or expression of COCH5B2 mRNA in tissues or cells of the animals. A transgenic founder animal can then be used to breed additional animals carrying the transgene. Moreover, transgenic animals carrying a transgene encoding COCH5B2 can further be bred to other transgenic animals carrying other transgenes.

To create a homologous recombinant animal, a vector is prepared which contains at least a portion of a COCH5B2 gene into which a deletion, addition or substitution has been introduced to thereby alter, e.g., functionally disrupt, the COCH5B2 gene. The COCH5B2 gene can be a human gene (e.g., from a human genomic clone isolated from a human genomic library screened with the cDNA of SEQ ID NO:1), but more preferably, is a nonhuman homologue of a human COCH5B2 gene. For example, a mouse COCH5B2 gene in SEQ ID NO:6 can be used to construct a homologous recombination vector suitable for altering an endogenous COCH5B2 gene in the mouse genome. In a preferred embodiment, the vector is designed such that, upon homologous recombination, the endogenous COCH5B2 gene is functionally disrupted (i.e., no longer encodes a functional protein; also referred to as a "knock out" vector). Alternatively, the vector can be designed such that, upon homologous recombination, the endogenous COCH5B2 gene is mutated or otherwise altered but still encodes functional protein (e.g., the upstream regulatory region can be altered to thereby alter the expression of the endogenous COCH5B2 protein). In the homologous recombination vector, the altered portion of the COCH5B2 gene is flanked at its 5' and 3' ends by additional nucleic acid of the COCH5B2 gene to allow for homologous recombination to occur between the exogenous COCH5B2 gene carried by the vector and an endogenous COCH5B2 gene in an embryonic stem cell. The additional flanking COCH5B2 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R., *Cell* 51:503, 1987 for a description of homologous recombination vectors). The vector is introduced into an embryonic stem cell line (e.g., by electroporation) and cells in which the introduced COCH5B2 gene has homologously recombined with the endogenous COCH5B2 gene are selected (see e.g., Li, E. et al. *Cell* 69:915, 1992). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A., *Current Opinion in Biotechnology* 2:823–829, 1991 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhumans animals can be produced which contain selected systems which allow for regulated expression of the transgene. One example of such a system is the cre/loxP recombinase system of bacteriophage P 1. For a description of the cre/loxP recombinase system, see, e.g., Lakso et al., *PNAS* 89:6232–6236, 1992. Another example of a recombinase system is the FLP recombinase system of *Saccharomyces cerevisiae* (O'Gorman et al., *Science* 251:1351–1355, 1991. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. *Nature* 385:810–813, 1997. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated COCH5B2 Proteins and Anti-COCH5B2 Antibodies

Another aspect of the invention features isolated COCH5B2 proteins, and biologically active portions thereof, as well as peptide fragments suitable for use as immunogens to raise anti-COCH5B2 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of COCH5B2 protein in which the protein is separated from cellular components of the cells in which it is naturally or recombinantly produced. In one embodiment, the language "substantially free of cellular material" includes preparations of COCH5B2 protein having less than about 30% (by dry weight) of non-COCH5B2 protein (also referred to herein as a "contaminating protein"), more preferably less than about 20% of non-COCH5B2 protein, still more preferably less than about 10% of non-COCH5B2 protein, and most preferably less than about 5% non-COCH5B2 protein. When the COCH5B2 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of COCH5B2 protein in which the protein is separated from chemical precursors or other chemicals which are involved in the synthesis of the protein. In one embodiment, the language "substantially free of chemical precursors or other chemicals" includes preparations of COCH5B2 protein having less than about 30% (by dry weight) of chemical precursors or non-COCH5B2 chemicals, more preferably less than about 20% chemical precursors or non-COCH5B2 chemicals, still more preferably less than about 10% chemical precursors or non-COCH5B2 chemicals, and most preferably less than about 5% chemical precursors or non-COCH5B2 chemicals. In preferred embodiments, isolated proteins or biologically active portions thereof lack contaminating proteins from the same animal from which the COCH5B2 protein is derived. Typically, such proteins are produced by recombinant expression of, for example, a human COCH5B2 protein in a nonhuman cell.

In one embodiment, the COCH5B2 protein or portion thereof includes an amino acid sequence which is sufficiently homologous to an amino acid sequence of SEQ ID NO:2 or SEQ ID NO:7 such that the protein or portion thereof maintains one or more COCH5B2 activities. The portion of the protein is preferably a biologically active portion as described herein. In another preferred embodiment, the COCH5B2 protein (i.e., amino acid residues 1–550) has an amino acid sequence shown in SEQ ID NO:2, or SEQ ID NO:7. The preferred COCH5B2 proteins of the present invention also preferably possess at least one of the COCH5B2 activities described herein.

In other embodiments, the COCH5B2 protein is substantially homologous to the amino acid sequence of SEQ ID NO:2 or SEQ ID NO:7 and retains the functional activity of the protein of SEQ ID NO:2 or SEQ ID NO:7 yet differs in amino acid sequence due to natural allelic variation or mutagenesis, as described in detail in subsection I above. Accordingly, in another embodiment, the COCH5B2 protein is a protein which includes an amino acid sequence which has at least about 60–70%, preferably at least about 80–85%, and more preferably at least about 86, 88, 90%, and most preferably at least about 90–95%, 96%, 97%, 98% or 99% sequence identity to the entire amino acid sequence of SEQ ID NO:2 or SEQ ID NO:7 and which has at least one of the COCH5B2 activities described herein. In other embodiment, the invention pertains to a full length human protein which is substantially homologous to the entire amino acid sequence of SEQ ID NO:2 or SEQ ID NO:7.

Biologically active portions of the COCH5B2 protein include peptides comprising amino acid sequences derived from the amino acid sequence of the COCH5B2 protein, e.g., the amino acid sequence shown in SEQ ID NO:2, SEQ ID NO:7 or the amino acid sequence of a protein homologous to the COCH5B2 protein, which include less amino acids than the full length COCH5B2 protein or the full length protein which is homologous to the COCH5B2 protein, and exhibit at least one activity of the COCH5B2 protein. Typically, biologically active portions (peptides, e.g., peptides which are, for example, 5, 10, 15, 20, 30, 35, 36, 37, 38, 39, 40, 50, 75, 100, 120, 150 or more amino acids in length) include a domain or motif, e.g., a vWF type A-like domain or a factor C homologous domain, with at least one activity of the COCH5B2 protein. Preferably, the domain is a vWF type A-like domain derived from a human and has at least about 55%, preferably at least about 60–65%, even more preferably at least about 70–75% and most preferably at least about 80–90% or more sequence identity to SEQ ID NO:4 or SEQ ID NO:5. If the vWF type A-like domain is derived from a nonmammal, it has preferably at least about 75%, preferably at least about 80–85%, and most preferably at least about 90–95% or more sequence identity to SEQ ID NO:4 or SEQ ID NO:5. In a preferred embodiment, the biologically active portion of the protein which includes the vWF domain maintains one or more COCH5B2 activities. In a preferred embodiment, the biologically active portion includes at least one of the vWF type A-like domains of COCH5B2 as represented by amino acid residues 165 to 309 of SEQ ID NO:2 (as shown in SEQ ID NO:4) or amino acid residues 366 to 514 of SEQ ID NO:2 (as shown in SEQ ID NO:5). In another preferred embodiment, the domain is a factor C homologous domain derived from a human and has at least about 55%, preferably at least about 60–65%, even more preferably at least about 70–75% and most preferably at least about 80–90% or more sequence identity to SEQ ID NO:11. If the factor C homologous domain is derived from a nonmammal, it has preferably at least about 75%, preferably at least about 80–85%, and most preferably at least about 90–95% or more sequence identity to SEQ ID NO: 11. In a preferred embodiment, the biologically active portion of the protein which includes the factor C homologous domain maintains one or more COCH5B2 activities. In a preferred embodiment, the biologically active portion includes at least one factor C homologous domain of COCH5B2 as represented by amino acid residues 32–136 of SEQ ID NO:2 (as shown in SEQ ID NO:11). Moreover, other biologically active portions, in which other regions of the protein are deleted, can be prepared by recombinant techniques and evaluated for one or more of the activities described herein. Preferably, the biologically active portions of the COCH5B2 protein include one or more selected domains/motifs or portions thereof having biological activity.

COCH5B2 proteins are preferably produced by recombinant DNA techniques. For example, a nucleic acid molecule encoding the protein is cloned into an expression vector (as described above), the expression vector is introduced into a host cell (as described above) and the COCH5B2 protein is expressed in the host cell. The COCH5B2 protein can then be isolated from the cells by an appropriate purification scheme using standard protein purification techniques. Alternative to recombinant expression, a COCH5B2 protein, polypeptide, or peptide can be synthesized chemically using standard peptide synthesis techniques. Moreover, native COCH5B2 protein can be isolated from cells (e.g., cells of the inner ear), for example using an anti-COCH5B2 antibody (described further below).

The invention also provides COCH5B2 chimeric or fusion proteins. As used herein, a COCH5B2 "chimeric protein" or "fusion protein" includes a COCH5B2 polypeptide operatively linked to a non-COCH5B2 polypeptide. An "COCH5B2 polypeptide" refers to a polypeptide having an amino acid sequence corresponding to COCH5B2, whereas a "non-COCH5B2 polypeptide" refers to a polypeptide having an amino acid sequence corresponding to a protein which is not substantially homologous to the COCH5B2 protein, e.g., a protein which is different from the COCH5B2 protein and which is derived from the same or a different organism. Within the fusion protein, the term "operatively linked" is intended to indicate that the COCH5B2 polypeptide and the non-COCH5B2 polypeptide are fused in-frame to each other. The non-COCH5B2 polypeptide can be fused to the N-terminus or C-terminus of the COCH5B2 polypeptide. For example, in one embodiment the fusion protein is a GST-COCH5B2 fusion protein in which the COCH5B2 sequences are fused to the C-terminus of the GST sequences. Such fusion proteins can facilitate the purification of recombinant COCH5B2. In another embodiment, the fusion protein is a COCH5B2 protein containing a heterologous signal sequence at its N-terminus. In certain host cells (e.g., mammalian host cells), expression and/or secretion of COCH5B2 can be increased through use of a heterologous signal sequence.

Preferably, a COCH5B2 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. *John Wiley & Sons*: 1992). Moreover, many expression vectors are commercially available that already encode a fusion moiety (e.g., a GST polypeptide). A COCH5B2-encoding nucleic acid can be cloned into such an expression vector such that the fusion moiety is linked in-frame to the COCH5B2 protein.

The present invention also pertains to homologues of the COCH5B2 proteins which function as either a COCH5B2 agonist (mimetic) or a COCH5B2 antagonist. In a preferred embodiment, the COCH5B2 agonists and antagonists stimulate or inhibit, respectively, a subset of the biological activities of the naturally occurring form of the COCH5B2 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the COCH5B2 protein.

Homologues of the COCH5B2 protein can be generated by mutagenesis, e.g., discrete point mutation or truncation of the COCH5B2 protein. As used herein, the term "homologue" refers to a variant form of the COCH5B2 protein which acts as an agonist or antagonist of the activity of the COCH5B2 protein. An agonist of the COCH5B2 protein can retain substantially the same, or a subset, of the biological activities of the COCH5B2 protein. An antagonist of the COCH5B2 protein can inhibit one or more of the activities of the naturally occurring form of the COCH5B2 protein, by, for example, competitively binding to a downstream or upstream member of the COCH5B2 cascade which includes the COCH5B2 protein.

In an alternative embodiment, homologues of the COCH5B2 protein can be identified by screening combinatorial libraries of mutants, e.g., truncation mutants, of the COCH5B2 protein for COCH5B2 protein agonist or antagonist activity. In one embodiment, a variegated library of COCH5B2 variants is generated by combinatorial mutagenesis at the nucleic acid level and is encoded by a variegated gene library. A variegated library of COCH5B2 variants can be produced by, for example, enzymatically ligating a mixture of synthetic oligonucleotides into gene sequences such that a degenerate set of potential COCH5B2 sequences is expressible as individual polypeptides, or alternatively, as a set of larger fusion proteins (e.g., for phage display) containing the set of COCH5B2 sequences therein. There are a variety of methods which can be used to produce libraries of potential COCH5B2 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential COCH5B2 sequences. Methods for synthesizing degenerate oligonucleotides are known in the art (see, e.g., Narang, S. A., *Tetrahedron* 39:3, 1983; Itakura et al. *Annu. Rev. Biochem.* 53:323, 1984; Itakura et al., *Science* 198:1056, 1984; Ike et al., *Nucleic Acid Res.* 11:477, 1983.

In addition, libraries of fragments of the COCH5B2 protein coding can be used to generate a variegated population of COCH5B2 fragments for screening and subsequent selection of homologues of a COCH5B2 protein. In one embodiment, a library of coding sequence fragments can be generated by treating a double stranded PCR fragment of a COCH5B2 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the COCH5B2 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of COCH5B2 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify COCH5B2 homologues (Arkin and Yourvan, PNAS 89:7811–7815, 1992; Delgrave et al., *Protein Engineering* 6(3):327–331, 1993).

An isolated COCH5B2 protein, or a portion or fragment thereof, can be used as an immunogen to generate antibodies that bind COCH5B2 using standard techniques for polyclonal and monoclonal antibody preparation. The full-length COCH5B2 protein can be used or, alternatively, the invention provides antigenic peptide fragments of COCH5B2 for use as immunogens. The antigenic peptide of COCH5B2 includes at least 8 amino acid residues of the amino acid sequence shown in SEQ ID NO:2 or SEQ ID NO:7 and encompasses an epitope of COCH5B2 such that an antibody raised against the peptide forms a specific immune complex with COCH5B2. Preferably, the antigenic peptide includes at least 10 amino acid residues, more preferably at least 15 amino acid residues, even more preferably at least 20 amino acid residues, and most preferably at least 30 amino acid residues. Preferred epitopes encompassed by the antigenic peptide are regions of COCH5B2 that are located on the surface of the protein, e.g., hydrophilic regions.

A COCH5B2 immunogen typically is used to prepare antibodies by immunizing a suitable subject, (e.g., rabbit, goat, mouse or other mammal) with the immunogen. An appropriate immunogenic preparation can contain, for example, recombinantly expressed COCH5B2 protein or a chemically synthesized COCH5B2 peptide. The preparation can further include an adjuvant, such as Freund's complete or incomplete adjuvant, or similar immunostimulatory agent. Immunization of a suitable subject with an immunogenic COCH5B2 preparation induces a polyclonal anti-COCH5B2 antibody response.

Accordingly, another aspect of the invention features anti-COCH5B2 antibodies. The term "antibody" as used herein refers to immunoglobulin molecules and immunologically active portions of immunoglobulin molecules, i.e., molecules that contain an antigen binding site which specifically binds (immunoreacts with) an antigen, such as COCH5B2. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind COCH5B2. The term "monoclonal antibody" or "monoclonal antibody composition", as used herein, refers to a population of antibody molecules that contain only one species of an antigen binding site capable of immunoreacting with a particular epitope of COCH5B2. A monoclonal antibody composition thus typically displays a single binding affinity for a particular COCH5B2 protein with which it immunoreacts.

Additionally, recombinant anti-COCH5B2 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., *Science* 240:1041–1043, 1988; Liu et al., *PNAS* 84:3439–3443, 1987; Liu et al., *J. Immunol.* 139:3521–3526, 1987; Sun et al. *PNAS* 84:214–218, 1987; Nishimura et al., *Canc. Res.* 47:999–1005, 1987; Wood et al., *Nature* 314:446–449, 1985; and Shaw et al., *J. Natl. Cancer Inst.* 80:1553–1559, 1988); Morrison, S. L., Science 229:1202–1207, 1985; Oi et al., *BioTechniques* 4:214, 1986; Winter U.S. Pat. No. 5,225,539; Jones et al., *Nature* 321: 552–525, 1986; Verhoeyan et al., *Science* 239:1534, 1988; and Beidler et al., *J. Immunol.* 141:4053–4060, 1988.

An anti-COCH5B2 antibody (e.g., monoclonal antibody) can be used to isolate COCH5B2 by standard techniques, such as affinity chromatography or immunoprecipitation. An anti-COCH5B2 antibody can facilitate the purification of natural COCH5B2 from cells and of recombinantly produced COCH5B2 expressed in host cells. Moreover, an anti-COCH5B2 antibody can be used to detect COCH5B2 protein (e.g., in a cellular lysate or cell supernatant) in order to evaluate the abundance and pattern of expression of the COCH5B2 protein. Anti-COCH5B2 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

IV. Pharmaceutical Compositions

The COCH5B2 nucleic acid molecules, COCH5B2 proteins, COCH5B2 modulators, and anti-COCH5B2 antibodies (also referred to herein as "active compounds") of the invention can be incorporated into pharmaceutical compositions suitable for administration to a subject, e.g., a human. Such compositions typically include the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL☐ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a COCH5B2 protein or anti-COCH5B2 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., *PNAS* 91:3054–3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, modulators, and antibodies described herein can be used in one or more of the following methods: 1) drug screening assays; 2) diagnostic assays; and 3) methods of treatment. Diagnostic assays of the invention can also be used in fetal or neonatal diagnosis. A COCH5B2 protein of the invention has one or more of the activities described herein and can thus be used to, for example, treat or diagnose hearing disorders, e.g., DFNA9. The isolated nucleic acid molecules of the invention can be used to express COCH5B2 protein (e.g., via a recombinant expression vector in a host cell in gene therapy applications), to detect COCH5B2 mRNA (e.g., in a biological sample) or a genetic lesion in a COCH5B2 gene, and to modulate COCH5B2 activity, as described further below. In addition, the COCH5B2 proteins can be used to screen drugs or compounds which modulate COCH5B2 protein activity as well as to treat disorders characterized by insufficient production of COCH5B2 protein or production of COCH5B2 protein forms which have decreased activity compared to wild type COCH5B2. Moreover, the anti-COCH5B2 antibodies of the invention can be used to detect and isolate COCH5B2 protein and modulate COCH5B2 protein activity.

a. Drug Screening Assays:

The invention provides methods for identifying compounds or agents which can be used to treat disorders characterized by (or associated with) aberrant or abnormal EMI nucleic acid expression and/or COCH5B2 protein activity. These methods are also referred to herein as drug screening assays and typically include the step of screening a candidate/test compound or agent for the ability to interact with (e.g., bind to) a COCH5B2 protein, to modulate the interaction of a COCH5B2 protein and a target molecule, and/or to modulate COCH5B2 nucleic acid expression and/or COCH5B2 protein activity. Candidate/test compounds or agents which have one or more of these abilities can be used as drugs to treat disorders characterized by aberrant or abnormal EMI nucleic acid expression and/or COCH5B2 protein activity. Candidate/test compounds such as small molecules, e.g., small organic molecules, and other drug candidates can be obtained, for example, from combinatorial and natural product libraries.

In one embodiment, the invention provides assays for screening candidate/test compounds which interact with (e.g., bind to) COCH5B2 protein. Typically, the assays are cell-free assays which include the steps of combining a COCH5B2 protein or a biologically active portion thereof, and a candidate/test compound, e.g., under conditions which allow for interaction of (e.g., binding of) the candidate/test compound to the COCH5B2 protein or portion thereof to form a complex, and detecting the formation of a complex, in which the ability of the candidate compound to interact with (e.g., bind to) the COCH5B2 protein or portion thereof is indicated by the presence of the candidate compound in the complex. Formation of complexes between the COCH5B2 protein and the candidate compound can be quantitated, for example, using standard immunoassays.

In another embodiment, the invention provides screening assays to identify candidate/test compounds which modulate (e.g., stimulate or inhibit) the interaction (and most likely COCH5B2 activity as well) between a COCH5B2 protein and a molecule (target molecule) with which the COCH5B2 protein normally interacts. Examples of such target molecules includes proteins in the same signaling path as the COCH5B2 protein, e.g., proteins which may function upstream (including both stimulators and inhibitors of activity) or downstream of the COCH5B2 protein in the inner ear secretory pathway. Typically, the assays are cell-free assays which include the steps of combining a COCH5B2 protein or a biologically active portion thereof, a COCH5B2 target molecule (e.g., a COCH5B2 ligand) and a candidate/test compound, e.g., under conditions wherein but for the presence of the candidate compound, the COCH5B2 protein or biologically active portion thereof interacts with (e.g., binds to) the target molecule, and detecting the formation of a complex which includes the COCH5B2 protein and the target molecule or detecting the interaction/reaction of the COCH5B2 protein and the target molecule. Detection of complex formation can include direct quantitation of the complex by, for example, measuring inductive effects of the COCH5B2 protein. A statistically significant change, such as a decrease, in the interaction of the COCH5B2 and target molecule (e.g., in the formation of a complex between the COCH5B2 and the target molecule) in the presence of a candidate compound (relative to what is detected in the absence of the candidate compound) is indicative of a modulation (e.g., stimulation or inhibition) of the interaction between the COCH5B2 protein and the target molecule. Modulation of the formation of complexes between the COCH5B2 protein and the target molecule can be quantitated using, for example, an immunoassay.

To perform the above drug screening assays, it is desirable to immobilize either COCH5B2 or its target molecule to facilitate separation of complexes from uncomplexed forms of one or both of the proteins, as well as to accommodate automation of the assay. Interaction (e.g., binding of) of COCH5B2 to a target molecule, in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows the protein to be bound to a matrix. For example, glutathione-S-transferase/COCH5B2 fusion proteins can be adsorbed onto glutathione sepharose beads (Sigma Chemical, St. Louis, Mo.) or glutathione derivatized microtitre plates, which are then combined with the cell lysates (e.g. $_{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of COCH5B2-binding protein found in the bead fraction quantitated from the gel using standard electrophoretic techniques.

Other techniques for immobilizing proteins on matrices can also be used in the drug screening assays of the invention. For example, either COCH5B2 or its target molecule can be immobilized utilizing conjugation of biotin and streptavidin. Biotinylated COCH5B2 molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with COCH5B2 but which do not interfere with binding of the protein to its target molecule can be derivatized to the wells of the plate, and COCH5B2 trapped in the wells by antibody conjugation. As described above, preparations of a COCH5B2-binding protein and a candidate compound are incubated in the COCH5B2-presenting wells of the plate, and the amount of complex trapped in the well can be quantitated. Methods for detecting such complexes, in addition to those described above for the GST-immobilized complexes, include immunodetection of complexes using antibodies reactive with the COCH5B2 target molecule, or which are reactive with COCH5B2 protein and compete with the target molecule; as well as enzyme-linked assays which rely on detecting an enzymatic activity associated with the target molecule.

In yet another embodiment, the invention provides a method for identifying a compound (e.g., a screening assay) capable of use in the treatment of a disorder characterized by (or associated with) aberrant or abnormal COCH5B2 nucleic acid expression or COCH5B2 protein activity. This method typically includes the step of assaying the ability of the compound or agent to modulate the expression of the COCH5B2 nucleic acid or the activity of the COCH5B2 protein thereby identifying a compound for treating a disorder characterized by aberrant or abnormal COCH5B2 nucleic acid expression or COCH5B2 protein activity. Disorders characterized by aberrant or abnormal COCH5B2 nucleic acid expression or COCH5B2 protein activity are described herein. Methods for assaying the ability of the compound or agent to modulate the expression of the COCH5B2 nucleic acid or activity of the COCH5B2 protein are typically cell-based assays. For example, cells which are sensitive to ligands, which transduce signals via a pathway involving COCH5B2 can be induced to overexpress a COCH5B2 protein in the presence and absence of a candidate compound. Candidate compounds which produce a statistically significant change in COCH5B2-dependent responses (either stimulation or inhibition) can be identified. In one embodiment, expression of the COCH5B2 nucleic acid or activity of a COCH5B2 protein is modulated in cells and the effects of candidate compounds on the readout of interest (such as rate of cell proliferation or differentiation) are measured. For example, the expression of genes which are up- or down-regulated in response to a COCH5B2-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of COCH5B2 or COCH5B2 target molecules can also be measured, for example, by immunoblotting.

Alternatively, modulators of COCH5B2 expression (e.g., compounds which can be used to treat a disorder characterized by aberrant or abnormal COCH5B2 nucleic acid expression or COCH5B2 protein activity) can be identified in a method wherein a cell is contacted with a candidate compound and the expression of COCH5B2 mRNA or protein in the cell is determined. The level of expression of COCH5B2 mRNA or protein in the presence of the candidate compound is compared to the level of expression of COCH5B2 mRNA or protein in the absence of the candidate compound. The candidate compound can then be identified as a modulator of COCH5B2 nucleic acid expression based on this comparison and be used to treat a disorder characterized by aberrant COCH5B2 nucleic acid expression. For example, when expression of COCH5B2 mRNA or protein is greater (statistically significantly greater) in the presence of the candidate compound than in its absence, the candidate compound is identified as a stimulator of COCH5B2 mRNA or protein expression. Alternatively, when expression of COCH5B2 mRNA or protein is less (statistically significantly less) in the presence of the candidate compound than in its absence, the candidate compound is identified as an inhibitor of COCH5B2 mRNA or protein expression. The level of COCH5B2 mRNA or protein expression in the cells can be determined by methods described herein for detecting COCH5B2 mRNA or protein.

In yet another aspect of the invention, the COCH5B2 proteins can be used as "bait proteins" in a two-hybrid assay (see, e.g., U.S. Pat. No. 5,283,317; Zervos et al., *Cell* 72:223–232, 1993; Madura et al., *J. Biol. Chem.* 268: 12046–12054, 1993; Bartel et al., *Biotechniques* 14:920–924, 1993; Iwabuchi et al., *Oncogene* 8:1693–1696, 1993; and Brent WO94/10300), to identify other proteins, which bind to or interact with COCH5B2 ("COCH5B2-binding proteins" or "COCH5B2–bp") and modulate COCH5B2 protein activity. Such COCH5B2-binding proteins are also likely to be involved in the propagation of signals by the COCH5B2 proteins as, for example, upstream or downstream elements of the COCH5B2 pathway.

The two-hybrid system is based on the modular nature of most transcription factors, which consist of separable DNA-binding and activation domains. Briefly, the assay utilizes two different DNA constructs. In one construct, the gene that codes for COCH5B2 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a COCH5B2-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with COCH5B2.

Modulators of COCH5B2 protein activity and/or COCH5B2 nucleic acid expression identified according to these drug screening assays can be to treat, for example, hearing diseases or disorders, e.g., DFNA9. These methods of treatment include the steps of administering the modulators of COCH5B2 protein activity and/or nucleic acid expression, e.g., in a pharmaceutical composition as described in subsection IV above, to a subject in need of such treatment, e.g., a subject with hearing disease or disorder.

b. Diagnostic Assays:

The invention further provides a method for detecting the presence of COCH5B2 in a biological sample. The method involves contacting the biological sample with a compound or an agent capable of detecting COCH5B2 protein or mRNA such that the presence of COCH5B2 is detected in the biological sample. A preferred agent for detecting COCH5B2 mRNA is a labeled or labelable nucleic acid probe capable of hybridizing to COCH5B2 mRNA. The nucleic acid probe can be, for example, the full-length COCH5B2 cDNA of SEQ ID NO: 1 or SEQ ID NO:7, or a portion thereof, such as an oligonucleotide of at least 15, 30, 50, 100, 205, 210, 220, 250 or 500 nucleotides in length and sufficient to specifically hybridize under stringent conditions to COCH5B2 mRNA. A preferred agent for detecting COCH5B2 protein is a labeled or labelable antibody capable of binding to COCH5B2 protein. Antibodies can be polyclonal, or more preferably, monoclonal. An intact antibody, or a fragment thereof (e.g., Fab or $F(ab')_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect COCH5B2 mRNA or protein in a biological sample in vitro as well as in vivo. For example, in vitro techniques for detection of COCH5B2 mRNA include Northern hybridizations and in situ hybridizations. In vitro techniques for detection of COCH5B2 protein include enzyme linked immunosorbent assays (ELI- SAs), Western blots, immunoprecipitations and immunofluorescence. Alternatively, COCH5B2 protein can be detected in vivo in a subject by introducing into the subject a labeled anti-COCH5B2 antibody. For example, the antibody can be labeled with a radioactive marker whose presence and location in a subject can be detected by standard imaging techniques.

The invention also encompasses kits for detecting the presence of COCH5B2 in a biological sample. For example, the kit can include a labeled or labelable compound or agent capable of detecting COCH5B2 protein or mRNA in a biological sample; means for determining the amount of COCH5B2 in the sample; and means for comparing the amount of COCH5B2 in the sample with a standard. The compound or agent can be packaged in a suitable container. The kit can further include instructions for using the kit to detect COCH5B2 mRNA or protein.

The invention also encompasses kits for diagnosing patients affected with a hearing disorder, e.g., DFNA9. For example, the kit can include a probe or a primer, e.g., a labeled or labelable probe or primer, capable of detecting a genetic lesion, e.g., a point mutation, in a DNA sample obtained from a patient. The probe can be packaged in a suitable container. The probe or the primer is preferably derived from the factor C homologous region of COCH5B2 which contains COCH5B2 exons 4 and 5 and is approximately 100 amino acids in length. The kit can also include reagents required for PCR amplification and/or DNA sequencing. The kit can further include instructions for using the kit to diagnose a hearing disorder, e.g., DFNA9.

The methods of the invention can also be used to detect genetic lesions in a COCH5B2 gene, thereby determining if a subject with the lesioned gene is at risk for a disorder characterized by aberrant or abnormal COCH5B2 nucleic acid expression or COCH5B2 protein activity as defined herein. In preferred embodiments, the methods include detecting, in a sample, e.g. a DNA sample, from the subject, the presence or absence of a genetic lesion characterized by at least one of an alteration affecting the integrity of a gene encoding a COCH5B2 protein, or the misexpression of the COCH5B2 gene. For example, such genetic lesions can be detected by ascertaining the existence of at least one of 1) a deletion of one or more nucleotides from a COCH5B2 gene; 2) an addition of one or more nucleotides to a COCH5B2 gene; 3) a substitution of one or more nucleotides of a COCH5B2 gene, 4) a chromosomal rearrangement of a COCH5B2 gene; 5) an alteration in the level of a messenger RNA transcript of a COCH5B2 gene, 6) aberrant modification of a COCH5B2 gene, such as of the methylation pattern of the genomic DNA, 7) the presence of a non-wild type splicing pattern of a messenger RNA transcript of a COCH5B2 gene, 8) a non-wild type level of a COCH5B2-protein, 9) allelic loss of a COCH5B2 gene, and 10) inappropriate post-translational modification of a COCH5B2-protein. As described herein, there are a large number of assay techniques known in the art which can be used for detecting lesions in a COCH5B2 gene.

In certain embodiments, detection of the lesion involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080, 1988; and Nakazawa et al., *PNAS* 91:360–364, 1994), the latter of which can be particularly useful for detecting point mutations in the COCH5B2-gene (see Abravaya et al., *Nucleic Acids Res.* 23:675–682, 1995). This method can include the steps of collecting a sample of cells from a patient, isolating nucleic acid (e.g., genomic, mRNA or both) from the cells of the sample, contacting the nucleic acid sample with one or more primers which specifically hybridize to a COCH5B2 gene under conditions such that hybridization and amplification of the COCH5B2-gene (if present) occurs, and detecting the presence or absence of an amplification product, or detecting the size of the amplification product and comparing the length to a control sample.

In an alternative embodiment, mutations in a COCH5B2 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the COCH5B2 gene and detect mutations by comparing the sequence of the sample COCH5B2 with the corresponding wild-type (control) sequence. Examples of sequencing reactions include those based on techniques developed by Maxim and Gilbert (*PNAS* 74:560, 1977) or Sanger (*PNAS* 74:5463, 1977). A variety of automated sequencing procedures can be utilized when performing the diagnostic assays (Biotechniques 19:448, 1995), including sequencing by mass spectrometry (see, e.g., PCT International Publication No. WO 94/16101; Cohen et al., *Adv. Chromatogr.* 36:127–162, 1996; and Griffin et al., *Appl. Biochem. Biotechnol.* 38:147–159, 1993).

Other methods for detecting mutations in the COCH5B2 gene include methods in which protection from cleavage agents is used to detect mismatched bases in RNA/RNA or RNA/DNA duplexes (Myers et al., *Science* 230:1242, 1985); Cotton et al., *PNAS* 85:4397, 1988; Saleeba et al., *Meth. Enzymol.* 217:286–295, 1992), electrophoretic mobility of mutant and wild type nucleic acid is compared (Orita et al. *PNAS* 86:2766, 1989; Cotton, *Mutat Res* 285:125–144, 1993; and Hayashi, *Genet Anal Tech Appl* 9:73–79, 1992), and movement of mutant or wild-type fragments in polyacrylamide gels containing a gradient of denaturant is assayed using denaturing gradient gel electrophoresis (Myers et al, *Nature* 313:495, 1985). Examples of other techniques for detecting point mutations include, selective oligonucleotide hybridization, selective amplification, and selective primer extension.

Accordingly, mutation analysis of COCH5B2 was performed on three families with DFNA9 (FIG. 6). Initially, Southern blot analysis of the first kindred did not reveal any gross rearrangements of this gene. To look for mutations in all coding exons of COCH5B2 in DFNA9 patients, human genomic clones were isolated using cDNA probes. Genomic structure and intron-exon boundaries for COCH5B2 (FIG. 7A) were determined by sequencing genomic subclones with primers throughout the cDNA.

PCR primer pairs were designed in COCH5B2 introns and used to amplify exons and splice junctions from total genomic DNA from two DFNA9 individuals in each family and two controls. Amplified products were sequenced directly. Heterozygosity was discovered in three different nucleotides in the three kindreds, with one wild type allele and one mutated allele in all members tested with hearing loss: T☐G substitution at nucleotide position 253 in exon 4 in the first kindred, G☐A substitution at position 319 in exon 5 in the second kindred, and T☐C substitution at position 405 in exon 5 in the third kindred (FIG. 7). The three nucleotide changes cause missense mutations in COCH5B2, resulting in nonconservative amino acid substitutions of Val to Gly at codon 66 (GTA☐GGA) designated V66G, Gly to Glu at codon 88 (GGA☐GAA) designated G88E, and Trp to Arg at codon 117 (TGG☐CGG) designated W17R (FIG. 7). These residues are in close proximity to a cluster of cysteines near the amino terminus of COCH5B2. Yet another mutation was detected in two DFNA9 families in Netherlands and Belgium. A C☐T substitution at nucleotide 207 in exon 4 was detected in both kindreds resulting in a nonconservative amino acid substitution of Pro to Ser at codon 51 (CCA☐TCA). This residue is also in close proximity to a cluster of cysteines near the amino terminus of COCH5B2.

In all three families, genomic DNAs available from hearing and hearing-impaired members were amplified in the region of the nucleotide change and sequenced. In all cases, the mutated allele segregated with hearing-impaired individuals, showing heterozygosity for the mutation, consistent with an autosomal dominant mode of inheritance. All DNAs from hearing family members tested were homozygous for the wild type allele.

Additional molecular diagnostic testing was performed to confirm the missense mutations. For kindreds 1 and 3 (FIG. 6), allele-specific oligonucleotide (ASO) hybridization was performed on amplified genomic DNA from family members and 50 unrelated controls. There was complete concordance of the mutated oligonucleotide hybridization with hearing-impaired individuals and absence of hybridization in all control individuals. In kindred 2, G☐A substitution at position 319 results in the loss of an AvaII restriction site. AvaII restriction digests of amplified DNA from family members showed the loss of this restriction site by the presence of a predicted full-length amplified fragment (370 bp) in all members tested with hearing loss, as well as two smaller fragments (210 and 160 bp), products of digestion of the wild type. All hearing family members showed the presence only of the AvaII digested products, confirming two normal alleles in each individual. Similar restriction digest analysis on 50 unrelated control DNAs revealed 100 wild type alleles.

c. Methods of Treatment

Another aspect of the invention features methods for treating a subject, e.g., a human, having a disease or disorder characterized by (or associated with) aberrant or abnormal COCH5B2 nucleic acid expression and/or COCH5B2 protein activity. These methods include the step of administering a COCH5B2 modulator to the subject such that treatment occurs. The language "aberrant or abnormal COCH5B2 expression" refers to expression of a non-wild-type COCH5B2 protein or a non-wild-type level of expression of a COCH5B2 protein. Aberrant or abnormal COCH5B2 activity refers to a non-wild-type COCH5B2 activity or a non-wild-type level of COCH5B2 activity. As the COCH5B2 protein is involved in inner ear biology, aberrant or abnormal COCH5B2 activity or expression can interfere e.g., with the normal inner ear secretary pathway, e.g., it interfers with the production of acidophillic deposits. Non-limiting examples of disorders or diseases characterized by or associated with abnormal or aberrant COCH5B2 activity or expression include hearing diseases or disorders, e.g., DFNA9. Hearing disorders are disorders which detrimentally affect normal hearing function. Additional methods of the invention include methods for treating a subject having a disorder characterized by aberrant COCH5B2 activity or expression. These methods include administering to the subject a COCH5B2 modulator such that treatment of the subject occurs. The terms "treating" or "treatment", as used herein, refer to reduction or alleviation of at least one adverse effect or symptom of a disease or disorder, e.g., a disease or disorder characterized by or associated with abnormal or aberrant COCH5B2 protein activity or COCH5B2 nucleic acid expression.

As used herein, a COCH5B2 modulator is a molecule which can modulate COCH5B2 nucleic acid expression and/or COCH5B2 protein activity. For example, a COCH5B2 modulator can modulate, e.g., upregulate (activate) or downregulate (suppress), COCH5B2 nucleic acid expression. In another example, a COCH5B2 modulator can modulate (e.g., stimulate or inhibit) COCH5B2 protein activity. If it is desirable to treat a disease or disorder characterized by (or associated with) aberrant or abnormal (non-wild-type) COCH5B2 nucleic acid expression and/or COCH5B2 protein activity by inhibiting COCH5B2 nucleic acid expression, a COCH5B2 modulator can be an antisense molecule, e.g., a ribozyme, as described herein. Examples of antisense molecules which can be used to inhibit COCH5B2 nucleic acid expression include antisense molecules which are complementary to a portion of the 5' untranslated region of SEQ ID NO: 1 or SEQ ID NO: 7 which also includes the start codon and antisense molecules which are complementary to a portion of the 3' untranslated region of SEQ ID NO: 1 or SEQ ID NO:7. An example of an antisense molecule which is complementary to a portion of the 5' untranslated region of SEQ ID NO: 1 or SEQ ID NO:7 and which also includes the start codon is a nucleic acid molecule which includes nucleotides which are complementary to nucleotides 50–70 of SEQ ID NO: 1. An example of an antisense molecule which is complementary to a portion of the 3' untranslated region of SEQ ID NO: 1 is a nucleic acid molecule which includes nucleotides which are complementary to nucleotides 1740–1760 of SEQ ID NO: 1. An additional example of an antisense molecule which is complementary to a portion of the 3' untranslated region of SEQ ID NO: 1 is a nucleic acid molecule which includes nucleotides which are complementary to nucleotides 1800–1820 of SEQ ID NO: 1. A COCH5B2 modulator which inhibits COCH5B2 nucleic acid expression can also be a small molecule or other drug, e.g., a small molecule or drug identified using the screening assays described herein, which inhibits COCH5B2 nucleic acid expression. If it is desirable to treat a disease or disorder characterized by (or associated with) aberrant or abnormal (non-wild-type) COCH5B2 nucleic acid expression and/or COCH5B2 protein activity by stimulating COCH5B2 nucleic acid expression, a COCH5B2 modulator can be, for example, a nucleic acid molecule encoding COCH5B2 (e.g., a nucleic acid molecule comprising a nucleotide sequence homologous to the nucleotide sequence of SEQ ID NO: 1 or SEQ ID NO:7) or a small molecule or other drug, e.g., a small molecule (peptide) or drug identified using the screening assays described herein, which stimulates COCH5B2 nucleic acid expression.

Alternatively, if it is desirable to treat a disease or disorder characterized by (or associated with) aberrant or abnormal (non-wild-type) COCH5B2 nucleic acid expression and/or COCH5B2 protein activity by inhibiting COCH5B2 protein activity, a COCH5B2 modulator can be an anti-COCH5B2 antibody or a small molecule or other drug, e.g., a small molecule or drug identified using the screening assays described herein, which inhibits COCH5B2 protein activity. If it is desirable to treat a disease or disorder characterized by (or associated with) aberrant or abnormal (non-wild-type) COCH5B2 nucleic acid expression and/or COCH5B2 protein activity by stimulating COCH5B2 protein activity, a COCH5B2 modulator can be an active COCH5B2 protein or portion thereof (e.g., a COCH5B2 protein or portion thereof having an amino acid sequence which is homologous to the amino acid sequence of SEQ ID NO:2, SEQ ID NO:6 or a portion thereof) or a small molecule or other drug, e.g., a small molecule or drug identified using the screening assays described herein, which stimulates COCH5B2 protein activity.

In addition, a subject having a hearing disorder can be treated according to the present invention by administering to the subject a COCH5B2 protein or portion or a nucleic acid encoding a COCH5B2 protein or portion thereof such that treatment occurs.

Other aspects of the invention feature methods for modulating a cell associated activity. These methods include contacting the cell with an agent (or a composition which includes an effective amount of an agent) which modulates COCH5B2 activity or COCH5B2 expression such that a cell associated activity is altered relative to a cell associated activity of the cell in the absence of the agent. As used herein, "a cell associated activity" refers to a normal or abnormal activity or function of a cell. Examples of cell associated activities include cell—cell adhesion or cell/extracellular matrix interaction. The term "altered" as used herein refers to a change, e.g., an increase or decrease, of a cell associated activity. In one embodiment, the agent stimulates COCH5B2 protein activity or COCH5B2 nucleic acid expression. Examples of such stimulatory agents include an active COCH5B2 protein, a nucleic acid molecule encoding COCH5B2 that has been introduced into the cell, and a modulatory agent which stimulates COCH5B2 protein activity or EMI nucleic acid expression and which is identified using the drug screening assays described herein. In another embodiment, the agent inhibits COCH5B2 protein activity or COCH5B2 nucleic acid expression. Examples of such inhibitory agents include an antisense COCH5B2 nucleic acid molecule, an anti-COCH5B2 antibody, and a modulatory agent which inhibits COCH5B2 protein activity or COCH5B2 nucleic acid expression and which is identified using the drug screening assays described herein. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject, e.g., a mammal, e.g., a human, and the subject has a disorder or disease characterized by or associated with abnormal or aberrant COCH5B2 activity or expression.

A nucleic acid molecule, a protein, a COCH5B2 modulator etc. used in the methods of treatment can be incorporated into an appropriate pharmaceutical composition described herein and administered to the subject through a route which allows the molecule, protein, modulator etc. to perform its intended function. Examples of routes of administration are also described herein under subsection IV.

This invention is further illustrated by the following examples which should not be construed as limiting. The contents of all references, patent applications, patents, and published patent applications cited throughout this application are hereby incorporated by reference.

EXAMPLES

Materials and Methods

Isolation of cDNAs

To obtain full length cDNA sequence of hCOCH5B2, a human fetal brain cDNA library cloned in the Lambda Zap II vector (Stratagene, La Jolla, Calif.) was screened using a hCOCH5B2 probe approximately 600 bp in size (ending at the first polyadenylation site), which we had originally isolated by subtractive hybridization and differential screening. Although hCOCH5B2 is expressed at a very low level in the brain, this library was chosen because it is a mixture of oligo(dT)-and random-primed cDNAs and is more likely to contain 5' ends of cDNAs.

Approximately 106 recombinant phage were screened using standard techniques. Filters were prehybridized at 42□ C. and then hybridized with 32P-labeled random-primed (Feinberg and Vogelstein, *Anal. Biochem.* 137:266–267, 1984) 600-bp hCOCH5B2 probe and again with a cDNA probe approximately 580 bp from the most 5' region of the cDNAs from the first screening, at 42□ C. for 48 h in 10% dextran sulfate, 4×SSC, 7 mM Tris-Hcl (pH 7.6), 0.8× Denhardt's solution, 200 □g/ml sonicated herring sperm DNA, 40% formamide, and 0.5% SDS. Filters were washed in 0.1×SSC, 0.1% SDS at 50□ C., prior to autoradiography using XAR-5 film (Eastman Kodak Co., Rochester, N.Y.) and intensifying screens at −800C. Following discovery of several cloning artifacts in this library, we then screened our original human fetal cochlear cDNA library. Filters were probed with a PCR-generated 32P-labeled probe of approximately 230 bp using oligonucleotides GAT-TGTAAAGCAGACATTGC (SEQ ID NO:12) and ACCTACTTCCTTATGGC (SEQ ID NO:13) from the most 5' region of the available hCOCH5B2 cDNA. PCR was performed in 1× reaction buffer (Perkin-Elmer Cetus, Norwalk, Conn.); 0.8 OM each primer; 0.2 mM each dATP; and 1.25 units of Taq DNA polymerase. An initial denaturation was done at 94□ C. for 4 min, followed by 30 cycles of denaturation at 94□ C. for 1 min, annealing at 55□ C. for 30 s, extension at 720□ C. for 1 min 30 s, and a final extension at 72□ C. for 7 min.

To obtain the 5' end sequence of hCOCH5B2, we performed a final screening of our newly constructed human fetal cochlear CapFinder (Clontech, Palo Alto, Calif.) cDNA library (see below) was performed using a probe generated from the same oligonucleotides and in the same manner as the previous screening.

To clone the mouse homolog of hCOCH5B2, a postnatal day 20 mouse oligo (dT)-primed brain cDNA library constructed in Uni-ZAP XR (Stratagene) was screened with the 600-bp hCOCH5B2 32P-labeled random-primed cDNA probe in the manner described above.

Construction of Human Fetal Cochlear CapFinder cDNA Library

Total cellular RNAs were extracted (Chirgwin et al., *Biochemistry* 18:5294–5299, 1979) from cochlea (membranous labyrinths) obtained from human fetuses at 18–22 weeks developmental age, in accordance with guidelines established by the Human Research Committee at the Brigham and Women's Hospital. Small aliquots of these RNAs were run on denaturing agarose gels to assess RNA quality. Only samples without degradation were pooled for library construction. Poly(A)$^+$ RNAs were selected (Aviv and Leder, 1972) and used to construct a CapFinder (Clontech) long-distance PCR-based cDNA library, cloned into the Lambda Zap II vector (Stratagene). The oligo(dT) primer, high-fidelity, long-reading DNA polymerase, and a unique CapSwitch oligonucleotide are designed to select for 5' cap of RNAs and to enrich for large, full-length cDNAs in this library.

Isolation of Genomic Clones

A human male placenta genomic library in Lambda FIX II (Stratagene) was screened in the same manner as the cDNA library, with a PCR-generated, 32P-labeled hCOCH5B2 544-bp cDNA probe (ending at the first polyadenylation site) using oligonucleotides GGGCAGTC-CTATGATGATGT (SEQ ID NO: 14) and GCTATG-GAATTTGCATATCT (SEQ ID NO: 15), for isolation of genomic clones to be used as probes for FISH mapping.

Nucleotide Sequence Analysis

Nucleotide sequence of clones was determined by the dideoxy chain termination method (Sanger et al., *Proc. Natl. Acad. Sci. USA* 74:5463–5467, 1977), using an ABI fluorescent DNA sequencing apparatus (Applied Biosystems, Foster City, Calif.). Sequence analysis was performed using the University of Wisconsin Genetics Computer Group software (Devereux et al., *Nucleic Acids Res.* 12:387–395, 1984). comparison of sequences to those deposited in nucleotide and peptide databases was performed using the BLAST Network Service of the National Center for Biotechnology Information (Altschul et al., *J. Mol. Biol.* 215: 403–410, 1990).

Northern Blot Analysis

Total cellular RNAs were extracted (Chirgwin et al., *Biochemistry* 18:5294–5299, 1979) from second-trimester human fetal tissues, including membranous labyrinths (cochlea), vestibule, brain (cerebrum), spleen, and thymus and from human adult tissues, including brain (cerebrum), cerebellum, spinal cord, spleen, lymph node, lung, skeletal muscle, and skin. All human tissues were obtained in accordance with guidelines established by the Human Research Committee at Brigham and Women's Hospital. Human adult tissues were obtained from autopsies, except for the adult human spleen that was obtained from an individual with non-Hodgkin's lymphoma with splenomegaly, containing both normal and neoplastic cells. Total RNAs were extracted from normal mouse adult tissues including brain (cerebrum), cerebellum, spleen, thymus, heart, lung, liver, kidney, small intestine, large intestine, testis, cartilage, skeletal muscle, eye, retina, sclera, and choroid. Ten micrograms of each of the RNAs was electrophoresed in denaturing 1% agarose-formaldehyde gels and transferred to GeneScreen (DuPont, Wilmington, Del.) filters (Thomas, *Proc. Natl. Acad. Sci. USA* 77:5201–5205, 1980). After transfer, ethidium bromide-stained RNAs were visualized on filters to confirm integrity, concentration, and even transfer of RNAs. Filters were prehybridized for 2–4 h and hybridized overnight at 42□ C., in the same solution as described above, with 32P-labeled probes (Feinberg and Vogelstein, *Anal. Biochem.* 137:266–267, 1984) corresponding to the 600-bp hCOCH5B2 cDNA, a composite of the full-length hCOCH5B2 cDNAs, hCOCH5B2 cDNA of approximately 750 bp from only the region beyond the first polyadenylation site, and the full-length mouse COCH5B2 cDNA. Filters were washed in 0.1% SDS in 0.1×SSC at 42–55° C. prior to autoradiography using XAR-5 film with intensifying screens at −80□C.

Gene Mapping

Somatic cell hybrid mapping of human COCH5B2. DNAs from the NIGMS human/rodent somatic cell hybrid mapping panel 1 (Drwinga et al., *Genomics* 16:311–314, 1993), consisting of 18 hybrids retaining from 1 to 19 human chromosomes, were digested with EcoRI, electrophoresed in a 0.8% agarose gel, and transferred to Genescreen (DuPont) as described (Southern, J. Mol. Biol. 98:503–517, 1975). The filter was hybridized with $^{32}$P-labeled 600-bp original hCOCH5B2 cDNA probe and washed at 42□ C. as described above. The panel was scored for presence or absence of a human COCH5B2 hybridizing band to determine concordance or discordance with the reported human chromosome in each hybrid.

Fluorescence In Situ hybridization (FISH) of hCOCH5B2. A hCOCH5B2 cDNA of approximately 1.6 kb (ending at the second polyadenylation site) and a human genomic clone of approximately 16–18 kb in length corresponding to hCOCH5B2 were used separately as probes for FISH. Probes were labeled with digoxigenin-11-dUTP (Boehringer Mannheim, Indianapolis, Ind.) using dNTPs obtained from the same manufacturer and the DNase I/DNA polymerase I mixture from the BioNick Labeling System Gibco BRL, Gaithersburg, Md.). DNA was coprecipitated with 5 □g of Cot-I DNA (Gibco BRL) and resuspended in 1×TE at 100 □g/ml.

Hybridization of metaphase chromosome preparations from peripheral blood lymphocytes obtained from normal human males was performed with the labeled hCOCH5B2 probe at a concentration of 7.5 □g/ml in Hybrisol VI as previously described (Ney et al., *Mol. Cell. Biol.* 13:5604–5612, 1993). Digoxigenin-labeled probe was detected using reagents supplied in the Oncor Kit (Oncor, Gaithersburg, Md.) according to the manufacturer's recommendations. Metaphase chromosomes were counterstained with 4,6-diamidino-2-phenylindole dihydrochloride (DAPI) (Oncor). Map position of the labeled hCOCH5B2 probe was determined by visual inspection of the fluorescent signal on the DAPI-stained metaphase chromosomes. Hybridization was observed with a Zeiss Axiophot microscope and photographs were prepared using the CytoVision Imaging System (Applied Imaging, Pittsburgh, Pa.).

Mapping the murine homolog of hCOCH5B2. Segregation of COCH5B2 was compared with that of marker loci previously typed in a panel of DNAs derived from progeny of matings between female (C57BL/6JxCAST/Ei)F1 hybrids and male C57BL/6J. The panel consists of 144 samples that have been characterized for more than 300 loci (Johnson et al., *Mamm. Genome* 5:670–687, 1994). Restriction fragment length variants between the parental strains were detected with the hCOCH5B2 cDNA approximately 600 bp in size.

Genetic linkage of mCOCH5B2 was detected with markers on mouse chromosome 12. Gene order was determined by minimizing meiotic crossover events using the computer program Map Manager (Manly, *Mamm. Genome* 4:303–313, 1993).

Identification of YACs containing hCOCH5B2 and markers linked to DFNA9. A series of overlapping YACs from a contig spanning the region of DFNA9 and of hCOCH5B2 were obtained from Research Genetics, Inc. (Huntsville, Ala.). These six YACs are 748-D-11, 888-C-6, 949-A-9, 925-C-2, 746-F-10, and 964-F-6. Primers corresponding to STS markers D14S49, D14S121, and D14S54, which have high lod scores for linkage to DFNA9 (Manolis et al., *Hum. Mol. Genet.* 5:1047–1050, 1996), were also obtained from Research Genetics. PCR was performed on the six YACs using primers from the DFNA9 markers as well as hCOCH5B2 primers CATCAGAGGCAGCATTTGTA (SEQ ID NO:16) and TTGTAACCAGAAGGCAGC (SEQ ID NO:17) to assess localization.

In situ hybridization

In situ hybridization with digoxigenin-labeled COCH5B2 antisense riboprobe on cryosections was conducted by a modification of a published protocol (N. Schaeren-Wiemers and A. Gerfin-Moser, Histochemistry 100:421, 1993). 14-mm frozen sections were cut with a cryomicrotome (CM3000, Leica), collected on silyated slides (PGC Scientific), dried at 37□ C. for 45 min, and stored frozen at −70° C. until use. For hybridization, sections were brought to room temperature, rehydrated in 100 ml diluted formamide (1:100) in 50% (v/v) formamide, 10% (w/v) dextran sulfate, 1 mg/ml yeast-RNA, 1× Denhardt's solution, 185 mM NaCl, 5.6 mM NaH2PO4, 5 mM Na2HPO4, 5 mM EDTA, and 15 mM Tris at pH 7.5 and incubated overnight at 65° C. After washing and immunological detection with alkaline phosphatase-conjugated anti-digoxigenin Fab fragments (Boehringer Mannheim), the sections were overlaid with nitro blue tetrazolium chloride and 5-bromo-4-chloro-3-indolyl-phosphate substrate (1-STEP NBT/BCIP, Pierce), covered, and incubated overnight at room temperature in a humidified chamber. The color reaction was stopped with PBS and slides were mounted in 50% (v/v) glycerol in PBS. Photography was performed with a MC80 camera on an Axiovert 135 microscope (Carl Zeiss) using Ektachrome 160T (Kodak).

Linkage Analysis

For linkage analysis, two point lod scores were performed using the program MLINK (version 5.1), assuming a penetrance of 1.0 and an allele frequence <0.01 based on allele frequencies derived from 50 unrelated individuals. COCH5B2 markers were used to determine linkage in family 1 Su and 1 St.

Clinical Evaluations

Clinical evaluations of individuals in the DNA9 families was based on a questionnaire (to assess other known causes and risk factors for hearing loss), history, and a comprehensive otolaryngologic evaluation (exam, audiogram, and vestibular testing). All studies were reviewed by and conducted in accordance with Institutional Review Board Policy of the Massachusetts Eye and Ear Infirmary.

Southern Blot Analysis

Five mg of total genomic DNAs were digested with BamHi, EcoRI, HindIII and PstI, electrophorised in 0.8% agarose gels, and transferred to Genescreen (DuPont) as described in E. M. Southern, *J. Mol. Biol.* 98:503, 1975. Filters were hybridized with 32P-labeled COCH5B2 probes spanning exons 7–12 and washed as described above.

Determination of Intron-Exon Bounderies for COCH5B2

A human placenta genomic library in Lambda FIX (Stratagene) was screened as described above with a probe from COCH5B2 exons 11–12 and subsequently with a probe spanning exons 1–8. Genomic clones were subcloned and sequenced with an ABI fluorescent DNA sequencing apparatus (Applied Biosystems) using primers throughout COCH5B2 cDNA.

Mutational Analysis

Sequence varians in family 1W and 1 St were confirmed by PCR-amplification of exons and oligonucleotide-specific hybridization as described in Benson et al., *Circulation* 93:1791, 1996. Amplified products were transferred to nylon membranes (Gene Screen Plus) in duplicate and hybridized separately with 32P-labeled wild-type (family 1W: 5'-AA-CATAGTATATGC-3' (SEQ ID NO: 18); family 1St: 5'-TTCTAGACGGTCTG-3'(SEQ ID NO: 19)) oligonucleotides. Membranes were washed in 6×SSC, 0.05% sodium pyrophosphate (39° C. for family 1W and 48° C. for family 1 St) and hybridization signals quantified using a Phosphor Imager (Molecular Dynamics).

RESULTS

Analysis of Human and Mouse Sequences

The original hCOCH5B2600-bp cDNA was obtained by subtractive hybridization and differential screening of our human fetal cochlear cDNA library (Robertson et al., *Genomics* 23:42–50, 1994). A subsequent number of screenings yielded a composite of several overlappng cDNAs, showing an alternate polyadenylation site approximately 480 bp downstream of the first polyadenylation site. The hCOCH5B2 cDNA was also used to screen a mouse fetal brain cDNA library yielding two full-length clones with two different polyadenylation signals approximately 440 bp apart, consistent with transcript sizes detected on Northern blots. The nucleotide sequences of the human and mouse COCH5B2 have been deposited in the nucleotide databases under Accession Nos. AF006740 and AF006741, respectively.

Comparison of human and mouse COCH5B2 reveals 89% identity in the nucleotide sequences in the regions of the open reading frame (ORF). This homology drops abruptly after the translation stop codon, indicating lack of conservation in the 3' untranslated region of the gene. The hCOCH5B2 sequence shows an ORF of 550 amino acid residues (FIG. 1); the mCOCH5B2 sequence shows an ORF of 552 amino acids (FIG. 2). There is only one gap of 2 amino acids between the human and mouse sequences, which appears at the very amino terminus, with the human sequence showing 4 leucine repeats as opposed to 6 in the mouse. The human and mouse sequences show a very high degree of conservation: 94% identity of amino acids and 96% similarity, taking into account conservative amino acid changes (FIG. 3).

The COCH5B2 sequences of both human and mouse show a start methionine that conforms to the Kozak rules of translation initiation in eukaryotes (Kozak, Nucleic Acids Res. 15:8125–8148, 1987). Analysis of the most amino-terminal portion of both the human and the mouse COCH5B2 reveals a potential signal peptide that fits von Heijne's rules for signal peptides and their potential cleavage sites (von Heijne, Nucleic Acids Res. 14:4683–4690, 1986). The lowest degree of amino acid conservation between the human and the mouse sequences is seen in this region (FIG. 3), which would be cleaved off in forming the mature protein. The predicted proteolytic cleavage site would be at residue 26 and 28 in the human and the mouse, respectively. A stretch of hydrophobic residues (four leucines in the human and six leucines in the mouse) is present in this potential signal peptide. This region is also the most hydrophobic portion of the whole sequence, according to analysis by the Kyte-Doolittle hydrophobicity plot (Kyte and Doolittle, *J. Mol. Biol.* 157:105–132, 1982).

Consistent with the prediction of a secreted protein as indicated by the presence of a potential signal peptide in COCH5B2 are the absence of a transmembrane region and the presence of two domains with homology to the von Willebrand factor (vWF) type A domain (FIG. 4). Type A domains are regions of approximately 200 amino acid residues in length, often present in multiple numbers (and sometimes in tandem) within a single protein. A superfamily of genes with type A-like domains or "modules" includes proteins, all with ligand-binding properties, involved in various functions such as homeostasis (vWF), the complement system (C2 and Factor B), the immune system (integrins such as LFA-1, Mac-1, VLA-1, VLA-2, p150, and 95), and the extracellular matrix (cartilage matrix protein and collagens type VI, VII, XII, and XIV) (reviewed in Colombatti and Paolo *Matrix* 77:2305–2315, 1991; Colombatti et al., *Matrix* 13:297–3061993). With the exception of the integrins, which are transmembrane proteins, the only molecules known to date to contain type A-like domains are secreted proteins. Moreover, the highest number of type A-like domains known to date are found in the extracellular matrix (ECM), in proteins such as Col VIα3, which has 11 type A-like modules, which make up almost all of the protein (Bonaldo et al., *Bio-chemistry* 29:1245–1254, 1990).

FIG. 4 shows the sequence similarity of the two vWF type A-like domains of hCOCH5B2 to each other and to one of the type A-like domains of the following: human collagen 12α1 (COL12A1), VA module (Gerecke et al., *Genomics* 41:236–242, 1997); human cartilage matrix protein (CMP), A1 module (Jenkins et al., *J. Biol. Chem.* 265:19624–19631, 1990); and human vWF, A3 module (Mancuso et al., *Bio-chemistry* 30:253–269, 1991). Not shown in FIG. 2 are type A domains of a number of other genes that also have a high degree of homology to type A domains of COCH5B2, such as collagens :type V (Bonaldo et al., *J. Biol. Chem,* 264: 5575–5580, 1989, Biochemistry 29:1245–1254, 1990; Koller et al., *EMBO J.* 8:1073–10771989), VII (Parente et al., *Proc. Natl. Acad. Sci. USA* 88:6931–6935, 199i; Christiano et al., *J. Biol. Chem.* 269:20256–20262, 1994), and XIV (Wälchli et al., *Eur. J. Biochem.* 212:483–490, 1993). These collagens are all nonfibrillar collagens, types XII and XIV being defined as members of the FACIT (fibril-associated collagens with interrupted triple helices) family of collagens (Olsen et al., *Trends Glycosci. Glycotech* 7:115–127, 1995). All of these "collagens" are hybrid molecules that have relatively short collagenous domains consisting of Gly-X—Y repeats, in addition to larger noncollagenous domains, including the vWF type A modules. COCH5B2 lacks any collagenous domain and is therefore not a collagen, unlike a novel inner ear-specific collagen found in fish (Davis et al., *Science* 267:1031–1034, 1995). Furthermore, COCH5B2 also lacks "fibronectin type III" repeats, which are regions of homology to fibronectin with cell-binding properties present in some collagens that also have vWF type A domains (Colombatti et al., *Matrix* 13:297–306, 1993).

CMP (Agraves et al., *Proc. Natl. Acad. Sci. USA* 84:464–468, 1987; Jenkins et al., *J. Biol. Chem.* 265: 19624–19631, 1990), a major component of the ECM o-nonarticular cartilage, consisting of approximately 500 amino acid residues, shows some structural similarities to COCH5B2. It possesses two vWF A domains separated by a small EGF-like region in the absence of a collagenous domain or fibronectin III repeats. Another similarity in structure between COCH5B2 and CMP resides in the position of cysteine residues that are immediately adjacent to the amino and carboxyl termini of each of the type A domains (FIG. 5). There are no cysteine residues within the type A domain itself. This same pattern of cysteines flanking but not within the type A domains is also seen in collagens type XII and XIV (Colombatti et al, *Matrix* 13:297–306, 1993). In CMP, it has been shown that the 2 cysteine residues flanking the A2 domain form an intramolecular disulfide bond, in addition to the intermolecular disulfide bonds formed between the cysteine residues outside the A domains for trimerization of CMP (Haudenschild et al., *J. Biol.* 270: 23150–23154, 1995). Similar disulfide bonds may exist in COCH5B2 between the 2 cysteine residues flanking the type A domains, in addition to a cluster of cysteines in the amino terminus of the sequence and 2 cysteines in the short intervening sequence between the two type A domains (FIG. 5).

Type A domains of various proteins are thought to mediate a variety of interactions between components of the ECM, cell-ECM interactions, cell—cell adhesion, and cell membrane receptor and soluble factor interactions via binding of the type A domain to proteins such as fibrillar collagens, hyaluronic acid, glycoprotein GpIb, heparin, and complement fragment iC3B, as reviewed by Colombatti et al. (*Matrix* 13:297–306, 1993). The type A domains of von Willebrand factor have been shown to bind to fibrillar collagens types I and III (Roth et al., *Bioichemistry* 25:8357–8361, 1986; Kalafatis et al., *Blood* 70:1577–1583, 1987; Pareti et al., *J. Biol. Chem.* 262:13835–13841, 1987). Other collagens, types VI, XII, and XIV, and CMP are also thought to bind fibrillar collagens as a bridging role in ECM assembly and stabilization (Colombatti et al., *Matrix* 13:297–306, 1993). Interestingly, we have previously shown that the cochlea expresses very high levels of COL1A2 and COL3A1 (levels comparable to COCH5B2) (Robertson et al., *Genomics* 23:42–50, 1994). It is possible that COCH5B2 may interact via type A domains with the abundant fibrillar collagens for ECM assembly in the cochlea, where function is so tightly dependent on the highly structured architecture of this sensory organ.

Expression Pattern in Human and Mouse

Very high levels of hCOCH5B2 mRNA were detected only in human fetal cochlea and very low levels in human fetal brain and eye, among a large panel of fetal tissues tested (Robertson et al., *Genomics* 23:42–50, 1994). Human adult tissues including brain, cerebellum, spinal cord, spleen, lymph node, lung, skeletal muscle, and spleen has also been analyzed. High levels of hCOCH5B2 mRNA were not detected in any of the adult human tissues tested, findings consistent with those in fetal tissues. Low levels of hCOCH5B2 message were detected in human adult muscle.

In addition, hCOCH5B2 expression in human fetal vestibule was studied. Very high level of expression of hCOCH5B2 is seen in the vestibule, comparable only to the level in the cochlea. This finding is interesting in that these two organs have developmental, anatomical, and functional similarities and that cochlear and vestibular dysfunction may be found together frequently both in mice and in humans. In particular, a human deafness disorder, DFNA9 (Manolis et al., *Hum. Mol. Genet.* 5:1047–1050, 1996) has associated vestibular findings. Temporal bone sections from individuals affected with DFNA9 show accumulation of acidophilic deposits obstructing the cochlear and vestibular nerve channels, causing severe degeneration of dendrites and atrophy of cochlear and vestibular sense organs (Khetarpal et al., *Arch. Otolaryngol. Head Neck Surg.* 117:1032–1042, 1991; Khetarpal, *Arch. Otolaryngol. Head Neck Surg.* 119:106–108, 1993).

Northern blot analysis of a panel of adult mouse tissues reveals messages of approximately 2.0 and 2.5 kb, consistent in size with the two mouse cDNAs, with the two polyadenylation sites in the mouse, and approximately with two of three human messages. The larger band in the mouse is approximately 2.5 kb, migrating slightly higher than the predominant human message of approximately 2.3 kb. Three messages approximately 2.0, 2.3, and 2.9 kb in size are seen in the human. Northern analysis using a probe derived from the 3' portion of hCOCH5B2 cDNA, excluding any sequence 5' of the first polyadenylation site, shows hybridization only to the largest of the three hCOCH5B2 transcripts in the cochlea, indicating that the second polyadenylation site is responsible for the largest hCOCH5B2 mRNA. The majority of our isolated cDNAs (8 of 10) possesses the first polyadenylation site, corresponding most likely to the middle-sized and the most predominant (highest level) of the three hCOCH5B2 transcripts. The smallest hCOCH5B2 mRNA may also be the result of usage of a different (more 5') polyadenylation site (although not yet seen in any of our isolated clones) or may be a product of alternative splicing, exon skipping, differential use of promoter cap sites, or a different related gene. Alternative splicing has been reported in the vWF A-like domains of collagen VI α 3 (Doliana et al., *J. Cell Biol.* 111:2197–2205, 1990).

The expression pattern in adult mouse differs from that in fetal and adult human. COCH5B2 is expressed abundantly in adult mouse spleen, at moderate levels in cerebrum, cerebellum/medulla, and thymus, and at low levels in eye and lung. High and moderate levels of mCOCH5B2 mRNA are seen in a wider variety of mouse tissues in contrast to a more specific cochlear and vestibular expression in the human. Notably, the mouse spleen expresses COCH5B2 at a high level, whereas no expression is detectable in human fetal and adult spleen. This difference remains to be elucidated but may reflect the function of the spleen in hematopoiesis in the mouse compared to the human. Different expression patterns of COCH5B2 in human and mouse may indicate some difference in the function of this gene in the two species and/or may be responsible for different disease phenotypes in the same mutated gene in the two species.

In both species, very low level of COCH5B2 expression is detected in the eye. Expression of COCH5B2 in the eye is of particular interest due to the finding of numerous disorders that affect both the auditory and the visual systems, such as the heterogeneous Usher syndrome (Fishman et al., *Arch. Ophthalmol.* 101:1367–1374, 1983). We have looked at the sensorineural portion vs. the connective tissue and supportive portion of the eye by Northern analysis: expression of mCOCH5B2 is high in mouse retina and very low to undetectable in sclera and choroid.

Mapping in Human

Physical mapping of hCOCH5B2 may point toward a region of the human genome to which human deafness disorders have been mapped and may provide a positional candidate for the disorder. hCOCH5B2 was localized to human chromosome 14 by Southern blot of the NIGMS human/rodent somatic cell hybrid panel 1 (Drwinga et al., *Genomics* 16:311–314, 1993) probed with a 600-bp hCOCH5B2 cDNA. A human-specific hybridizing band of approximately 5.7 kb in size was detected. Hybridizing bands to mouse and hamster genomic DNA, approximately 8.1 and 3.3 kb, respectively, were also detected, showing the evolutionary conservation of this gene. Map assignment was done on the basis of lowest percentage of discordancy (6%) of segregation of the hCOCH5B2 hybridizing band with human chromosome 14 in 18 somatic cell hybrids. The hybrid cell line in which a hCOCH5B2-hybridizing band could not be detected shows only 2% of the cells examined to have retained chromosome 14. It is possible that this level was below the sensitivity of detection of our Southern blot.

For a more precise map assignment, fluorescence in situ hybridization was performed. Map position was determined by visual inspection of the fluorescent hybridization signals on DAPI-stained metaphase chromosomes. When a human COCH5B2 cDNA probe of approximately 1.6 kb was used, signal was detected on the long arm of chromosome 14 in band q11.2–q13 in 20 metaphase preparations. In 3 metaphases, signal was detected on both chromosomes 14. This map assignment was confirmed by performing FISH using a hCOCH5B2 genomic clone of approximately 16–18 kb in size. In 10 of 12 metaphase preparations analyzed, hybridization signal was present on q11.2–q13, in 9 metaphase spreads, both copies of chromosome 14 were labeled, and in 1 metaphase spread, signal was detected on one chromosome 14. (The official Human Gene Mapping nomenclature for hCOCH5B2 is D14S564E, GDB Accession No. G00–335-416).

Of particular interest is a nonsyndromic deafness disorder, DNFA9, a nonsyndromic autosomal dominant sensorineural hearing loss with vestibular defects (Khetarpal et al., *Arch. Otolaryngol. Head Neck Surg.* 117:1032–1042, 1991; Khetarpal, *Arch. Otolaryngol. Head Neck Surg.* 119:106–108, 1993; Manolis et al., *Hum. Mol. Genet.* 5:1047–1050, 1996), that has been mapped to this region of the proximal long arm of chromosome 14 by linkage analysis in two kindreds. Pedigree analysis of the DFNA9 kindred suggests that the mutant gene has complete penetrance. Hearing loss begins in the third decade and is variably progressive with high frequencies affected first, followed by middle and low frequencies. DFNA9 maps within a 9-cM interval from D14S252 to D14S49, which is centromeric to the DFNB5 map assignment.

To evaluate where hCOCH5B2 maps with respect to this disease loci and in relation to markers on the Whitehead map, a more precise map assignment was needed. A BLAST search of dbSTS was performed, which resulted in the identification of an STS identical to hCOCH5B2 sequence designated W1–12411, which maps by radiation hybrid analysis to 14q12–q13, in agreement with the FISH assignment. The map position assigned to W1–12411 by the Whitehead Institute/MIT Center for Genome Research is between markers AFMB297XB9 and WI-4859, placing hCOCH5B2 completely within the interval for DFNA9, indicating hCOCH5B2 as a candidate for this disorder.

To assess further the map position of hCOCH5B2 in relation to the STS markers that are linked to DFNA9, the presence of hCOCH5B2 and DFNA9 disease markers on a series of overlapping YACs spanning the disease locus were evaluated. Primer pairs from three STSs (D14S54, D14S121, and D14S49) with highest lod scores for linkage to DFNA9 (Manolis et al., *Hum. Mol. Genet.* 5:1047–1050, 1996) were used for PCR on six YACs (784-D-11, 888-C-6, 949-A-9, 925-C-2, 746-F-10, and 964-F-6). Primers from hCOCH5B2 were also used to detect presence of this gene on these YACs. Table 1 summarizes the presence (+) or absence (−) of the hCOCH5B2 gene on the designated YAC. hCOCH5B2 was present on three overlapping YACs, two of which also contained one of the STS markers linked to DFNA9. These data further confirm hCOCH5B2 as a strong positional candidate gene for DFNA9, warranting mutation analysis of this gene for this disorder.

TABLE 1

Presence of COCH5B2 and DFNA9 Markers on YACs

| YACs | COCH5B2 | D14S54 | D14S121 | D14S49 |
|---|---|---|---|---|
| 784-D-11 | − | − | − | − |
| 888-C-6 | + | − | − | − |
| 949-A-9 | + | + | − | − |
| 925-C-2 | + | + | − | − |
| 746-F-10 | − | + | − | − |
| 964-F-6 | − | − | + | + |

Mapping in Mouse mCOCH5B2 was mapped to chromosome 12, in a region of homologous synteny to human 14q11.2–q13. Segregation of mCOCH5B2 was compared with that of marker loci previously typed in a panel of DNAs derived from progeny of matings between female (C57BL/6JXCAST/Ei)F1 hybrids and male C57BL/6J. Restriction fragment length variants of 9.0 kb in C57BL/6J and 5.9 kb in CAST/Ei were detected in a TaqI digest probed with the 600-bp hCOCH5B2 cDNA. Gene order was determined on chromosome 12, placing mCOCH5B2 between the markers D12Mit2 and D12Mit200, which have been located at positions 19 and 29, respectively, on the Mouse Genome Database (MGD) composite map of chromosome 12 (Mouse Genome Database, 1997). (The mouse mapping data have been deposited with the MGD under Accession No. MGD-JNUM-40510. The official Mouse Gene Mapping nomenclature for mCOCH5B2 is D12H14S564E.) The human and mouse map assignments are consistent with previously defined human-mouse conserved gene arrangements between mouse chromosome 12 and human chromosome 14. For example, Pax9 has been placed at position 26 on mouse 12 (Mouse Genome Database, 1997) near where we have localized mCOCH5B2. The human homolog of Pax9 maps to the q11–q13 region of human chromosome 14.

This region on mouse 12 to which mCOCH5B2 maps contains the asp1 (audiogenic seizure prone) locus characterized by susceptibility to sound-induced convulsions (Collins and Fuller, Science 162:1137–1139, 1968). Using BXD recombinant inbred strain analysis, asp1 was mapped between Ahr and D12Nyu1 on mouse chromosome 12 (Neumann and Seyfried, Behav. Genet. 20:307–323, 1990), corresponding to a position between 18 and 23 on the MGD composite map.

Although asp1 in the mouse and DFNA9 in the human are phenotypically very different, it is not known whether they could represent involvement of homologous genes in the two species. By chromosomal localization, COCH5B2 can be considered a candidate for DFNA9 and/or asp1. Further colocalization of hCOCH5B2 and DFNA9 markers to the same YACs, as well as high level expression of hCOCH5B2 only in the cochlea and vestibule (the two affected organ systems in DFNA9), further warrant the pursuit of hCOCH5B2 as a strong candidate for the nonsyndromic DFNA9.

In Situ Hybridization

For more precise localization of COCH5B2 expression within the inner ear, in situ hybridization was performed on late embryonic and posthatching chicken cochlea and vestibular tissue. COCH5B2 is highly conserved in human, mouse and chicken (FIG. 3), showing 94% and 79% amino acid identity of human to mouse, and to chicken, respectively. Intense COCH5B2 hybridization was detected in chicken sections in spindle-shaped cells located along nerve fibers between the auditory ganglion and the sensory epithelium. These cells accompany neurites at the site where they traverse the habenula perforata, an opening in the cartilaginous plate. COCH5B2 message was detected also in the supporting cartilage at the neural and abnerual limbs, on the medial and lateral edges of the sensory epithelium but not in any other cartilaginous tissues in the chicken. In the vestibular labyrinth, strong COCH5B2 hybridization was detected in the stroma underlying the sensory epithelium of the crista ampularis, and in the area adjacent to vestibular nerve fibers.

The pattern of COCH5B2 expression in chicken inner ear remarkably parallels the histological findings of acidophilic ground substance in the temporal bones evaluated from several DFNA9 patients (Khetarpal et al., Arch. Otolaryngol. Head Neck Surg. 117:1032–1042, 1991, Khetarpal, Arch. Otolaryngol. Head Neck Surg. 119:106–108, 1993). The acidophilic substance was found in the osseous spiral lamina (corresponding to the region of nerve fibers of the chicken auditory ganglion) and in cochlear nerve channels. The spiral limbs and the spiral ligament (corresponding to the neural and abneural limbs of the chicken sensory epithelium), which serve as support structures for the organ of Corti were also filled with this homogeneous substance in DFNA9 patients.

The acidophilic material has been detected also in the vestibular labyrinths of DFNA9 patients (Khetarpal et al., Arch. Otolaryngol. Head Neck Surg. 117:1032–1042, 1991, Khetarpal, Arch. Otolaryngol. Head Neck Surg. 119:106–108, 1993) in anatomically similar structures as in the cochlea and in the chicken vestibular system: the stroma of the maculae and cristae underlying the sensory epithelium and the cribrose area containing the vestibular nerve fibers. The striking correlation of COCH5B2 expression pattern in chicken inner ear to histopathological findings in DFNA9 patients, and very high level expression in the cochlea and vestibule, the only two organ systems known to be affected in DFNA9, further substantiated COCH5B2 as a strong candidate for this disorder, warranting mutation analysis in DFNA9 patients.

In addition to the original DFNA9 kindred (Manolis et al., Hum. Mol. Genet, 5:1047–1050, 1996), characteristic inner ear histopathology had been reported also in a second family (Khetarpal et al., Arch. Otolaryngol. Head Neck Surg. 117: 1032–1042, 1991, Khetarpal, Arch. Otolaryngol. Head Neck Surg. 119:106–108, 1993). An extensive search of temporal bone banks resulted in discovery of a third kindred (FIG. 6) with the characteristic histopathological findings. Linkage studies were performed in the second and third families establishing that their hearing also maps to the DFNA9 locus with maximum two-point lod scores of 2.08 and 2.83 at $\theta=0$, respectively.

Previous clinical evaluations of DFNA9 family members (Khetarpal et al., Arch. Otolaryngol. HeadNeck Surg. 117: 1032–1042,1991; Halpin et al., Am. J. Audiol. 5:105–111, 1996; Manolis et al., Hum. Mol. Genet. 5:1047–1050, 1996) and additional studies of the other families show sensorineural hearing loss with an autosomal dominant, fully penetrant mode of inheritance. Age of onset of hearing loss is in the second and third decades of life, is slowly progressive, more profound initially in high frequencies, with variable progression to anacusis by the fourth or fifth decades. Some DFNA9 patients have received cochlear implants and others use hearing aids. A spectrum of vestibular involvement, ranging from asymptomatic, to presence of vertigo, abnormal vestibular testing, and histopathology has been reported in family members with hearing loss.

Mutations in COCH5B2 Cause DNA9

Amino acid residues mutated in DFNA9 are evolutionarily conserved among human, mouse, and chicken COCH5B2: all three residues are identical in the three species except for a conservative change of valine at codon 66 to isoleucine in the chicken (FIG. 7C). The cluster of COCH5B2 mutations are amino-terminal to the von Willebrand factor (vWF) type A-like domains in this cochlear gene described herein. vWF type A domains are present in a variety of secreted proteins, both soluble and insoluble, involved in hemostasis, complement system, immune system, and extracellular matrix, and have been shown to bind fibrillar collagens, glycoproteins, and proteoglycans (Colombatti et al., Blood 77:2305–2315, 1991; Colombatti et al., Matrix 13:297–306, 1993).

vWF type A-like domains of COCH5B2 are flanked by, but devoid of, any cysteine residues, whereas the region of the protein showing mutations in DFNA9 is more cysteine-rich (FIG. 7), and may be critical in the structural integrity of the protein. A BLASTX search (Altschul et al., J. Mol. Biol. 215:403–410, 1990) of nonredundant translated databases revealed significant homology of this region of COCH5B2, approximately 100 amino acids in length, to a factor C domain in the ancient organism, Limulus (horseshoe crab). Factor C is a serine protease clotting factor which is activated by lipopolysaccharide binding (e.g., endotoxin), initiating a coagulation cascade (Muta et al., J. Biol. Chem. 266:6554, 1991, Iwanaga et al., Thrombosis Res. 68:1, 1992). All four cysteine residues in the domain are conserved among human, mouse, chicken COCH5B2 and Limulus factor C, and would have the potential of forming two intra-domain disulfide bonds. Of the COCH5B2 residues mutated in DFNA9, Gly88 is identical in Limulus factor C, Val66 is conserved as isoleucine, and Trp117 corresponds in Limulus factor C to a leucine, also an uncharged hydrophobic residue (FIG. 7).

The factor C homologous region of COCH5B2 contains both exons which show the three mutated nucleotides, and does not overlap with the adjacent vWF type A domain, indicating it is a distinct functional domain. This region is also physically well delineated in Limulus factor C (Muta et al., J. Biol. Chem. 266:6554, 1991, Iwanaga et al., Thrombosis Res. 68:1, 1992) and does not overlap with the well-characterized adjacent upstream "sushi" protein-binding domain, found in many mammalian complement system proteins, or with the adjacent downstream lectin-like domain, also found in mammalian proteins. Although to date no exact function has been elucidated for this specific domain, it is located within the H chain of Limulus factor C which has been shown to bind lipopolysaccharides (Nakamura, et al., Eur. J. Biochem. 176:89, 1988).

As all three COCH5B2 missense mutations fall within the conserved factor C homologous region, it will be important to determine the exact function of this domain and its role in producing DFNA9 pathology via a likely dominant negative mechanism. Amino acid changes in this cysteine-containing region may interfere with formation of disulfide bonds, disrupting proper folding and overall structure of the protein. Altered tertiary structure may perturb function of this and the downstream vWF type A domains which are expected to bind other molecules, including those with sugar moieties. COCH5B2's link to acidophilic ground substance deposition may be directly through precipitation and accumulation of aberrant protein itself, or through abnormal interaction with other extracellular components in the inner ear, required for clearing of these substances or for proper organization of various elements in the inner ear.

Mechanoelectrical transduction and functioning of both cochlear and vestibular hair cells is tightly dependent on the maintenance of the precise architecture and innervation of these labyrinths. A number of mouse mutants with hearing loss, such as shaker, spinner, and waltzer, have associated vestibular defects, and in many cases were identified by, and named for, the abnormal circling behavior they exhibit (Steel et al., Trends in Genet. 10:4280434, 1994; Petit, Nature Genet. 14:385–391, 1996). In humans, hearing impairment and vestibular malfunction also may be found together, however, the magnitude of vestibular involvement may be underestimated, due to other compensatory systems in humans. Structural features of COCH5B2 consistent with a secreted protein, its expression pattern in the cochlear and vestibular labyrinths, and its involvement in DFNA9 provide valuable insight into its common role in the structural integrity and proper functioning of the inner ear.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed is:

1. A nucleic acid primer for diagnosing a hearing disorder which hybridizes under stringent conditions to a portion of the nucleic acid sequence of SEQ ID NO: 1 or complement thereof, wherein the primer amplifies all or a portion of exons 4 and 5 of SEQ ID NO: 1 such that one or more nucleotides encoding one or more of an amino acid at residue 51, an amino acid at residue 66, an amino acid at residue 88 and an amino acid at residue 117 of SEQ ID NO:2 is amplified.

2. The nucleic acid primer of claim 1, wherein the primer amplifies a portion of exon 4 that comprises nucleic acids encoding a proline at residue 51 of SEQ ID NO:2.

3. The nucleic acid primer of claim 1, wherein the primer amplifies a portion of exon 4 that comprises nucleic acids encoding a valine at residue 66 of SEQ ID NO:2.

4. The nucleic acid primer of claim 1, wherein the primer amplifies a portion of exon 5 that comprises nucleic acids encoding a glycine at residue 88 of SEQ ID NO:2.

5. The nucleic acid primer of claim 1, wherein the primer amplifies a portion of exon 5 that comprises nucleic acids encoding a tryptophan at residue 117 of SEQ ID NO:2.

6. The nucleic acid primer of claim 1, wherein the hearing disorder is DNFA9.

7. The nucleic acid primer of claim 1, wherein the primer is at least 12 nucleotides in length.

8. The nucleic acid primer of claim 1, wherein the primer comprises at least 12 consecutive nucleotides of SEQ ID NO: 1.

9. A nucleic acid probe for diagnosing a hearing disorder which hybridizes under stringent conditions to the complement of SEQ ID NO: 1 or a nucleic acid sequence that differs from the SEQ ID NO: 1 at one or more nucleotides encoding one or more of a proline at residue 51 of SEQ ID NO:2, a valine at residue 66 of SEQ ID NO:2, a glycine at residue 88 of SEQ ID NO:2, and a tryptophan at residue 117 of SEQ ID NO:2 and which detects the absence or presence of a substitution at one or more nucleic acids that encode the proline at residue 51 of SEQ ID NO:2, the valine at residue 66 of SEQ ID NO:2, the glycine at residue 88 of SEQ ID NO:2, or the tryptophan at residue 117 of SEQ ID NO:2.

10. The nucleic acid probe of claim 9, wherein the probes hybridizes to a portion of the complement of SEQ ID NO: 1 or the nucleic acid such that a lesion at one or more nucleic acids encoding a proline at residue 51 of SEQ ID NO:2 is detected.

11. The nucleic acid probe of claim 9, wherein the probe is labeled.

12. The nucleic acid probe of claim 9, wherein the hearing disorder is DFNA9.

13. The nucleic acid probe of claim 10, wherein the probe detects a lesion at nucleotide 207 of SEQ ID NO: 1.

14. The nucleic acid probe of claim 9, wherein the probe hybridizes to a portion of the complement of SEQ ID NO: 1 or the nucleic acid such that a lesion at one or more nucleic acids encoding a proline at residue 88 of SEQ ID NO:2 is detected.

15. The nucleic acid probe of claim 14, wherein the probe detects a lesion at nucleotide 319 of SEQ ID NO: 1.

16. The nucleic acid probe of claim 9, wherein the probe hybridizes to a portion of the complement of SEQ ID NO: 1 or the nucleic acid such that a lesion at one or more nucleic acids encoding a proline at residue 117 of SEQ ID NO:2 is detected.

17. The nucleic acid probe of claim 16, wherein the probe detects a lesion at nucleotide 405 of SEQ ID NO: 1.

18. The nucleic acid probe of claim 9, wherein the probe is at least 12 nucleotides in length.

19. The nucleic acid probe of claim 9, wherein the probe comprises at least 12 consecutive nucleotides of SEQ ID NO:1.

20. A kit for diagnosing a subject at risk for a hearing disorder, comprising: at least two nucleic acid primers which hybridize under stringent conditions to a nucleic acid sequence of SEQ ID NO: 1 or complement thereof, wherein the primers amplify all or a portion of exons 4 and 5 of SEQ ID NO: 1 such that one or more nucleotides encoding one or more of an amino acid at residue 51, an amino acid at residue 66, an amino acid at residue 88 and an amino acid at residue 117 of SEQ ID NO:2 is amplified; and instructions for diagnosing a hearing disorder by detecting a substitution of one or more nucleotides encoding one or more of a proline at residue 51 of SEQ ID NO:2, a valine at residue 66 of SEQ ID NO:2, a glycine at residue 88 of SEQ ID NO:2, and a tryptophan at residue 117 of SEQ ID NO:2.

21. The kit of claim 20, wherein the hearing disorder is DNFA9.

22. The kit of claim 20, further comprising a nucleic acid probe which hybridizes under stringent conditions to the complement of SEQ ID NO: 1, or a nucleic acid sequence that differs from SEQ ID NO: 1 at one or more nucleotides encoding one or more of a proline at residue 51 of SEQ ID NO:2, a valine at residue 66 of SEQ ID NO:2, a glycine at residue 88 of SEQ ID NO:2, and a tryptophan at residue 117 of SEQ ID NO:2 and which detects the absence or presence of a substitution at one or more nucleic acids that encode the proline at residue 51 of SEQ ID NO:2, the valine at residue 66 of SEQ ID NO:2, the glycine at residue 88 of SEQ ID NO:2, or the tryptophan at residue 117 of SEQ ID NO:2.

23. The kit of claim 22, wherein the kit comprises more than one probe.

24. The kit of claim 22, wherein the probe is a labeled probe.

25. The kit of claim 23, wherein one or more of the probes is a labeled probe.

26. The kit of claim 22, wherein the primer is at least 12 nucleotides in length.

27. The kit of claim 22, wherein the primer comprises at least 12 consecutive nucleotides of SEQ ID NO: 1.

28. A kit for diagnosing a subject at risk for a hearing disorder, comprising: one or more nucleic acid probes which hybridize under stringent conditions to the complement of SEQ ID NO: 1 or a nucleic acid sequence that differs from the SEQ ID NO: 1 at one or more nucleotides encoding one or more of a proline at residue 51 of SEQ ID NO:2, a valine at residue 66 of SEQ ID NO:2, a glycine at residue 88 of SEQ ID NO:2, and a tryptophan at residue 117 of SEQ ID NO:2 and which detects the absence or presence of a substitution at one or more nucleic acids that encode the proline at residue 51 of SEQ ID NO:2, the valine at residue 66 of SEQ ID NO:2, the glycine at residue 88 of SEQ ID NO:2, or the tryptophan at residue 117 of SEQ ID NO:2; and instructions for diagnosing a hearing disorder by amplifying all or a portion of SEQ ID NO: 1 such that one or more nucleotides encoding one or more of an amino acid at residue 51, an amino acid at residue 66, an amino acid at residue 88 and an amino acid at residue 117 of SEQ ID NO:2 is amplified and detecting the absence or presence of a substitution of one or more nucleotides encoding one or more of a proline at residue 51 of SEQ ID NO:2, a valine at residue 66 of SEQ ID NO:2, a glycine at residue 88 of SEQ ID NO:2, and a tryptophan at residue 117 of SEQ ID NO:2.

29. The kit of claim 28, wherein the hearing disorder is DFNA9.

30. The kit of claim 28, wherein the probe is a labeled probe.

31. The kit of claim 28, wherein the kit comprises two or more probes and at least one of the probes is a labeled probe.

32. The kit of claim 28, wherein the probe is at least 12 nucleotides in length.

33. The kit of claim 28, wherein the probe comprises at least 12 consecutive nucleotides of SEQ ID NO: 1.

* * * * *

UNITED STATES PATENT AND TRADEMARK OFFICE
CERTIFICATE OF CORRECTION

PATENT NO. : 7,030,235 B1 Page 1 of 1
APPLICATION NO. : 09/394264
DATED : April 18, 2006
INVENTOR(S) : Cynthia Morton and Nahid Robertson It is certified that error appears in the above-identified patent and that said Letters Patent is hereby corrected as shown below:

Title Page, item (56), References Cited OTHER PUBLICATIONS, reference Robertson et al.:
    delete "canidate" and replace with --candidate--

Title Page, item (56), References Cited OTHER PUBLICATIONS, reference Heller et al.:
    delete "Academey" and replace with --Academy--

Title Page, item (56), References Cited OTHER PUBLICATIONS, reference Ahn et al.:
    delete "sequnece" and replace with --sequence--

Title Page, item (56), References Cited OTHER PUBLICATIONS, 1st for reference Colombatti et al.:
    delete "1993" and replace with --1991--

Signed and Sealed this

Twenty-sixth Day of December, 2006

JON W. DUDAS
*Director of the United States Patent and Trademark Office*